(12) United States Patent
Wahlbin et al.

(10) Patent No.: US 7,904,318 B2
(45) Date of Patent: *Mar. 8, 2011

(54) COMPUTERIZED METHOD AND SYSTEM OF DETERMINING RIGHT OF WAY AND LIABILITY FOR AN ACCIDENT

(75) Inventors: Stephan Wahlbin, Austin, TX (US); Tim Johnston, Georgetown, TX (US)

(73) Assignee: Computer Sciences Corporation, El Segundo, CA (US)

(*) Notice: Subject to any disclaimer, the term of this patent is extended or adjusted under 35 U.S.C. 154(b) by 2249 days.

This patent is subject to a terminal disclaimer.

(21) Appl. No.: 09/969,017

(22) Filed: Oct. 2, 2001

(65) Prior Publication Data
US 2002/0082873 A1    Jun. 27, 2002

Related U.S. Application Data

(60) Provisional application No. 60/237,744, filed on Oct. 2, 2000.

(51) Int. Cl.
*G06Q 40/00* (2006.01)
(52) U.S. Cl. .......... 705/4; 702/151; 702/159; 703/6; 703/7
(58) Field of Classification Search ............ 705/4
See application file for complete search history.

(56) References Cited

U.S. PATENT DOCUMENTS

| | | | |
|---|---|---|---|
| 4,166,599 A | 9/1979 | Auer et al. | |
| 4,638,289 A | 1/1987 | Zottnik | |
| 4,656,585 A | 4/1987 | Stephenson | |
| 4,839,822 A | 6/1989 | Dormond et al. | |
| 4,878,167 A | 10/1989 | Kapulka et al. | |
| 4,931,793 A | 6/1990 | Fuhrmann et al. | |

(Continued)

FOREIGN PATENT DOCUMENTS

EP    0 280 773    9/1988

(Continued)

OTHER PUBLICATIONS

Policy Management Systems Corporation Announces Pilot Licensing of Claims Outcome Advisor(TM) to Blue Ridge Insurance Co., PR Newswire. New York: Aug 24, 1999. p. 1.*

(Continued)

*Primary Examiner* — R. D Rines
(74) *Attorney, Agent, or Firm* — Meyertons, Hood, Kivlin, Kowert & Goetzel, P.C.; Eric B. Meyertons

(57) ABSTRACT

Methods and systems are provided for estimating liability and right of way in an accident. In one embodiment, liability estimation in a vehicle accident may be based on a plurality of characteristics that describe the accident. In addition, right of way estimation in a vehicle accident may be based on the plurality of characteristics that describe the accident. These characteristics may include: the configuration of the roadway, the type of accident, the traffic controls at the vehicle accident scene, and impact points of each vehicle. The characteristics from an actual accident may be compared to those in a past or theoretical accident. Liability may be estimated from a preassigned liability associated with a nearest matching past or theoretical accident. Right of way may be estimated from a predetermined right of way associated with the nearest matching past or theoretical accident. The liability estimate may include a base liability and one or more adjustments due to various factors.

33 Claims, 61 Drawing Sheets

U.S. PATENT DOCUMENTS

| | | | |
|---|---|---|---|
| 5,099,422 A | 3/1992 | Foresman et al. | |
| 5,128,859 A | 7/1992 | Carbone et al. | |
| 5,172,281 A | 12/1992 | Ardis et al. | |
| 5,180,309 A | 1/1993 | Egnor | |
| 5,191,522 A | 3/1993 | Bosco et al. | |
| 5,201,044 A | 4/1993 | Frey, Jr. et al. | |
| 5,233,513 A | 8/1993 | Doyle | |
| 5,243,524 A | 9/1993 | Ishida et al. | |
| 5,317,503 A | 5/1994 | Inoue | |
| 5,386,566 A | 1/1995 | Hamanaka et al. | |
| 5,394,555 A | 2/1995 | Hunter et al. | |
| 5,434,994 A | 7/1995 | Shaheen et al. | |
| 5,446,659 A | 8/1995 | Yamawaki | |
| 5,455,947 A | 10/1995 | Suzuki et al. | |
| 5,483,442 A | 1/1996 | Black et al. | |
| 5,483,632 A | 1/1996 | Kuwamoto et al. | |
| 5,499,330 A | 3/1996 | Lucas et al. | |
| 5,504,674 A | 4/1996 | Chen et al. | |
| 5,523,942 A | 6/1996 | Tyler et al. | |
| 5,524,489 A | 6/1996 | Twigg | |
| 5,550,976 A | 8/1996 | Henderson et al. | |
| 5,557,515 A | 9/1996 | Abbruzzese et al. | |
| 5,585,798 A | 12/1996 | Yoshioka et al. | |
| 5,586,310 A | 12/1996 | Sharman | |
| 5,638,508 A | 6/1997 | Kanai et al. | |
| 5,652,705 A | 7/1997 | Spiess | |
| 5,689,706 A | 11/1997 | Rao et al. | |
| 5,710,578 A | 1/1998 | Beauregard et al. | |
| 5,717,391 A | 2/1998 | Rodriguez | |
| 5,745,901 A | 4/1998 | Entner et al. | |
| 5,768,505 A | 6/1998 | Gilchrist et al. | |
| 5,768,506 A | 6/1998 | Randell | |
| 5,787,269 A | 7/1998 | Hyodo | |
| 5,787,429 A | 7/1998 | Nikolin | |
| 5,797,134 A | 8/1998 | McMillan et al. | |
| 5,798,949 A | 8/1998 | Kaub | |
| 5,815,093 A | 9/1998 | Kikinis | |
| 5,832,481 A | 11/1998 | Sheffield | |
| 5,862,500 A | 1/1999 | Goodwin | |
| 5,870,711 A | 2/1999 | Huffman | |
| 5,873,066 A | 2/1999 | Underwood et al. | |
| 5,877,707 A | 3/1999 | Kowalick | |
| 5,907,848 A | 5/1999 | Zaiken et al. | |
| 5,909,683 A | 6/1999 | Miginiac et al. | |
| 5,930,759 A | 7/1999 | Moore et al. | |
| 5,933,816 A | 8/1999 | Zeanah et al. | |
| 5,937,189 A | 8/1999 | Branson et al. | |
| 5,948,035 A | 9/1999 | Tomita | |
| 5,950,169 A | 9/1999 | Borghesi et al. | |
| 5,987,434 A | 11/1999 | Libman | |
| 5,991,733 A | 11/1999 | Aleia et al. | |
| 6,009,402 A | 12/1999 | Whitworth | |
| 6,037,860 A | 3/2000 | Zander et al. | |
| 6,038,393 A | 3/2000 | Iyengar et al. | |
| 6,043,813 A | 3/2000 | Stickney et al. | |
| 6,049,665 A | 4/2000 | Branson et al. | |
| 6,064,983 A | 5/2000 | Koehler | |
| 6,076,026 A | 6/2000 | Jambhekar et al. | |
| 6,081,832 A | 6/2000 | Gilchrist et al. | |
| 6,092,049 A | 7/2000 | Chislenko et al. | |
| 6,098,070 A | 8/2000 | Maxwell | |
| 6,105,007 A | 8/2000 | Norris | |
| 6,115,690 A | 9/2000 | Wong | |
| 6,134,582 A | 10/2000 | Kennedy | |
| 6,141,015 A | 10/2000 | Tanaka | |
| 6,141,611 A | 10/2000 | Mackey et al. | |
| 6,161,071 A | 12/2000 | Shuman et al. | |
| 6,163,770 A | 12/2000 | Gamble et al. | |
| 6,173,284 B1 | 1/2001 | Brown | |
| 6,184,782 B1 | 2/2001 | Oda et al. | |
| 6,185,490 B1 | 2/2001 | Ferguson | |
| 6,185,540 B1 | 2/2001 | Schreitmueller et al. | |
| 6,223,125 B1 | 4/2001 | Hall | |
| 6,226,623 B1 | 5/2001 | Schein et al. | |
| 6,236,975 B1 | 5/2001 | Boe et al. | |
| 6,246,933 B1 | 6/2001 | Bague | |
| 6,254,127 B1 | 7/2001 | Breed et al. | |
| 6,268,804 B1 | 7/2001 | Janky et al. | |
| 6,308,187 B1 | 10/2001 | DeStefano | |
| 6,336,096 B1 * | 1/2002 | Jernberg | 705/4 |
| 6,351,893 B1 | 3/2002 | St. Pierre | |
| 6,363,360 B1 | 3/2002 | Madden | |
| 6,397,334 B1 | 5/2002 | Chainer et al. | |
| 6,405,132 B1 | 6/2002 | Breed et al. | |
| 6,408,304 B1 | 6/2002 | Kumhyr | |
| 6,446,086 B1 | 9/2002 | Bartlett et al. | |
| 6,473,084 B1 | 10/2002 | Phillips et al. | |
| 6,493,650 B1 | 12/2002 | Rodgers et al. | |
| 6,525,672 B2 | 2/2003 | Chainer et al. | |
| 6,532,459 B1 | 3/2003 | Berson | |
| 6,570,609 B1 * | 5/2003 | Heien | 348/148 |
| 6,604,080 B1 | 8/2003 | Kern | |
| 6,675,074 B2 | 1/2004 | Hathout et al. | |
| 6,696,929 B2 | 2/2004 | Igaki et al. | |
| 6,832,205 B1 | 12/2004 | Aragones et al. | |
| 6,850,843 B2 | 2/2005 | Smith et al. | |
| 6,925,468 B1 | 8/2005 | Doughty et al. | |
| 6,938,029 B1 | 8/2005 | Tien | |
| 6,952,741 B1 | 10/2005 | Bartlett et al. | |
| 6,961,708 B1 | 11/2005 | Bierenbaum | |
| 6,970,844 B1 | 11/2005 | Bierenbaum | |
| 7,013,284 B2 * | 3/2006 | Guyan et al. | 705/9 |
| 7,024,418 B1 | 4/2006 | Childress et al. | |
| 7,051,046 B2 | 5/2006 | Virag et al. | |
| 7,095,426 B1 | 8/2006 | Childress | |
| 7,197,444 B2 | 3/2007 | Bomar, Jr. et al. | |
| 7,337,121 B1 | 2/2008 | Beinat et al. | |
| 7,343,307 B1 | 3/2008 | Childress | |
| 7,353,196 B1 | 4/2008 | Doughty et al. | |
| 7,356,541 B1 | 4/2008 | Doughty | |
| 7,359,863 B1 | 4/2008 | Evenshaug et al. | |
| 7,363,264 B1 | 4/2008 | Doughty et al. | |
| 7,398,219 B1 | 7/2008 | Wolfe | |
| 7,418,400 B1 | 8/2008 | Lorenz | |
| 7,430,514 B1 | 9/2008 | Childress et al. | |
| 7,430,515 B1 | 9/2008 | Wolfe et al. | |
| 2001/0037223 A1 | 11/2001 | Beery et al. | |
| 2001/0041993 A1 | 11/2001 | Campbell | |
| 2001/0044735 A1 | 11/2001 | Colburn et al. | |
| 2002/0004729 A1 | 1/2002 | Zak et al. | |
| 2002/0007289 A1 | 1/2002 | Malin et al. | |
| 2002/0035488 A1 * | 3/2002 | Aquila et al. | 705/4 |
| 2002/0049619 A1 | 4/2002 | Wahlbin et al. | |
| 2002/0055860 A1 | 5/2002 | Wahlbin et al. | |
| 2002/0055861 A1 | 5/2002 | King et al. | |
| 2002/0059083 A1 | 5/2002 | Wahlbin et al. | |
| 2002/0059084 A1 | 5/2002 | Wahlbin et al. | |
| 2002/0059085 A1 | 5/2002 | Wahlbin et al. | |
| 2002/0059086 A1 | 5/2002 | Wahlbin et al. | |
| 2002/0059087 A1 | 5/2002 | Wahlbin et al. | |
| 2002/0059097 A1 | 5/2002 | Wahlbin et al. | |
| 2002/0062232 A1 | 5/2002 | Wahlbin et al. | |
| 2002/0062233 A1 | 5/2002 | Wahlbin et al. | |
| 2002/0062234 A1 | 5/2002 | Wahlbin et al. | |
| 2002/0062235 A1 | 5/2002 | Wahlbin et al. | |
| 2002/0069091 A1 | 6/2002 | Wahlbin et al. | |
| 2002/0069092 A1 | 6/2002 | Wahlbin et al. | |
| 2002/0082873 A1 | 6/2002 | Wahlbin et al. | |
| 2002/0087363 A1 | 7/2002 | Wahlbin et al. | |
| 2002/0091504 A1 | 7/2002 | Wahlbin et al. | |
| 2002/0128881 A1 | 9/2002 | Wahlbin et al. | |
| 2002/0133362 A1 | 9/2002 | Karathanasis et al. | |
| 2002/0145666 A1 | 10/2002 | Scaman et al. | |
| 2002/0161597 A1 | 10/2002 | Klibaner | |
| 2003/0125991 A1 | 7/2003 | Logan | |
| 2003/0200123 A1 | 10/2003 | Burge et al. | |
| 2004/0030587 A1 | 2/2004 | Danico et al. | |
| 2004/0049409 A1 | 3/2004 | Wahlbin et al. | |
| 2004/0054556 A1 | 3/2004 | Wahlbin et al. | |
| 2004/0054557 A1 | 3/2004 | Wahlbin et al. | |
| 2004/0054558 A1 | 3/2004 | Wahlbin et al. | |
| 2004/0054559 A1 | 3/2004 | Wahlbin et al. | |
| 2004/0088198 A1 | 5/2004 | Childress et al. | |
| 2004/0102984 A1 | 5/2004 | Wahlbin et al. | |
| 2004/0102985 A1 | 5/2004 | Wahlbin et al. | |
| 2004/0103004 A1 | 5/2004 | Wahlbin et al. | |
| 2004/0103005 A1 | 5/2004 | Wahlbin et al. | |

| | | | |
|---|---|---|---|
| 2004/0103006 A1 | 5/2004 | Wahlbin et al. |
| 2004/0103007 A1 | 5/2004 | Wahlbin et al. |
| 2004/0103008 A1 | 5/2004 | Wahlbin et al. |
| 2004/0103009 A1 | 5/2004 | Wahlbin et al. |
| 2004/0103010 A1 | 5/2004 | Wahlbin et al. |
| 2004/0111301 A1 | 6/2004 | Wahlbin et al. |
| 2004/0205562 A1 | 10/2004 | Rozek et al. |
| 2005/0060205 A1 | 3/2005 | Woods et al. |
| 2005/0192850 A1 | 9/2005 | Lorenz |
| 2005/0198154 A1 | 9/2005 | Xie et al. |
| 2006/0031103 A1 | 2/2006 | Henry |
| 2007/0214020 A1 | 9/2007 | Srinivasan et al. |

FOREIGN PATENT DOCUMENTS

| | | |
|---|---|---|
| EP | 0 465 018 | 1/1992 |
| EP | 0 926 608 | 6/1999 |
| GB | 2054229 | 2/1981 |
| JP | 10197285 | 7/1998 |
| JP | 10214283 | 8/1998 |
| JP | 111611711 | 6/1999 |
| WO | 9506884 | 3/1995 |

OTHER PUBLICATIONS

CSC Files Suit to Protect Intellectual Property, PR Newswire. New York: Jan. 12, 2000. p. 1.*
CSC Introduces Liability Assessment Tool to Improve Claims Consistency, PR Newswire. New York: Oct. 31, 2000. p. 1.*
Trademark for @Fault, accessed from uspto.gov on Feb. 8, 2006.*
"ISO to Acquire Claims Outcome Advisor from Computer Sciences and MYND," Dec. 21, 2000, accessed at www.swampfox.ws.*
CSC website, "Fault Evaluator," www.csc.com, accessed on Feb. 8, 2006.*
ISO Liability Advisor, www.iso.com, accessed on Feb. 8, 2006.*
IBC.com, accessed at http://www.icbc.com/claims-repairs/claims_fault_nofault.asp on May 2, 2007.*
Michelle J. White, An Empirical Test of the Comparative and Contributory Negligence Rules in Accident Law, The RAND Journal of Economics, vol. 20, No. 3. Autumn 1989, pp. 308-330.*
Continuum Connections, vol. I, No. 1, The Continuum Company, Inc., Nov. 1991, 16 pages.
Continuum Connections, vol. I, No. 2, The Continuum Company, Inc., Jan./Feb. 1992, 17 pages.
Continuum Connections, vol. I, No. 3, The Continuum Company, Inc., Mar./Apr. 1992, 16 pages.
Continuum Connections, vol. I, No. 4, The Continuum Company, Inc., Jul./Aug. 1992, 15 pages.
Continuum Connections, vol. II, No. 1, The Continuum Company, Inc., Oct./Nov. 1992, 16 pages.
Continuum Connections, vol. II, No. 2, The Continuum Company, Inc., Dec./Jan. 1993, 24 pages.
Continuum Connections, vol. II, No. 3, The Continuum Company, Inc., Mar./Apr. 1993, 16 pages.
Continuum Connections, vol. II, No. 4, The Continuum Company, Inc., Jul./Aug. 1993, 16 pages.
Continuum Connections, vol. II, No. 5, The Continuum Company, Inc., Nov./Dec. 1993, 20 pages.
Continuum Connections, vol. II, No. 6, The Continuum Company, Inc., Jan./Feb. 1994, 19 pages.
Continuum Connections, vol. III, No. 1, The Continuum Company, Inc., Mar./Apr. 1994, 24 pages.
Continuum Connections, vol. III, No. 2, The Continuum Company, Inc., Nov./Dec. 1994, 20 pages.
Continuum Connections, vol. III, No. 3, The Continuum Company, Inc., Mar./Apr. 1995, 16 pages.
Continuum Connections to the Americas, vol. 1, No. 1, The Continuum Company, Inc., Sep. 1995, 49 pages.
Continuum Connections, vol. III, No. 4, The Continuum Company, Inc., Oct./Nov. 1995, 24 pages.
Continuum Connections to the Americas, vol. 2, No. 1, The Continuum Company, Inc., Jan. 1996, 59 pages.
Continuum Connections to the Americas, vol. 2, No. 2, The Continuum Company, Inc., Mar. 1996, 59 pages.
Continuum Connections to the Americas, vol. 2, No. 3, The Continuum Company, Inc., May 1996, 51 pages.
Continuum Connections to the Americas, vol. 2, No. 4, The Continuum Company, Inc., Jul. 1996, 55 pages.
Continuum Connections to the Americas, vol. 2, No. 5, The Continuum Company, Inc., Sep. 1996, 59 pages.
Connections to the Americas, vol. 3, No. 1, CSC Continuum, Jan. 1997, 55 pages.
Connections to the Americas, vol. 3, No. 2, CSC Continuum, Feb. 1997, 55 pages.
Connections to the Americas, vol. 3, No. 3, CSC Continuum, Mar. 1997, 48 pages.
Connections to the Americas, vol. 3, No. 4, CSC Continuum, Apr. 1997, 40 pages.
Connections to the Americas, vol. 3, No. 5, Computer Sciences Corporation, May/Jun. 1997, 66 pages.
Connections to the Americas, vol. 3, No. 6, Computer Sciences Corporation, Jul./Aug. 1997, 56 pages.
Connections to the Americas, vol. 3, No. 7, Computer Sciences Corporation, Sep./Oct. 1997, 76 pages.
Connections to the Americas, vol. 4, No. 1, Computer Sciences Corporation, Jan. 1998, 64 pages.
Connections to the Americas, vol. 4, No. 2, Computer Sciences Corporation, Feb./Mar. 1998, 50 pages.
Connections to the Americas, vol. 4, No. 3, Computer Sciences Corporation, May/Jun. 1998, 48 pages.
Connections to the Americas, vol. 4, No. 4, Computer Sciences Corporation, Sep./Oct. 1998, 62 pages.
Insurance Connections, Computer Sciences Corporation, Feb./Mar. 1999, 52 pages.
Banking Connections, Computer Sciences Corporation, Apr./May 1999, 44 pages.
Insurance Connections, Computer Sciences Corporation, Jun./Jul. 1999, 56 pages.
Banking Connections, Computer Sciences Corporation, Aug./Sep. 1999, 52 pages.
Insurance Connections, Computer Sciences Corporation, Oct./Nov. 1999, 56 pages.
Cost Containment: Products and Solutions for the Property and Casualty Insurance Industry, Computer Sciences Corporation, Oct. 1999, 40 pages.
Banking Connections, Computer Sciences Corporation, Dec. 1999, 48 pages.
Insurance Connections, Computer Sciences Corporation, Feb./Mar. 2000, 60 pages.
Banking Connections, Computer Sciences Corporation, Apr./May 2000, 48 pages.
Insurance Connections, Computer Sciences Corporation, Jun./Jul. 2000, 43 pages.
Insurance Connections, Computer Sciences Corporation, Sep./Oct. 2000, 43 pages.
Banking Connections, Computer Sciences Corporation, Nov./Dec. 2000, 48 pages.
Connections, Computer Sciences Corporation, Mar./Apr. 2001, 58 pages.
Connections, Computer Sciences Corporation, Jun. 2001, 44 pages.
Connections, Computer Sciences Corporation, Oct. 2001, 39 pages.
Connections, Computer Sciences Corporation, Dec. 2001, 39 pages.
Scopus and Entrust: Call Center Sales Helper is Unveiled, Nov. 10, 1997; vol. 162, Issue 217, p. 19.
International search report application No. PCT/US 01/30822, mailed Jan. 22, 2002, 5 pages.
U.S. Appl. No. 09/603,302.
U.S. Appl. No. 09/629,834.
U.S. Appl. No. 09/648,247.
U.S. Appl. No. 09/699,036.
U.S. Appl. No. 09/699,015.
U.S. Appl. No. 09/699,054.
U.S. Appl. No. 09/699,038.
U.S. Appl. No. 09/699,021.
U.S. Appl. No. 09/699,058.
U.S. Appl. No. 09/699,056.
U.S. Appl. No. 09/699,037.
U.S. Appl. No. 09/345,698.
U.S. Appl. No. 09/345,699.

U.S. Appl. No. 09/527,110.
U.S. Appl. No. 09/527,325.
U.S. Appl. No. 09/527,324.
U.S. Appl. No. 09/603,307.
U.S. Appl. No. 09/603,129.
U.S. Appl. No. 09/603,662.
U.S. Appl. No. 09/603,308.
U.S. Appl. No. 09/603,144.
U.S. Appl. No. 09/602,687.
U.S. Appl. No. 09/602,691.
U.S. Appl. No. 09/603,130.
U.S. Appl. No. 09/603,303.
U.S. Appl. No. 09/603,304.
U.S. Appl. No. 09/648,921.
U.S. Appl. No. 09/648,246.
U.S. Appl. No. 09/648,655.
U.S. Appl. No. 09/603,306.
U.S. Appl. No. 09/386,862.
U.S. Appl. No. 09/386,858.
U.S. Appl. No. 09/675,379.
U.S. Appl. No. 09/676,018.
U.S. Appl. No. 09/969,516 (claims only).
U.S. Appl. No. 09/969,545 (claims only).
U.S. Appl. No. 09/969,546 (claims only).
U.S. Appl. No. 09/969,015 (claims only).
U.S. Appl. No. 09/969,022 (claims only).
U.S. Appl. No. 09/969,016 (claims only).
U.S. Appl. No. 09/969,536 (claims only).
U.S. Appl. No. 09/969,534 (claims only).
U.S. Appl. No. 09/969,018 (claims only).
U.S. Appl. No. 09/969,019 (claims only).
U.S. Appl. No. 09/970,161 (claims only).
U.S. Appl. No. 09/969,021 (claims only).
U.S. Appl. No. 09/969,027 (claims only).
U.S. Appl. No. 09/969,039 (claims only).
U.S. Appl. No. 09/969,020 (claims only).
U.S. Appl. No. 09/969,146 (claims only).
U.S. Appl. No. 09/969,024 (claims only).
"ADP CSG: Integrated Medical Solutions," ADP Claims Solutions Group, Copyright 2001, p. 1.
"IMS ICE,"ADP Integrated Medical Solutions, Copyright 2001, Rockville, MD, pp. 1-6.
"CSC Introduces Liability Assessment Tool to Improve Claims Consistency," Computer Sciences Corporation, Oct. 31, 2001, pp. 1-2.
"CSC: Solutions Search," Computer Sciences Corporation, Copyright 2001, p. 1.
"CSC Expands Cost Containment Solutions for Claims and Legal Expenses," Computer Sciences Corporation, Jun. 27, 2001, El Segundo, CA, pp. 1-2.
"@ Fault A Commitment to Consistency," Computer Sciences Corporation, Copyright 2000, pp. 1-2.
"ISO Claims Outcome Advisor," ISO Properties, Inc., Copyright 1996, 2001, Jersey City, NJ, pp. 1-2.
"Insurance Services Office Strengthens Claims Handling Team," ISO Properties, Inc., Copyright 1996, 2001, Jersey City, NJ, pp. 1-2.
Frey, Joe, "Putting a price on auto injuries: How software called Colossus evaluates your pain," Insure.com, Oct. 26, 2000, pp. 1-5.
Frey, Joe, "p. 2: Putting a price on auto injuries: How software called Colossus evaluates you pain—Allstate under colossal pressure," Insure.com, Oct. 26, 2000, pp. 1-3.
Merlin, Jr., William F., "Colossus: What We Know Today," The Merlin Law Group, Aug. 2000, Tampa, FL, pp. 1-8.
Merlin, Jr., William F., "Collision Course With The Colossus Program: How To Deal With It," The Merlin Law Group, May 2000, Tampa, FL, pp. 1-17.
Merlin, Jr., William F., "Overcoming Allstate's Trade Secrets and Work-Product Objections," Th Merlin Law Group, Mar. 2000, Tampa, FL, pp. 1-31.
"Accident Reconstruction Software Maine Computer Group," Maine Computer Group, Copyright 2001, pp. 1-2.
"REC-TEC Accident Reconstruction and Analysis Computer Software," George M. Bonnett, Nov. 2001, Rockledge, FL, pp. 1-5.

"REC-TEC Accident Reconstruction Software," George M. Bonnett, Sep. 2001, Rockledge FL, pp. 1-10.
McHenry, Brian G., "The Algorithms of Crash," Southeast Coast Collision Conference, Aug. 2001, pp. 1-34.
Mead, Jay, Technical Communication, Aug. 1998, V. 45, N. 3, p. 353-380.
Scopus Introduces World's Most Complete Call Center Solution for Financial Services; PR Newswire dated Nov. 5, 1997.
Juhl, Randy P., "The OTC Revolution"; Drugtopics.com; Mar. 3, 1997, pp. 1-9.
Borland, Russel; "Running Microsoft Outlook 97", Microsoft Press, 1997.
U.S. Patent and Trademark Office, "Communication" for U.S. Appl. No. 09/969,016 mailed Mar. 3, 2007.
U.S. Patent and Trademark Office, "Communication" for U.S. Appl. No. 09/969,018 mailed Jun. 21, 2007.
U.S. Patent and Trademark Office, "Communication" for U.S. Appl. No. 09/969,027 mailed Jun. 20, 2007.
U.S. Patent and Trademark Office, "Communication" for U.S. Appl. No. 09/969,024 mailed May 23, 2007.
U.S. Patent and Trademark Office, "Communication" for U.S. Appl. No. 10/306,866 mailed Jun. 21, 2007.
U.S. Patent and Trademark Office, "Communication" for U.S. Appl. No. 10/306,858 mailed Jun. 29, 2007.
U.S. Patent and Trademark Office, "Communication" for U.S. Appl. No. 09/969,021 mailed Mar. 8, 2007.
U.S. Patent and Trademark Office, "Communication" for U.S. Appl. No. 10/306,623 mailed Mar. 7, 2007.
Walrand, J., et al., High-Performance Communication Networks, "Economics," Chapter 8 through 8.2.1, p. 361-369, 1996 (f8).
Microsoft Component Services: Server Operating System A Technology Overview, Microsoft Corp., p. 1-7, Aug. 15, 1998 (f38).
Holding State in Objects with Microsoft Transaction Server, Microsoft Corp., pp. 2, Jun. 1997. (f37).
Straight Through Processing: Migration Assessment for Series II Clients Computer Sciences Corporation, pp. 6, 2003. (g50).
Property and Casualty Solutions: CSC's Property & Casualty Claims Solutions, Computer Sciences Corporation, pp. 2, 2003. (g51).
@Fault: Improve Claims Practices Through Greater consistency in Fault Assessment, Computer Sciences corporation, pp. 2, 2004. (g53).
Utzaeider, James, "Microsoft Transaction Server and Internet Information Server: Technology for the Web," Microsoft Corp., p. 1-5, Feb. 6, 1998. (f44).
Howarth, Brad, "Outsourcing: Technology on tap," Information Economy, BRW, vol. 21, No. 47, p. 1-5, Dec. 3, 1999. (f28).
U.S. Patent and Trademark Office, "Communication" for U.S. Appl. No. 09/969,024 mailed Jan. 31, 2006.
U.S. Patent and Trademark Office, "Communication" for U.S. Appl. No. 09/969,024 mailed Jun. 1, 2006.
U.S. Patent and Trademark Office, "Communication" for U.S. Appl. No. 09/969,022 mailed Apr. 6, 2006.
Nicolle, "Elementary, dear Holmes," Jan. 22, 1997, The Times (London, UK, p. Interfa).
Nairn, "IT and Crime Resolution, It's elementary, Holmes helps UK police solve crimes,"Jan. 3, 1997, Financial Times (London, UK), p. 17.
David, "Knowledge on the Beat," Jul. 1999, Knowledge Management Magazine, www.destinationkm.com.
U.S. Patent and Trademark Office, "Communication" for U.S. Appl. No. 09/969,015 mailed Jun. 1, 2006.
U.S. Patent and Trademark Office, "Communication" for U.S. Appl. No. 09/969,019 mailed Jun. 1, 2006.
U.S. Patent and Trademark Office, "Communication" for U.S. Appl. No. 09/969,546 mailed Mar. 21, 2006.
U.S. Patent and Trademark Office, "Communication" for U.S. Appl. No. 09/969,016 mailed Mar. 21, 2006.
U.S. Patent and Trademark Office, "Communication" for U.S. Appl. No. 09/969,018 mailed Jan. 26, 2006.
U.S. Patent and Trademark Office, "Communication" for U.S. Appl. No. 09/969,018 mailed Jun. 2, 2006.
U.S. Patent and Trademark Office, "Communication" for U.S. Appl. No. 09/969,545 mailed Mar. 23, 2006.

Laser Technology, Inc. "Crash/Crime Scene Mapping" @ http://www.lasertech.com/accidentcsinv.html. Copyright 1999.

Traynor, "The Effects of Varying Safety Conditions on the External Costs of Driving," Winter, 1994 Eastern Econiomic Journal, vol. 20 No. 1 pp. 45-60.

Baker, "Don't Throw Your Adjusters to the Lions" Apr. 1995, Best's Review, vol. 95 No. 12, pp. 66-69.

U.S. Patent and Trademark Office, "Communication" for U.S. Appl. No. 09/969,536 mailed Mar. 24, 2006.

Meckbach, "U.S. Universities pick up Ditek's CAD application" Feb. 26, 1999. Computing Canada. vol. 25, Iss. 8 p. 14.

Spice, "Police use lasers, computers to map scenes Town of Pewaukee's new system boost accuracy of reconstructions, users say" Sep. 29, 1998. Milwaukee Journal Sentinel. p. 2.

Ditek@http://www.archive.org/web/20000301124742/www.ditec.com, last viewed on Nov. 28, 2005.

U.S. Patent and Trademark Office, "Communication" for U.S. Appl. No. 09/969,516 mailed Aug. 10, 2006.

Ross, "Settled Out of Court" Copyright 1980. Aldine Degruyter.

Esters, "Computers Can Help Settle Auto Claims" Apr. 28, 1997, National Underwriter. vol. 101, Iss. 17, p. 10.

Laser Technology, Inc. "QuickMap 3D" http://web.archive.org/web/200003011511/222.lasertech.com/laserproducts/qm3d.html, last viewed on Nov 28, 2005.

U.S. Patent and Trademark Office, "Communication" for U.S. Appl. No. 09/970,161 mailed Mar. 23, 2006.

U.S. Patent and Trademark Office, "Communication" for U.S. Appl. No. 09/969,021 mailed Feb. 27, 2006.

U.S. Patent and Trademark Office, "Communication" for U.S. Appl. No. 09/969,017 mailed Mar. 1, 2006.

U.S. Patent and Trademark Office, "Communication" for U.S. Appl. No. 09/969,146 mailed Feb. 28, 2006.

U.S. Patent and Trademark Office, "Communication" for U.S. Appl. No. 09/969,027 mailed Mar. 3, 2006.

U.S. Patent and Trademark Office, "Communication" for U.S. Appl. No. 09/969,018 mailed Dec. 4, 2006.

Lindberg, Gunnar, "Calculating Transport Accident Costs: Final report of the Expert Advisors to the high Level group on Infrastructure charging (Working Group 3)." Borlaenge, Sweden. Apr. 27, 1999, 53 pages.

U.S. Patent and Trademark Office, "Office Action" for U.S. Appl. No. 09/969,019 mailed Feb. 27, 2008.

U.S. Patent and Trademark Office, "Supplemental Notice of Allowance" for U.S. Appl. No. 09/969,018 mailed Jul. 30, 2009.

U.S. Patent and Trademark Office, "Decision on Appeal" for U.S. Appl. No. 09/969,039 dated Jun. 10, 2009.

U.S. Patent and Trademark Office, "Notice of Allowability" for U.S. Appl. No. 10/306,908 mailed Jul. 27, 2009.

U.S. Patent and Trademark Office, "Office Action" for U.S. Appl. No. 10/306,866 mailed Aug. 14, 2009.

U.S. Patent and Trademark Office, "Final Office Action" for U.S. Appl. No. 10/306,873 mailed Jul. 21, 2009.

Blodgett, "Corporate Ethics Codes: A Practical Application of Liability Prevention", Journal of Business Ethics, vol. 16, Nos. 12-23, pp. 1363-1369, 1997.

Falkinham, Sara, "The 'Open and Obvious Defense' is No Longer a Complete Bar to Plaintiff Recovery", Mississippi Law Journal (Fall 1994), p. 241 (64 Miss. L.J. 241).

U.S. Patent and Trademark Office, "Final Office Action" for U.S. Appl. No. 10/306,858 mailed Dec. 13, 2007.

U.S. Patent and Trademark Office, "Final Office Action" for U.S. Appl. No. 10/306,623 mailed Jan. 25, 2008.

U.S. Patent and Trademark Office, "Final Office Action" for U.S. Appl. No. 10/238,029 mailed Dec. 13, 2007.

U.S. Patent and Trademark Office, "Office Action" for U.S. Appl. No. 09/969,020 mailed Jan. 24, 2008.

U.S. Patent and Trademark Office, "Final Office Action" for U.S. Appl. No. 09/969,021 mailed Jan. 8, 2008.

U.S. Patent and Trademark Office, "Office Action" for U.S. Appl. No. 09/969,027 mailed Jan. 11, 2008.

U.S. Patent and Trademark Office, "Office Action" for U.S. Appl. No. 10/238,019 mailed Jan. 11, 2008.

U.S. Patent and Trademark Office, "Final Office Action" U.S. Appl. No. 10/238,981 mailed Jan. 25, 2008.

U.S. Patent and Trademark Office, "Order Remanding Appeal to Examiner" for U.S. Appl. No. 09/969,534 mailed May 19, 2010.

U.S. Patent and Trademark Office, "Office Action" for U.S. Appl. No. 09/969,534 mailed Apr. 15, 2008.

U.S. Patent and Trademark Office, "Office Action" for U.S. Appl. No. 09/969,019 mailed Apr. 28, 2008.

U.S. Patent and Trademark Office, "Examiner' Answer" for U.S. Appl. No. 09/969,146 mailed Oct. 5, 2007.

U.S. Patent and Trademark Office, "Final Office Action" for U.S. Appl. No. 10/238,029 mailed Dec. 13, 2007.

U.S. Patent and Trademark Office, "Office Action" for U.S. Appl. No. 10/238,029 mailed May 12, 2008.

U.S. Patent and Trademark Office, "Final Office Action" for U.S. Appl. No. 10/306,864 mailed Mar. 27, 2008.

U.S. Patent and Trademark Office, "Final Office Action" for U.S. Appl. No. 10/306,908 mailed Mar. 21, 2008.

U.S. Patent and Trademark Office, "Final Office Action" for U.S. Appl. No. 10/306,804 mailed Mar. 21, 2008.

U.S. Patent and Trademark Office, "Final Office Action" for U.S. Appl. No. 10/306,866 mailed May 5, 2008.

U.S. Patent and Trademark Office, "Final Office Action" for U.S. Appl. No. 10/306,628 mailed Mar. 27, 2008.

U.S. Patent and Trademark Office, "Final Office Action" for U.S. Appl. No. 10/306,873 mailed May 21, 2008.

U.S. Patent and Trademark Office, "Final Office Action" for U.S. Appl. No. 10/306,909 mailed May 14, 2008.

U.S. Patent and Trademark Office, "Final Office Action" for U.S. Appl. No. 10/306,803 mailed May 29, 2008.

U.S. Patent and Trademark Office, "Examiner's Answer" for U.S. Appl. No. 09/969,018 mailed Jul. 21, 2008.

U.S. Patent and Trademark Office, "Final Office Action" for U.S. Appl. No. 09/969,027 mailed Jul. 10, 2008.

U.S. Patent and Trademark Office, "Final Office Action" for U.S. Appl. No. 09/969,020 mailed Jul. 7, 2008.

U.S. Patent and Trademark Office, "Office Action" for U.S. Appl. No. 10/238,025 mailed Jun. 27, 2008.

U.S. Patent and Trademark Office, "Office Action" for U.S. Appl. No. 10/237,547 mailed Jun. 30, 2008.

U.S. Patent and Trademark Office, "Office Action" for U.S. Appl. No. 10/238,981 mailed Aug. 1, 2008.

U.S. Patent and Trademark Office, "Office Action" for U.S. Appl. No. 10/306,858 mailed Jul. 18, 2008.

U.S. Patent and Trademark Office, "Office Action" for U.S. Appl. No. 10/790,632 mailed Jul. 2, 2008.

U.S. Patent and Trademark Office, "Final Office Action" for U.S. Appl. No. 10/238,019 mailed Sep. 23, 2008.

U.S. Patent and Trademark Office, "Notice of Allowance" for U.S. Appl. No. 10/238,019 mailed Nov. 13, 2009.

U.S. Patent and Trademark Office, "Notice of Allowance" for U.S. Appl. No. 10/306,804 mailed Nov. 9, 2009.

U.S. Patent and Trademark Office, "Office Action" for U.S. Appl. No. 10/790,626 mailed Nov. 25, 2009.

U.S. Patent and Trademark Office, "Decision on Appeal" for U.S. Appl. No. 09/969,146 mailed Mar. 26, 2010.

U.S. Patent and Trademark Office, "Final Office Action" for U.S. Appl. No. 10/237,547 mailed Mar. 31, 2010.

U.S. Patent and Trademark Office, "Notice of Allowance" for U.S. Appl. No. 10/306,866 mailed Mar. 23, 2010.

U.S. Patent and Trademark Office, "Office Action" for U.S. Appl. No. 09/969,146 mailed Apr. 2, 20010.

U.S. Patent and Trademark Office, "Notice of Allowance" for U.S. Appl. No. 10/306,909 mailed Apr. 5, 2010.

U.S. Patent and Trademark Office, "Notice of Allowance" for U.S. Appl. No. 10/306,623 mailed Apr. 19, 2010.

U.S. Patent and Trademark Office, "Office Action" for U.S. Appl. No. 09/969,516 mailed Jun. 8, 2010.

U.S. Patent and Trademark Office, "Notice of Allowance" for U.S. Appl. No. 10/306,803 mailed Jun. 4, 2010.

U.S. Patent and Trademark Office, "Office Action" for U.S. Appl. No. 09/969,536 mailed Jun. 9, 2010.

U.S. Patent and Trademark Office, "Communication" for U.S. Appl. No. 09/969,020 mailed Jul. 5, 2007.
U.S. Patent and Trademark Office, "Office Action" for U.S. Appl. No. 10/306,873 mailed Sep. 20, 2007.
U.S. Patent and Trademark Office, "Final Office Action" for U.S. Appl. No. 10/306,804 mailed Oct. 3, 2007.
U.S. Patent and Trademark Office, "Final Office Action" for U.S. Appl. No. 10/306,804 mailed Oct. 3, 2007.
U.S. Patent and Trademark Office, "Office Action" for U.S. Appl. No. 10/306,803 mailed Oct. 5, 2007.
U.S. Patent and Trademark Office, "Office Action" for U.S. Appl. No. 10/306,908 mailed Oct. 4, 2007.
U.S. Patent and Trademark Office, "Office Action" for U.S. Appl. No. 10/306,864 mailed Oct. 4, 2007.
Harts, "Reel to Real: Should You believe What You See?" Defense Counsel Journal, Oct. 1999, vol. 66. p. 514 from the Dialog File ABI/Inform Global.
Malloy, "'Big Time' Match Frame May Be Small, but It has No Problems Working With the Big Boys", San Antonio Business Journal, vol. 5 No. 11, s1, p. aa, Mar. 15, 1999. Dialog ID No. 0205483 from Dialog File 635 (Business Dateline .RTM.).
U.S. Patent and Trademark Office, "Examiner's Answer" for U.S. Appl. No. 09/969,545 mailed Sep. 4, 2007.
U.S. Patent and Trademark Office, "Office Action" for U.S. Appl. No. 10/306,628 mailed Oct. 10, 2007.
U.S. Patent and Trademark Office, "Office Action" for U.S. Appl. No. 10/239,029 mailed Jun. 29, 2007.
Kahn, "The Premise Behind Premises Liability" Feb. 1994, Security Management, vol. 38, Iss. 2 pp. 61-63.
CIGNA P&C Opens National Premises Liability Center, Mar. 1999, PR Newswire, p. 1.
U.S. Patent and Trademark Office, "Final Office Action" for U.S. Appl. No. 09/969,516 mailed Nov. 14, 2007.
U.S. Patent and Trademark Office, "Final Office Action" for U.S. Application No. 09/969,016 mailed Mar. 17, 2008.
U.S. Patent and Trademark Office, "Decision to Appeal" for U.S. Appl. No. 09/969,016 mailed Mar. 26, 2010.
U.S. Patent and Trademark Office, "Notice of Allowance" for U.S. Appl. No. 09/969,016 mailed Apr. 9, 2010.
U.S. Patent and Trademark Office, "Communication" for U.S. Appl. No. 09/969,021 mailed Sep. 4, 2008.
U.S. Patent and Trademark Office, "Communication" for U.S. Appl. No. 10/306,628 mailed Aug. 22, 2008.
U.S. Patent and Trademark Office, "Communication" for U.S. Appl. No. 10/306,864 mailed Aug. 22, 2008.
U.S. Patent and Trademark Office, "Communication" for U.S. Appl. No. 10/306,873 mailed Sep. 23, 2008.
U.S. Patent and Trademark Office, "Communication" for U.S. Appl. No. 10/306,804 mailed Sep. 2, 2008.
U.S. Patent and Trademark Office "Communication" for U.S. Appl. No. 09/969,516 mailed Oct. 14, 2008.
U.S. Patent and Trademark Office, "Communication" for U.S. Appl. No. 09/969,024 mailed Jan. 9, 2009.
U.S. Patent and Trademark Office, "Examiner's Answer" for U.S. Appl. No. 09/969,016 mailed Oct. 28, 2008.
U.S. Patent and Trademark Office, "Communication" for U.S. Appl. No. 09/969,545 mailed Dec. 9, 2008.
U.S. Patent and Trademark Office, "Communication" for U.S. Appl. No. 09/969,015 mailed Dec. 9, 2008.
U.S. Patent and Trademark Office, "Communication" for U.S. Appl. No. 09/969,022 mailed Dec. 9, 2008.
U.S. Patent and Trademark Office, "Communication" for U.S. Appl. No. 09/969,536 mailed Dec. 4, 2008.
U.S. Patent and Trademark Office, "Communication" for U.S. Appl. No. 09/969,019 mailed Dec. 9, 2008.
U.S. Patent and Trademark Office, "Communication" for U.S. Appl. No. 09/970,161 mailed Dec. 9, 2008.
U.S. Patent and Trademark Office, "Communication" for U.S. Appl. No. 09/969,039 mailed Dec. 9, 2008.
U.S. Patent and Trademark Office, "Communication" for U.S. Appl. No. 10/238,029 mailed Dec. 5, 2008.
U.S. Patent and Trademark Office, "Communication" for U.S. Appl. No. 10/306,909 mailed Dec. 15, 2008.
U.S. Patent and Trademark Office, "Communication" for U.S. Appl. No. 10/306,803 mailed Dec. 12, 2008.
U.S. Patent and Trademark Office, "Communication" for U.S. Appl. No. 10/306,908 mailed Dec. 9, 2008.
U.S. Patent and Trademark Office, "Communication" for U.S. Appl. No. 10/306,866 mailed Dec. 9, 2008.
U.S. Patent and Trademark Office, "Communication" for U.S. Appl. No. 09/969,534 mailed Dec. 9, 2008.
U.S. Patent and Trademark Office, "Communication" for U.S. Appl. No. 10/306,864 mailed Jan. 8, 2009.
U.S. Patent and Trademark Office, "Communication" for U.S. Appl. No. 10/790,632 mailed Dec. 23, 2008.
U.S. Patent and Trademark Office, "Communication" for U.S. Appl. No. 10/790,626 mailed Jan. 22, 2009.
Ivanovich, Michael G., "How the Web Works—Part 1." Heating, Piping, and Air Conditioning. Feb. 1997, vol. 69 p. 82.
U.S. Patent and Trademark Office, "Communication" for U.S. Appl. No. 09/969,546 mailed Feb. 20, 2009.
U.S. Patent and Trademark Office, "Communication" for U.S. Appl. No. 10/238,029 mailed Dec. 8, 2008.
U.S. Patent and Trademark Office, "Communication" for U.S. Appl. No. 09/969,018 mailed Mar. 19, 2009.
U.S. Patent and Trademark Office, "Communication" for U.S. Appl. No. 10/306,623 mailed Jan. 7, 2009.
U.S. Patent and Trademark Office, "Communication" for U.S. Appl. No. 09/969,021 mailed Mar. 17, 2009.
U.S. Patent and Trademark Office, "Communication" for U.S. Appl. No. 10/306,908 mailed Mar. 19, 2009.
U.S. Patent and Trademark Office, "Notice of Allowance" for U.S. Appl. No. 10/306,873 mailed Dec. 14, 2009.
U.S. Patent and Trademark Office, "Notice of Allowance" for U.S. Appl. No. 10/306,864 mailed Dec. 21, 2009.
U.S. Patent and Trademark Office, "Notice of Allowance" for U.S. Appl. No. 09/969,015 mailed Dec. 31, 2009.
U.S. Patent and Trademark Office, "Notice of Allowance" for U.S. Appl. No. 09/969,019 mailed Dec. 31, 2009.
U.S. Patent and Trademark Office, "Final Office Action" for U.S. Appl. No. 10/238,025 mailed Dec. 31, 2009.
U.S. Patent and Trademark Office, "Decision on Appeal" for U.S. Appl. No. 09/969,146 mailed Jan. 15, 2010.
U.S. Patent and Trademark Office, "Final Office Action" for U.S. Appl. No. 10/912,883 mailed Jan. 25, 2010.
U.S. Patent and Trademark Office, "Notice of Allowance" for U.S. Appl. No. 09/969,022 mailed Jan. 29, 2010.
U.S. Patent and Trademark Office, "Notice of Allowance" for U.S. Appl. No. 09/970,161 mailed Jan. 29, 2010.
U.S. Patent and Trademark Office, "Notice of Allowance" for U.S. Appl. No. 09/969,021 mailed Feb. 4, 2010.
U.S. Patent and Trademark Office, "Final Office Action" for U.S. Appl. No. 09/969,536 mailed Oct. 16, 2009.
U.S. Patent and Trademark Office, "Advisory Action" for U.S. Appl. No. 09/969,020 mailed Oct. 21, 2009.
U.S. Patent and Trademark Office, "Office Action" (Restriction Requirement) for U.S. Appl. No. 10/238,025 mailed Oct. 16, 2009.
U.S. Patent and Trademark Office, "Notice of Allowance" for U.S. Appl. No. 10/238,981 mailed Oct. 7, 2009.
U.S. Patent and Trademark Office, "Office Action" for U.S. Appl. No. 10/306,909 mailed Oct. 5, 2009.
U.S. Patent and Trademark Office, "Office Action" for U.S. Appl. No. 10/306,623 mailed Oct. 22, 2009.
U.S. Patent and Trademark Office, "Office Action" for U.S. Appl. No. 10/306,803 mailed Oct. 5, 2009.
U.S. Patent and Trademark Office, "Notice of Allowability" for U.S. Appl. No. 10/306,908 mailed Sep. 21, 2009.
U.S. Patent and Trademark Office, "Office Action" for U.S. Appl. No. 10/306,628 mailed Oct. 1, 2009.
U.S. Patent and Trademark Office, "Final Office Action" for U.S. Appl. No. 10/790,632 mailed Oct. 20, 2009.
U.S. Patent and Trademark Office, "Notice of Allowance" for U.S. Appl. No. 09/969,039 dated Oct. 9, 2009.
U.S. Patent and Trademark Office, "Office Action" for U.S. Appl. No. 09/969,015 mailed Oct. 27, 2009.

U.S. Patent and Trademark Office, "Office Action" for U.S. Appl. No. 09/969,022 mailed Oct. 27, 2009.
U.S. Patent and Trademark Office, "Office Action" for U.S. Appl. No. 09/969,019 mailed Oct. 27, 2009.
U.S. Patent and Trademark Office, "Office Action" for U.S. Appl. No. 09/970,161 mailed Oct. 28, 2009.
U.S. Patent and Trademark Office, "Notice of Allowance" for U.S. Appl. No. 09/969,546 mailed Jun. 22, 2009.
U.S. Patent and Trademark Office, "Office Action" for U.S. Appl. No. 09/969,015 mailed Apr. 28, 2009.
U.S. Patent and Trademark Office, "Office Action" for U.S. Appl. No. 09/969,022 mailed Apr. 28, 2009.
U.S. Patent and Trademark Office, "Advisory Action" for U.S. Appl. No. 09/969,534 mailed Apr. 29, 2009.
U.S. Patent and Trademark Office, "Notice of Allowance" for U.S. Appl. No. 09/969,018 mailed Jun. 29, 2009.
U.S. Patent and Trademark Office, "Office Action" for U.S. Appl. No. 09/969,019 mailed Apr. 28, 2009.
U.S. Patent and Trademark Office, "Office Action" for U.S. Appl. No. 09/970,161 mailed Apr. 28, 2009.
U.S. Patent and Trademark Office, "Examiner's Answer" for U.S. Appl. No. 09/969,027 mailed Jun. 8, 2009.
U.S. Patent and Trademark Office, "Office Action" for U.S. Appl. No. 10/238,029 mailed Apr. 10, 2009.
U.S. Patent and Trademark Office, "Office Action" for U.S. Appl. No. 10/238,019 mailed Jun. 26, 2009.
U.S. Patent and Trademark Office, "Office Action" for U.S. Appl. No. 10/306,864 mailed Jun. 26, 2009.
U.S. Patent and Trademark Office, "Final Office Action" for U.S. Appl. No. 10/306,909 mailed Apr. 29, 2009.
U.S. Patent and Trademark Office, "Final Office Action" for U.S. Appl. No. 10/306,803 mailed Apr. 29, 2009.
U.S. Patent and Trademark Office, "Office Action" for U.S. Appl. No. 10/306,804 mailed May 26, 2009.
U.S. Patent and Trademark Office, "Final Office Action" for U.S. Appl. No. 10/306,866 mailed Apr. 16, 2009.
U.S. Patent and Trademark Office, "Final Office Action" for U.S. Appl. No. 10/306,858 mailed Apr. 2, 2009.
U.S. Patent and Trademark Office, "Final Office Action" for U.S. Appl. No. 10/306,628 mailed May 7, 2009.
U.S. Patent and Trademark Office, "Office Action" for U.S. Appl. No. 10/790,632 mailed May 22, 2009.
U.S. Patent and Trademark Office, "Office Action" for U.S. Appl. No. 10/790,626 mailed Jun. 24, 2009.
U.S. Patent and Trademark Office, "Office Action" for U.S. Appl. No. 10/912,883 mailed Jun. 25, 2009.
North Carolina Cooperative Extension Service, "Liability and the North Carolina Landowner." Oct. 9, 1995.
Clark, Walter, "The Investigation and Adjustment of Liability" 1914.
Taanaim, "Babylonian Talmud: Tractate Baba Kamma-47a and 47b" 500CE.
Sayed, "Assault on the Common Law of Premise Liability: What duty of care does an owner or occupier of land owe to a police officer who enters the premises of another by authority of law." Spring 1997, 19 Campbell Law Review 579.
Wiedmann, "Technical parameters influencing the severity of injury front-seat, beltprotected car passengers on the impact side in car-to-car side collisions with the main impact between the front and rear seats (B-pillars)", International Journal of Legal Medicine (Germany); 1992; p. 105(1) p. 11-5, ISSN 0937-9827.
NexGen Ergonomics, Mannequin Pro, Jun. 20, 2002.
U.S. Patent and Trademark Office, "Final Office Action" for U.S. Appl. No. 10/238,981 mailed Apr. 13, 2009.
U.S. Patent and Trademark Office, "Notice of Allowance" for U.S. Appl. No. 09/969,516 mailed Oct. 14, 2010.
U.S. Patent and Trademark Office, "Notice of Allowance" for U.S. Appl. No. 09/969,536 mailed Oct. 14, 2010.

* cited by examiner

Roadway Configuration

| Accident Type | A | B | C | D | E | F | G | H | I | FG |
|---|---|---|---|---|---|---|---|---|---|---|
| 1 | Y | Y | Y | Y | Y | Y | Y | Y | Y | Y |
| 2 | N | Y | Y | N | N | N | N | Y | N | N |
| 3 | N | Y | Y | N | N | N | N | N | Y | N |
| 4 | N | Y | Y | Y | N | N | N | Y | N | N |
| 5 | N | Y | Y | N | N | N | N | N | N | N |
| 6 | N | Y | Y | N | N | Y | N | Y | N | Y |
| 7 | N | Y | N | N | N | Y | N | Y | N | Y |
| 8 | Y | Y | Y | N | Y | N | N | Y | N | N |
| 9 | Y | Y | Y | Y | Y | N | N | N | Y | N |
| 10 | Y | Y | Y | Y | Y | N | N | N | Y | N |
| 11 | Y | Y | Y | N | Y | N | N | Y | Y | N |
| 12 | Y | Y | Y | Y | Y | N | N | Y | Y | N |
| 13 | Y | Y | Y | Y | Y | N | N | Y | Y | N |
| 14 | Y | Y | Y | Y | Y | Y | Y | Y | Y | Y |
| 15 | Y | Y | Y | Y | Y | Y | Y | Y | Y | Y |
| 16 | Y | Y | Y | N | Y | Y | N | Y | N | Y |
| 17 | N | Y | N | N | N | Y | Y | N | N | Y |

*FIG. 6*

| Accident Type - Roadway Configuration | Impact Groups | | | |
|---|---|---|---|---|
| 1H-A behind B | A811B805, A811B806, A811B807, A812B805, A812B806, A812B807, A801B805, A801B806, A801B807, A802B807, A803B807, A804 B807, A808B805, A809B805, A810B805 | | | |
| 1I-A behind B | A811B805, A811B806, A811B807, A812B805, A812B806, A812B807, A801B805, A801B806, A801B807, A802B807, A803B807, A804 B807, A808B805, A809B805, A810B805 | | | |
| 2B-4 way intersect w/A from top turning left and B from bottom going straight | A811B809, A811B810, A810B808 | A811B811, A812B811, A801B811, A801B812, A801B812, | A802B801, A803B812, A803B801 | A804B812, A804B801 |
| 2C-T intersect to right w/A turning left from top and B from bottom going straight | A811B809, A811B810, A810B808 | A811B811, A812B811, A801B811, A801B812, A802B812 | A802B801, A803B812, A803B801 | A804B812, A804B801 |
| 2H- center turn lane w/A turning left and B going straight | A811B809, A811B810, A810B808 | A811B811, A812B811, A801B811, A801B812, A802B812 | A802B801, A803B812, A803B801 | A804B812, A804B801 |
| 3B- 4- way intersect w/A going straight from left and B going straight from bottom | A811B808, A812B808, A801B808, A811B809, A812B809 | A811B810, A812B810, A801B809, A801B810 | A802B811, A802B812, A802B801, A803B811 | A803B812, A803B801, A804B811, A804B812, A804B801 |

*FIG. 8b*

Insured

| Factor | Penalty (%) | Situational Weight | % weight | applies | adjusted penalty (%) |
|---|---|---|---|---|---|
| 1. Alcohol/Drugs | 15 | High | 150 | YES | 22.5 |
| 2. Headlights Off | 5 | *Normal* | 100 | YES | 5 |
| 3. Inattention | 10 | Low | 50 | NO | 0 |
| ... | | | | | |
| 19. Faulty equipment | 10 | N/A | 0 | YES | 0 |

Claimant

| Factor | Penalty (%) | Situational Weight | % weight | applies | adjusted penalty (%) |
|---|---|---|---|---|---|
| 1. Alcohol/Drugs | 15 | High | 150 | NO | 0 |
| 2. Headlights Off | 5 | *High* | 150 | YES | 7.5 |
| 3. Inattention | 10 | Low | 50 | NO | 0 |
| ... | | | | | |
| 10. Speed | 15 | Low | 50 | YES | 7.5 |

*FIG. 9a*

|  | First Party | Second Party |
|---|---|---|
| Base Liability | 50% | 50% |
| Factor 1 | +10% | -10% |
| Factor 2 | +15% | -15% |
| Factor 3 | -5% | +5% |
| Total Liability | 70% | 30% |

*Fig. 9b*

|  | First Party | Second Party |
|---|---|---|
| Base Liability | 50% | 50% |
| Factor 1 | +10% | -10% |
| Factor 2 | +15% | -15% |
| Factor 3 | -5% | +5% |
| Sum of Effects | +20% | -20% |
| Total Liability | 60% | 40% |

*Fig. 9c*

| Speed | Surface | Condition | Number of car lengths |
|---|---|---|---|
| <= 45 | Not gravel | Dry | < 10% speed |
| | | Wet | < 20% speed |
| | | Muddy | < 20% speed |
| | | Plowed snow | < 30% speed |
| | | Snow Ice Patch | < 30% speed |
| | | Snow Ice | < 60% speed |
| | Gravel | Any | < 20% speed |
| > 45 | Not gravel | Dry | < 15% speed |
| | | Wet | < 30% speed |
| | | Muddy | < 30% speed |
| | | Plowed snow | < 45% speed |
| | | Snow Ice Patch | < 45% speed |
| | | Snow Ice | < 90% speed |
| | Gravel | Any | < 30% speed |

Max. Safe Speed = Speed Limit (SL) - Road Condition reduction - Weather reduction
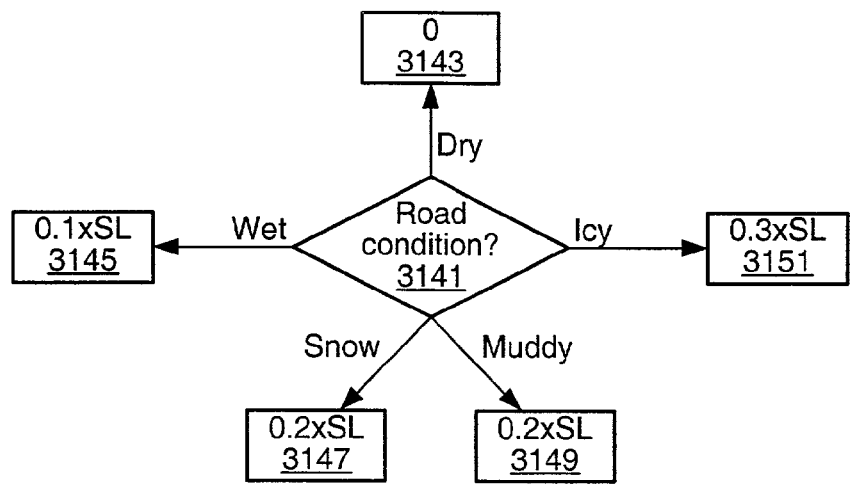
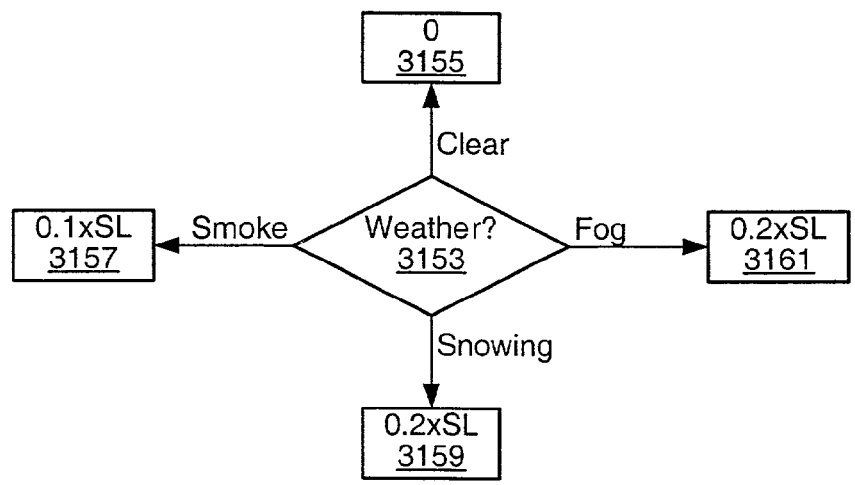
FIG. 31b

| Safe Speed (mph) | Actual Speed (mph) | Threshold distance for close or far (ft) | Close % (<=threshold) (ft) | Far % (>=threshold) (ft) |
|---|---|---|---|---|
| 50 | 50-60<br>61-70<br>71-80<br>81-90<br>91-100+ | 100<br>150<br>200<br>300<br>N/A | 0<br>30<br>40<br>70 ALV<br>100 ALV | 0<br>10<br>20<br>50 ALV<br>100 ALV |
| 25 | 25-27<br>28-30<br>31-35<br>36-40<br>41-45<br>46-50<br>51-60 | 50<br><br><br>80<br><br><br>130 | 0<br>10<br>30<br>70 ALV<br>70 ALV<br>70 ALV<br>100 ALV | 0<br>0<br>20<br>50<br>50 ALV<br>50 ALV<br>100 ALV |

*FIG. 31c*

| Road Condition | Category | Safe speed as percent of speed limit |
|---|---|---|
| Dry | A | 100% |
| Wet | B | 90% |
| Accumulated water | C | 55% |
| Muddy | C | 55% |
| Blowing snow- no accumulation | A | 100% |
| Accumulated snow | C | 55% |
| Hardpacked snow | D | 45% |
| Ice patches | D | 45% |
| Ice | E | 15% |
| Black ice | F | 45% |

FIG. 32a

| Safe Speed (pick a row based on this) | Actual Speed (pick smaller row) | Threshold distance for close or far | Close % (distance in ft. <=threshold) | Far % (> threshold) |
|---|---|---|---|---|
| Over 35 | <61<br>61-70<br>71-80<br>81-90<br>91+ | 100<br>150<br>200<br>300<br>N/A | N/A<br>30<br>40<br>70 ALV<br>100 ALV | N/A<br>10<br>20<br>50 ALV<br>100 ALV |
| 20 to 35 | <28<br>28-30<br>31-35<br>36-40<br>41-45<br>46-50<br>51+ | 50<br>50<br>50<br>80<br>80<br>80<br>130 | N/A<br>10<br>30<br>70 ALV<br>70 ALV<br>70 ALV<br>100 ALV | N/A<br>N/A<br>20<br>50<br>50 ALV<br>50 ALV<br>100 ALV |

FIG. 32c

| Question | Conclusion based on these answers | |
|---|---|---|
| | Violation | Violation and citation |
| Cones / barricade | 2100 | 2101 |
| Do not enter | 2102 | 2103 |
| Left turn only | 2104 | 2105 |
| Solid yellow / white line marking | 2106 | 2107 |
| No right turn on red | 2108 | 2109 |
| No stopping | 2110 | 2111 |
| No U-turn | 2112 | 2113 |
| Right turn only | 2114 | 2115 |
| Straight only | 2116 | 2117 |
| One way only | 2118 | 2119 |
| No parking zone | 2120 | 2121 |
| No passing zone | 2122 | 2123 |

| A | Factors | B |
|---|---|---|
| N/A | Following too closely | N/A |
| Low | Alcohol / Drugs / Rx | Low |
| High | Headlights off (night) | High |
| Low | Driver inattention | Low |
| Low | Speed | High |
| Low | Animal / pedestrian / other vehicle action | Low |
| N/A | Sudden stop | N/A |
| N/A | Brakelights not on | N/A |
| N/A | Backing unsafely | N/A |
| Low | Failure to take evasive action | Low |
| N/A | Opened door into traffic lane | N/A |
| High | Driver illness / physical disability | High |
| N/A | Improper lane change | N/A |
| N/A | Improper turn | Low |
| Low | Weather (visibility and traction) | N/A |
| Low | Debris | N/A |
| Low | Road defect | Low |
| High | Defective traffic control | High |
| High | Faulty equipment (may shift to 3d party) | High |

Manual Assessment

For the reasons stated below, @Fault did not compute a fault assessment. Therefore, you will need to do so. Please answer the question below.

What is the percentage of fault for both parties?

Insured — 5403
Claimant — 5405

Manual Assessment reason(s):

This combination of impact points requires a manual assessment. When possible, using impact points 812 and 806 for front and rear impacts, 803 and 809 for side impacts and 801, 811, 805, and 807 for angled impacts. — 5407

<< Previous    Next >>

COMPUTERIZED METHOD AND SYSTEM OF DETERMINING RIGHT OF WAY AND LIABILITY FOR AN ACCIDENT

PRIORITY CLAIM

This application claims priority to U.S. Provisional Application No. 60/237,744 entitled "Computerized Method of Liability Assessment for a Motor Vehicle Accident," filed Oct. 2, 2000.

BACKGROUND OF THE INVENTION

1. Field of the Invention

The present invention generally relates to estimation of liability in an accident. Certain embodiments relate to computer-implemented systems and methods for estimating liability in a motor vehicle accident through analysis of characteristics of motor vehicle accidents.

2. Description of the Related Art

A typical motor vehicle accident claims organization may face a number of challenges in processing claims. Some of these challenges may include assessment of liability, threat of litigation, and experience level of claims adjusters. A motor vehicle accident claims organization may add value to the liability assessment process by producing a solution that enhances the liability assessment process and increases the effectiveness of the claims adjuster.

Assessment of liability is one important challenge facing a claims organization. It is believed that a large percentage of motor vehicle accident claims may be assessed at 100% liability against the insured when the claimant may actually share in the fault. While it may be difficult to pinpoint exact reasons for this practice among claims adjusters, several factors influencing the tendency to assess 100% liability against the insured may include, but are not limited to, ineffective negotiation, large case loads, inadequate time to effectively assess liability, and a desire to settle claims quickly to avoid litigation.

Considering the litigious nature of claimants, and the presence of claimant counsel during negotiations, claims adjusters may need to rigorously investigate characteristics of a motor vehicle accident scene, duties of the insured, and contributing actions of the claimant before assessing liability.

The experience level of claims adjusters may typically be low due to a lack of longevity in such a position. Over the years, a dramatic shortening of the training regimen for most new claims adjusters may reduce the effectiveness of claims adjusters. In addition, the lack of experienced claims adjusters available to advise and teach new claims adjusters worsens the situation. Furthermore, new claims adjusters may not be as knowledgeable in claims adjusting practices and the laws of their jurisdiction, as are senior claims adjusters, and consequently they may make "best guess" assessments. Therefore, a lack of trained and experienced claims adjusters may tend to produce an inadequate and/or inequitable assessment process.

Accordingly, it may be advantageous to provide a system and method to assess fault or liability in motor vehicle accidents by relying on expert knowledge collected from experienced claims adjusters regarding the influence of multiple characteristics of a motor vehicle accident proportional to the liability of the claimant and the insured.

SUMMARY OF THE INVENTION

An embodiment of the present invention relates to a computer-implemented method for estimating liability in an accident.

In one embodiment, liability estimation in a vehicle accident may be based on multiple characteristics that describe the accident. Characteristics that describe either a real, a past, or a theoretical accident may include but are not limited to, roadway configuration, accident type, traffic controls at the vehicle accident scene, right of way, and impact points of each motor vehicle. The right of way may be established from real characteristics of a vehicle accident and questions about the real characteristics. At least one of the real characteristics may include: roadway configuration, accident type, right of way, or traffic control. Alternatively, a claims adjuster may specify the right of way.

The real set of characteristics may be compared to past or theoretical characteristics to determine a set of matching characteristics. The liability for the real accident may be based on an estimate of liability associated with the matching set of past or theoretical characteristics. The estimated liability for the real accident determined in this way may be a base liability.

The liabilities associated with the characteristics of the past or theoretical accident may be associated with an impact group in addition to other characteristics of a real accident. An impact group may include a pair of impact points for a past or theoretical accident. A pair of impact points may include an impact point for each of two vehicles involved in an accident. Each pair of impact points may be associated with two values of base liability: a lower bound of liability and an upper bound of liability. One set of values may correspond to one vehicle with the right of way, and the other set of values may correspond to the other vehicle having the right of way. Each of the pairs of impact points in a given impact group may have the same base liability and lower and upper bound of liability.

Effects on the liability due to factors specific to the vehicle, driver, and environment may be taken into account by identifying specific factors that may be relevant to the real accident. Factors for past or theoretical accidents may be associated with estimates of a contribution to liability. An estimate of the contribution of the factors to liability in the real accident may be determined by associating the factors relevant to the real accident with the estimates of the contribution of the factors for the past or theoretical accidents.

The contribution of the factors to the liability may also be adjusted. The adjustments may take into account sets of characteristics corresponding to the real accident and/or the preference of a claims organization. A situational weight (i.e., an adjustment related to the characteristics of a specific accident) may be based on knowledge obtained from experienced claims adjusters. Alternatively, the situational weight may be inferred from answers to a series of questions relating to the factor and accident.

The individual factors may be adjusted by a ranking factor that accounts for the preference of the claims organization. Furthermore, the sum of the contribution of the factors to liability may be adjusted by a factor influence that may also account for the preference of a claims organization.

The contribution of a factor may be so significant that it may be necessary to perform a further adjustment. Such a factor may adjust the liability beyond the lower and upper bounds defined for the liability. The contribution of the factor may be ignored and an absolute liability value may be assigned to be the liability estimate.

The liability might be expressed as a range rather than a single value. The range may be created using a range radius. The range radius may be a percentage value that may be added to and subtracted from the final liability to create the range.

A knowledge acquisition utility may be used to determine impact groups for a given set of characteristics of a past or theoretical accident. An impact group may be a collection of pairs of impact points. Each of the pairs of impact points in the impact group may have the same liability and lower and upper bounds of liability. Experienced claims adjusters may use the knowledge acquisition utility to determine the number of impact groups for each set of characteristics and the impact point pairs in each impact group.

A claims organization may employ experienced claims adjusters to use a tuning utility to estimate characteristics and properties of past or theoretical accidents such as base liabilities and lower and upper bounds of liabilities. Characteristics and properties may be entered into a knowledge acquisition utility associated with the tuning utility. The user may then run pre-configured test scenarios, analyze the results, and refine the characteristics and properties as necessary. The procedure may be repeated until the user is satisfied.

A computer-implemented method for estimating liability in a vehicle accident may include several steps. The user may provide to a computer system claim data regarding the vehicle accident in a graphical user interface. The user may provide to a computer system data for each vehicle involved in a vehicle accident. The user may provide data regarding characteristics of the vehicle accident. To assist the user in providing data regarding characteristics of the vehicle accident, the computer system may display graphical representations of the characteristics such as the roadway configurations, accident types, and impact points. The user may identify discords within the entered data. The user may determine a most likely set of characteristics associated with the real accident. As needed, the user may consult a legal reference system to determine legal information specific to the jurisdiction in which the accident occurred. The user may be provided with an assessment report that summarizes the estimate of liability, data used to determine the estimate, and negotiating points regarding the estimate.

The assessment of liability in a vehicle accident may involve analysis of multiple statements of the description of an accident. In one embodiment, the consistency between different witness statements may be assessed. A graphical user interface used for estimating liability may be used to collect information from witness statements. The computer system may compare details given in each witness description. The system may present the results of the comparison in tabular form, listing for each party, its version of the detail described. Details with inconsistent versions may be noted in the tabulation of results.

In one embodiment for analysis of witness statements, a graphical user interface for estimating liability may be combined with accident reconstruction methodology to assess the credibility of details in witness accident descriptions. Accident reconstruction software may be applied to determine details relating to speed, time, and distance of the vehicles involved in the accident. The credibility of a witness statement may be evaluated according to its consistency with the results of the accident reconstruction software.

In one embodiment, a graphical user interface for estimating liability may be combined with a credibility assessment method to create a reliable accident description. The details relevant to the accident may be tested by a credibility assessment method such as accident reconstruction software. The most credible version of the details may then be combined into a single, reliable version of an accident description.

BRIEF DESCRIPTION OF THE DRAWINGS

A better understanding of the present invention may be obtained when the following detailed description of preferred embodiments is considered in conjunction with the following drawings, in which:

FIG. 6 is a roadway configuration/accident type matrix of applicability according to one embodiment;

FIG. 8b is a table of impact groups for roadway configuration/accident type combinations according to one embodiment;

FIG. 9a includes tables illustrating a first method of assessing the contribution of factors to the liability according to one embodiment;

FIG. 9b includes a table illustrating a second method of assessing the contribution of factors to the liability according to one embodiment;

FIG. 9c includes a table illustrating a third method of assessing the contribution of factors to the liability according to one embodiment;

FIG. 31b is a flowchart for estimating the maximum safe speed for given road and weather conditions according to the first embodiment;

FIG. 31c is a table illustrating the contribution of speed to a motor vehicle accident according to the first embodiment;

FIG. 32a is a flowchart for estimating the contribution of speed to liability in a motor vehicle accident according to a second embodiment;

FIG. 32c is a table illustrating the contribution of speed to a motor vehicle accident according to the second embodiment;

FIG. 38 is a screen shot of a window from a Knowledge Acquisition utility or tuning utility for selecting a roadway configuration/accident type combination according to one embodiment;

FIG. 39 is a screen shot of an editing combination window from a Knowledge Acquisition utility or tuning utility according to one embodiment;

FIG. 40 is a screen shot of a window for editing the estimate effect of a factor according to one embodiment;

FIG. 43 is a screen shot of a Vehicle Information frame according to one embodiment;

FIG. 44 is a screen shot of an Additional Information frame according to one embodiment;

FIG. 45 is a screen shot of a Parties Information frame according to one embodiment;

FIG. 49 is a screen shot of a Impact Points data frame according to one embodiment;

FIG. 50 is a screen shot of a Discords Report frame according to one embodiment;

FIG. 51 is a screen shot of a Factors Input frame according to one embodiment;

FIG. 52 is a screen shot of a Conflict Identification frame according to one embodiment;

FIG. 53 is a screen shot of a Review frame according to one embodiment;

FIG. 54 is a screen shot of a Manual Assessment window according to one embodiment; and FIG. 55 is a screen shot of the Consultation Report window according to one embodiment.

Figure 1:
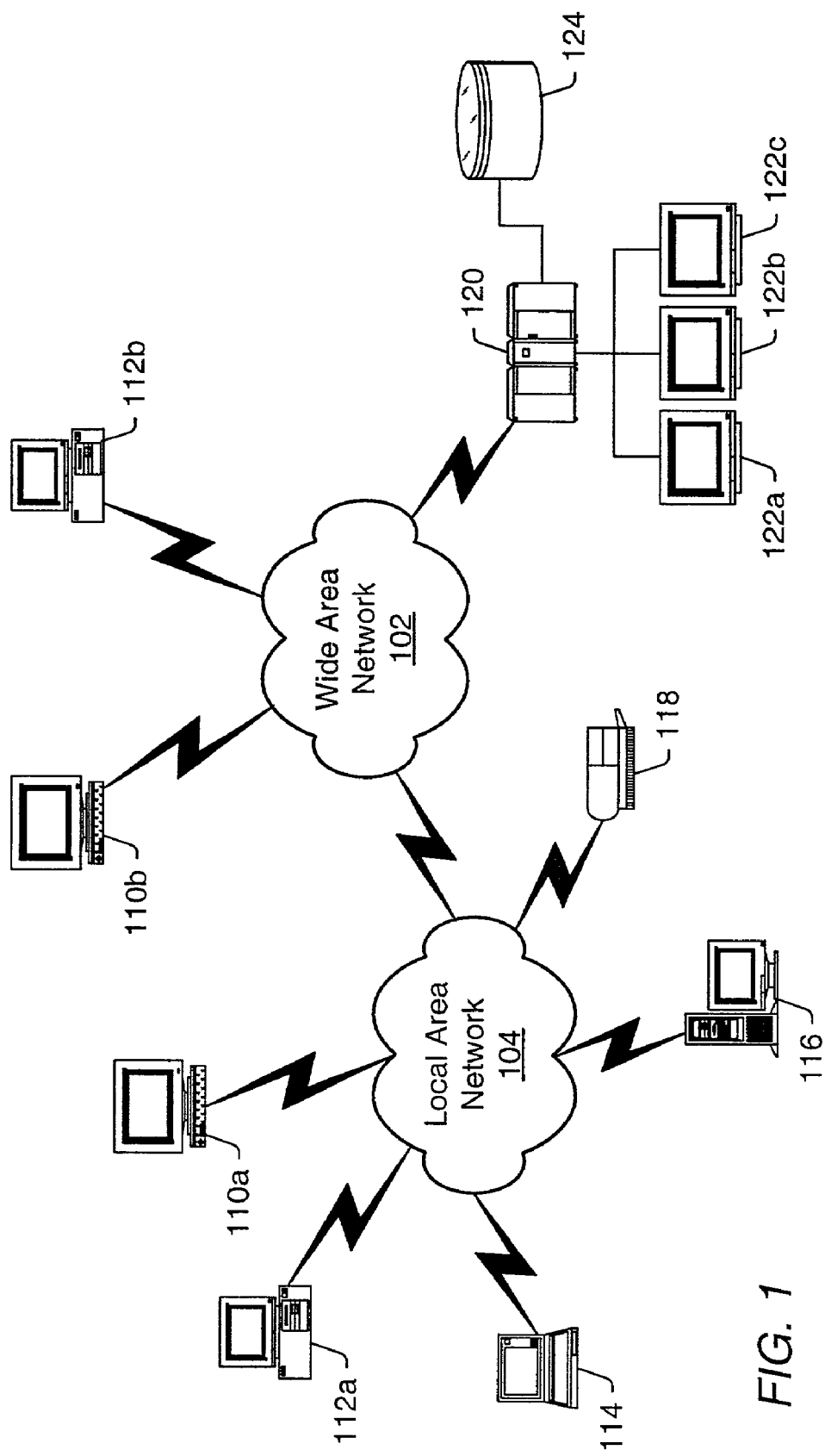
FIG. 1 depicts an embodiment of a network diagram of a wide area network suitable for implementing various embodiments.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF SEVERAL EMBODIMENTS

FIG. 1 illustrates a wide area network ("WAN") according to one embodiment. WAN 102 may be a network that spans a relatively large geographical area. The Internet is an example of WAN 102. WAN 102 typically includes a plurality of computer systems that may be interconnected through one or more networks. Although one particular configuration is shown in FIG. 1, WAN 102 may include a variety of heterogeneous computer systems and networks that may be interconnected in a variety of ways and that may run a variety of software applications.

One or more local area networks ("LANs") 104 may be coupled to WAN 102. LAN 104 may be a network that spans a relatively small area. Typically, LAN 104 may be confined to a single building or group of buildings. Each node (i.e., individual computer system or device) on LAN 104 may have its own CPU with which it may execute programs, and each node may also be able to access data and devices anywhere on LAN 104. LAN 104, thus, may allow many users to share devices (e.g., printers) and data stored on file servers. LAN 104 may be characterized by a variety of types of topology (i.e., the geometric arrangement of devices on the network), of protocols (i.e., the rules and encoding specifications for sending data, and whether the network uses a peer-to-peer or client/server architecture), and of media (e.g., twisted-pair wire, coaxial cables, fiber optic cables, and/or radio waves).

Each LAN 104 may include a plurality of interconnected computer systems and optionally one or more other devices such as one or more workstations 110a, one or more personal computers 112a, one or more laptop or notebook computer systems 114, one or more server computer systems 116, and one or more network printers 118. As illustrated in FIG. 1, an example LAN 104 may include one of each computer systems 110a, 112a, 114, and 116, and one printer 118. LAN 104 may be coupled to other computer systems and/or other devices and/or other LANs 104 through WAN 102.

One or more mainframe computer systems 120 may be coupled to WAN 102. As shown, mainframe 120 may be coupled to a storage device or file server 124 and mainframe terminals 122a, 122b, and 122c. Mainframe terminals 122a, 122b, and 122c may access data stored in the storage device or file server 124 coupled to or included in mainframe computer system 120.

WAN 102 may also include computer systems connected to WAN 102 individually and not through LAN 104 for purposes of example, workstation 110b and personal computer 112b. For example, WAN 102 may include computer systems that may be geographically remote and connected to each other through the Internet.

Figure 2:
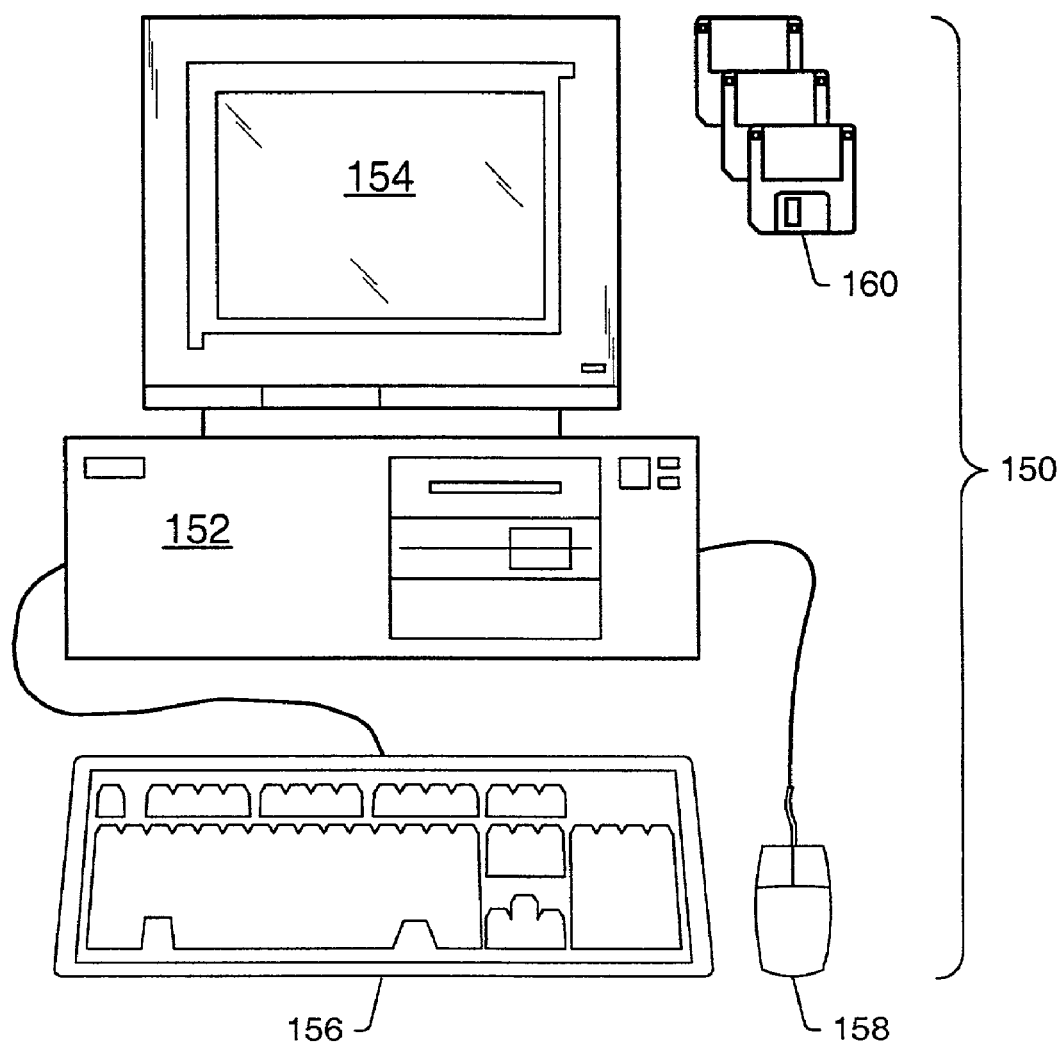
FIG. 2 depicts an embodiment of a computer system suitable for implementing various embodiments.

FIG. 2 illustrates an embodiment of computer system 150 that may be suitable for implementing various embodiments of a system and method for assessment of liability in a motor vehicle accident by considering characteristics that describe such an accident combined with expert knowledge collected from experienced claims adjusters. Each computer system 150 typically includes components such as CPU 152 with an associated memory medium such as floppy disks 160. The memory medium may store program instructions for computer programs. The program instructions may be executable by CPU 152. Computer system 150 may further include a display device such as monitor 154, an alphanumeric input device such as keyboard 156, and a directional input device such as mouse 158. Computer system 150 may be operable to execute the computer programs to implement assessment of liability in a motor vehicle accident by considering characteristics that describe such an accident combined with expert knowledge collected from experienced claims adjusters.

Computer system 150 may include a memory medium on which computer programs according to various embodiments may be stored. The term "memory medium" is intended to include an installation medium, e.g., a CD-ROM or floppy disks 160, a computer system memory such as DRAM, SRAM, EDO RAM, Rambus RAM, etc., or a non-volatile memory such as a magnetic media, e.g., a hard drive or optical storage. The memory medium may also include other types of memory or combinations thereof. In addition, the memory medium may be located in a first computer which executes the programs or may be located in a second different computer which connects to the first computer over a network. In the latter instance, the second computer may provide the program instructions to the first computer for execution. Also, computer system 150 may take various forms such as a personal computer system, mainframe computer system, workstation, network appliance, Internet appliance, personal digital assistant ("PDA"), television system or other device. In general, the term "computer system" may refer to any device having a processor that executes instructions from a memory medium.

The memory medium may store a software program or programs operable to implement a method for assessment of liability in a motor vehicle accident by considering characteristics that describe such an accident combined with expert knowledge collected from experienced claims adjusters. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes ("MFC"), browser-based applications (e.g., Java applets), traditional programs, or other technologies or methodologies, as desired. A CPU such as host CPU 152 executing code and data from the memory medium may include a means for creating and executing the software program or programs according to the embodiments described herein.

Various embodiments may also include receiving or storing instructions and/or data implemented in accordance with the foregoing description upon a carrier medium. Suitable carrier media may include storage media or memory media such as magnetic or optical media, e.g., disk or CD-ROM, as well as signals such as electrical, electromagnetic, or digital signals, may be conveyed via a communication medium such as networks 102 and/or 104 and/or a wireless link.

Figure 3:
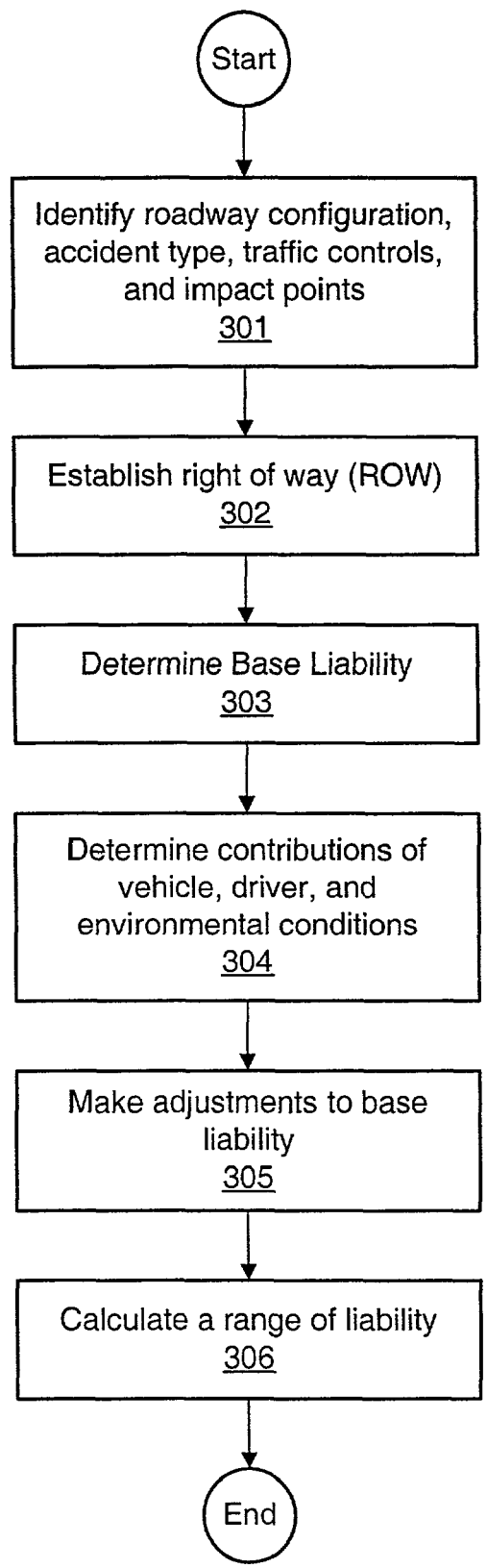
FIG. 3 depicts a flowchart of an embodiment of a liability estimation process.

FIG. 3 is a flowchart of an embodiment of a liability estimation process for vehicle accidents according to one embodiment. As used herein, the term "liability" generally refers to an amount for which a person or party is responsible or obligated. In an embodiment, liability in an accident may be expressed in a ratio or percentage (e.g., there is a total of 100% liability that can be attributed to persons, parties, or other factors such as weather, etc.). In another embodiment, liability may be expressed as a dollar amount.

An embodiment may apply to accidents involving many different types of vehicles (e.g., automobiles, light trucks, heavy trucks, motor cycles, school buses, vans, commercial trucks, tractor-trailers, motor homes, recreational vehicles, commercial buses, farming related vehicles, tractors). It is anticipated that an embodiment may apply to accidents involving other types of transportation craft such as boats and airplanes. It is also anticipated that an embodiment may apply to other types of accidents such as premises liability, which may include slip, trip and fall, dog bite, food poisoning, etc.

When two or more vehicles are involved in a motor vehicle accident, typically an estimation of liability is needed in order to settle a claim that a claimant may make against an insured. As used herein, the term "claimant" generally refers to a party involved in an accident that seeks compensation for bodily injury and/or property damage from the claims organization of an insurance carrier of another party, the insured, involved in the accident. As used herein, the term "insured" generally refers to a party involved in an accident who holds an insurance policy with a claims organization of an insurance carrier that obligates the claims organization of an insurance carrier to compensate a third party for the portion of the damages suffered by the third party that was the fault of the insured party in the accident.

The estimation of liability may be a complicated process involving multiple characteristics. Gathering the characteristics may typically be a task completed by a claims adjuster. As used herein, the term "claims adjuster" generally refers to an individual employed by a claims organization of an insurance carrier who assesses the liability of each party involved in an accident. When the claims adjuster has collected some or all of the information available, the claims adjuster may enter the information into a computer system. Examples of data input screens that may be suitable for entering accident information into a computer are shown in FIGS. 42-55.

The claims adjuster may provide to a computer system a real set of characteristics relating to a real accident. As used herein the term "real characteristics" generally refers to characteristics that describe an accident being considered for liability assessment. The computer system may have access to a memory that contains sets of characteristics that correspond to past or theoretical accidents. As used herein, the term "past accident" generally refers to an accident that occurred in the past of which certain characteristics may be stored in a memory of a computer system. As used herein, the term "theoretical accident" generally refers to an accident that might occur. The computer system may be configured to provide an estimate of liability for each set of characteristics in the memory.

The computer system may correlate the real set of characteristics from the real accident to the sets of characteristics in the memory to determine a set of characteristics that most closely approximates or matches the real set of characteristics. The computer system may then use the estimates of liability for the sets of characteristics in the memory to estimate liability for the real accident. It is anticipated that one or more of the sets of characteristics may be used to estimate liability.

FIG. 3 provides an overview of an embodiment of a liability estimation process based on multiple characteristics that may describe a vehicle accident. In step 301, a claims adjuster may identify a set of real characteristics relating to a real accident. A set of real characteristics may include, but are not limited to, roadway configuration, accident type, and impact points of each motor vehicle. Additionally, the real set of characteristics may include identification of traffic controls at the scene of the accident. Screen shots illustrating examples of providing each of these characteristics to a computer system may be found as follows: roadway configurations in FIG. 47, accident types in FIG. 47, traffic controls in FIG. 48, and impact points in FIG. 49.

Figure 7A:
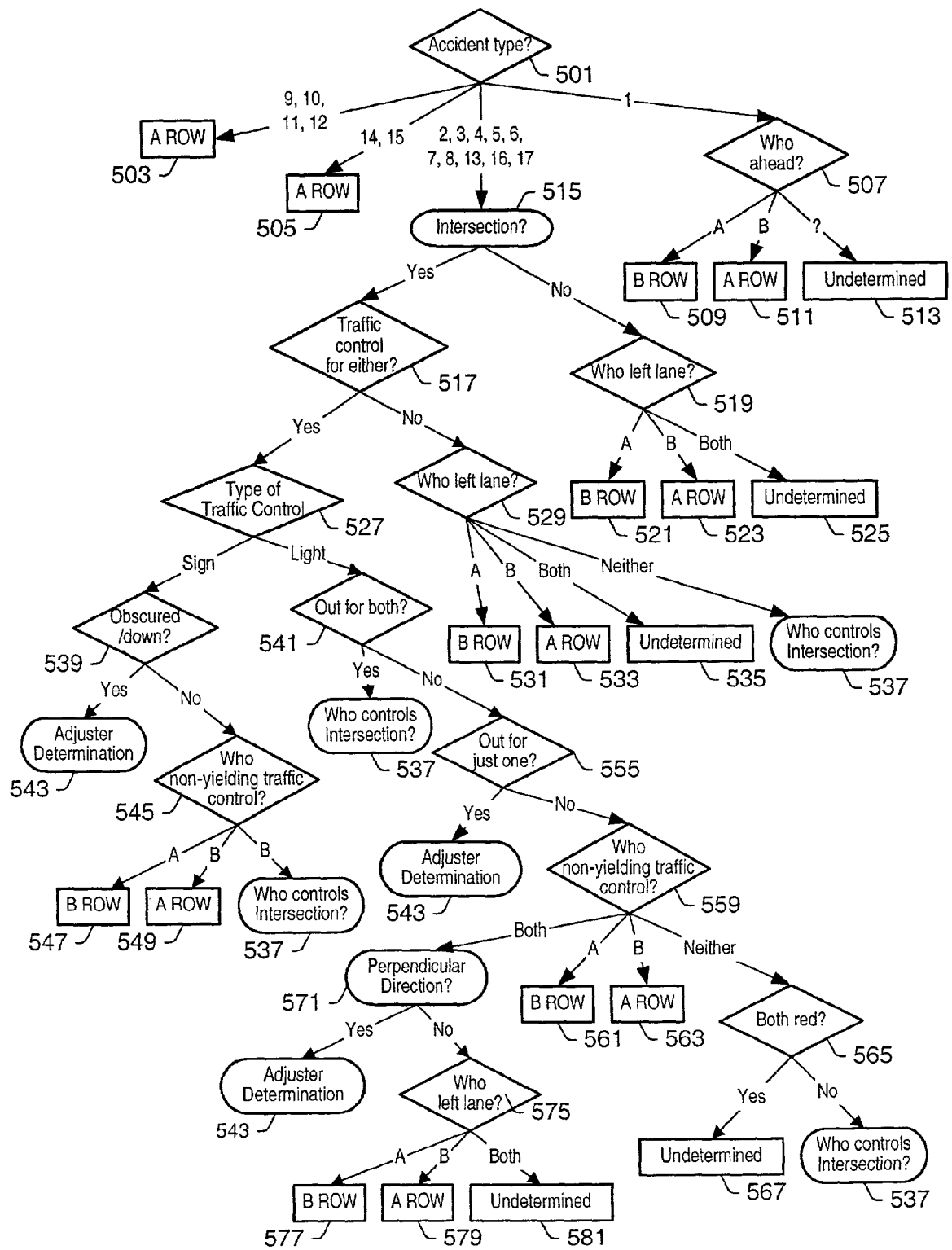
FIG. 7a is a flowchart for determining the right of way according to one embodiment.
Figure 7B:
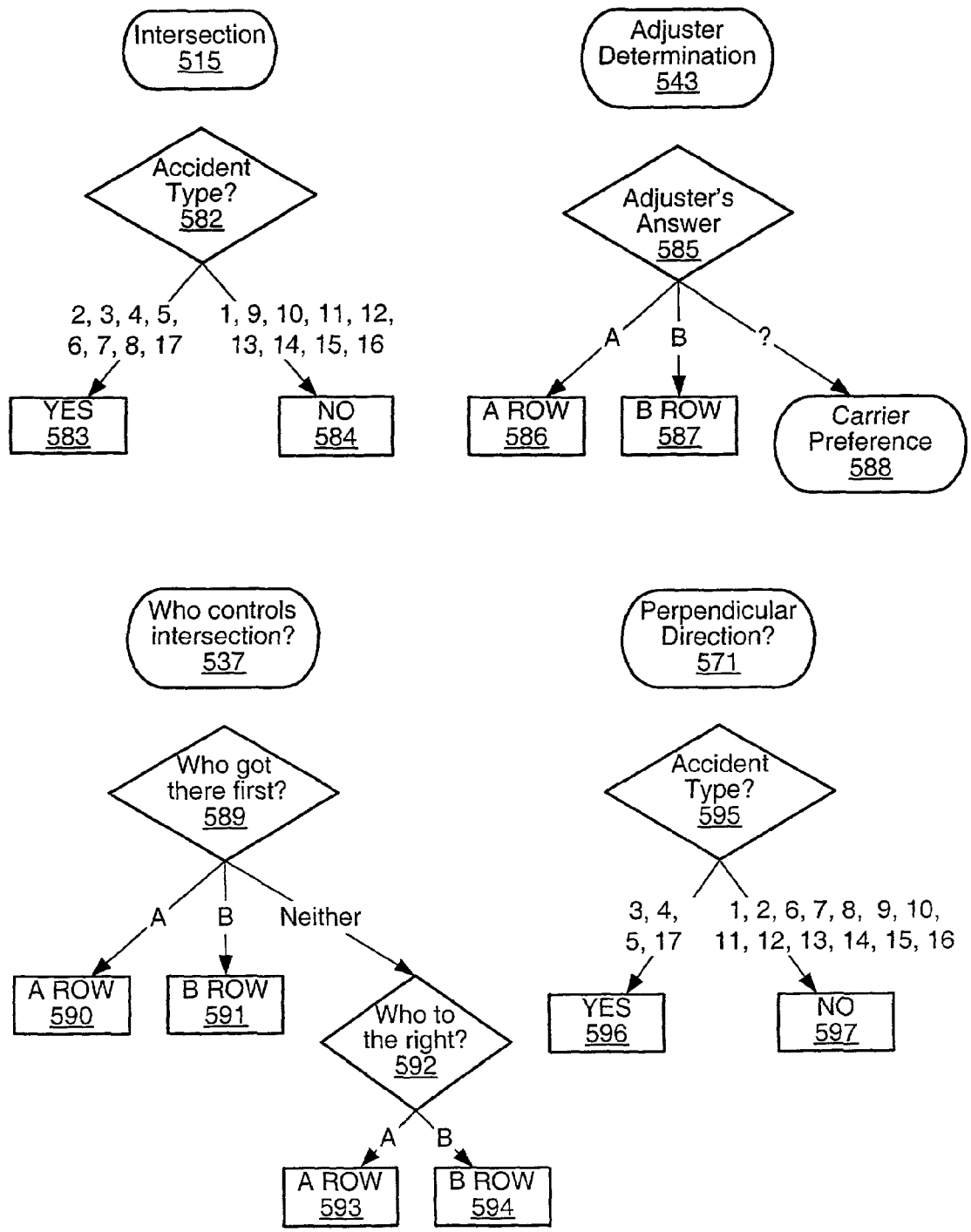
FIG. 7b is a group of flowchart corresponding to the flowchart in FIG. 5a according to one embodiment.

In step 302, the right of way ("ROW") may be established by a computer system from one or more of the real characteristics. Additionally, the computer system may ask one or more questions about the real accident to establish the ROW. At least one of the real characteristics may include a roadway configuration, an accident type, or a traffic control. FIGS. 7a and 7b show flowcharts that illustrate an embodiment of right of way determination. Alternatively, the claims adjuster may specify the ROW.

In step 303, a base liability may be estimated from a table or database of characteristics that contain sets of characteristics that correspond to past or theoretical accidents. As used herein, the term "base liability" generally refers to the portion of the liability that is independent of factors specific to condition of vehicles in the accident, condition of drivers in the accident, actions of drivers in the accident, and environmental conditions common to vehicles in the accident. A computer system may have access to a memory that contains sets of characteristics such as roadway configuration, accident type, traffic control, right of way, and impact points of the vehicles involved in the vehicle accidents that correspond to past or theoretical accidents. Each of the sets of characteristics for past or theoretical accidents may be associated with an estimate of base liability. FIGS. 37 to 41 are screen shots of a knowledge acquisition utility and a tuning utility that may be utilized to input base liability information into a computer system. The utilities may be used to create a database of sets of characteristics that correspond to past or theoretical accidents.

The computer system may compare the real set of characteristics established or identified in the earlier steps (e.g., roadway configuration, accident type, traffic control, right of way, impact points) to the sets of characteristics relating to past or theoretical accidents to determine a nearest matching set of characteristics among the sets of characteristics relating to past or theoretical accidents. The computer may then determine an estimate of liability for the real accident based on the estimate of liability associated with the nearest matching set of characteristics among the sets of characteristics relating to past or theoretical accidents. It is anticipated that a computer system may be configured to provide an estimate of liability using at least one of the sets of characteristics that correspond to past or theoretical accidents.

Figure 51:
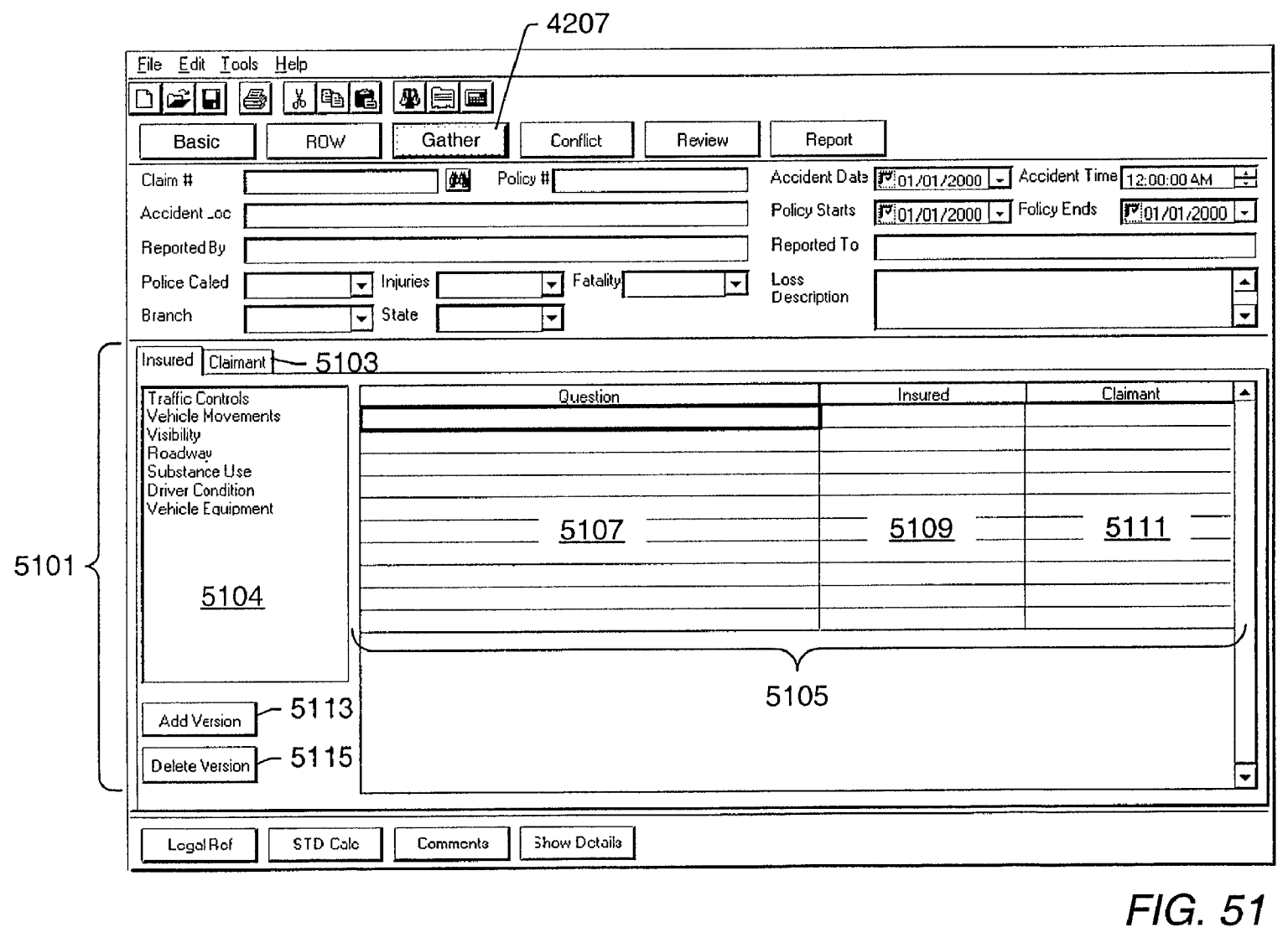

In step 304, the claims adjuster may identify to the computer system one or more factors corresponding to a real accident. The factors may include characteristics specific to condition of vehicles in the accident, condition of drivers in the accident, actions of drivers in the accident, or environmental conditions common to vehicles in the accident. The computer system may have access to a memory that contains corresponding factors associated with one or more past or theoretical accidents. One or more of the factors associated with past or theoretical accidents may be associated with an estimate of the effect on liability of the factor. The computer system may compare the factors associated with the real accident to factors associated with past or theoretical accidents to determine one or more nearest matching factors. Estimates of the effect on liability of the determined nearest matching factors may be used to estimate the effect on liability of the factors associated with the real accident. FIG. 51 is a screen shot showing a graphical user interface for entering conditional factors into a computer system.

In some embodiments, the estimate of the effect on liability of each factor may be adjustable. For example, the adjustments may be due to sets of characteristics corresponding to the real accident, the preference of a claims organization, knowledge of an experienced claims adjuster, or requirements of a jurisdiction in which the accident took place. FIGS. 10a through 36 illustrate several embodiments of estimates of the effect on liability of several factors which may be associated with theoretical accidents. It is anticipated that there are other methods than those shown in and described in reference to FIGS. 10a to 36 to estimate effects on liability due to the contribution of various factors.

In step 305, any necessary adjustments to the base liability estimated in step 303 due to contributions from factors estimated in 304 may be made. One example of a necessary adjustment may be an Absolute Liability Value. As used herein, the term "Absolute Liability Value" ("ALV") is generally defined as a factor that makes a significant contribution to liability such as negating the effect of other factors or characteristics associated with the accident. An ALV may also be defined as a factor that may adjust the liability beyond the lower and upper bounds defined for the liability. However, an ALV may not always shift liability to the other party. For example, an ALV might simply absolve one party of liability and explain the accident as being unavoidable. In such a situation, the contribution of various factors and characteristics may be ignored and an ALV may be assigned. For example, if a person had a sudden, unforeseen heart attack that caused an accident, the base liability might be determined to be 75 percent, but the final liability may be set via an ALV at 0 percent because the accident was probably unavoidable.

In step 306, all of the previously entered information may be taken into account and processed. Reference to expert knowledge databases, and other static information (such as jurisdictional information) may be made in calculating a range of liability. A range of liability may be more suitable than a single value in negotiations between parties regarding fault.

Figure 4:
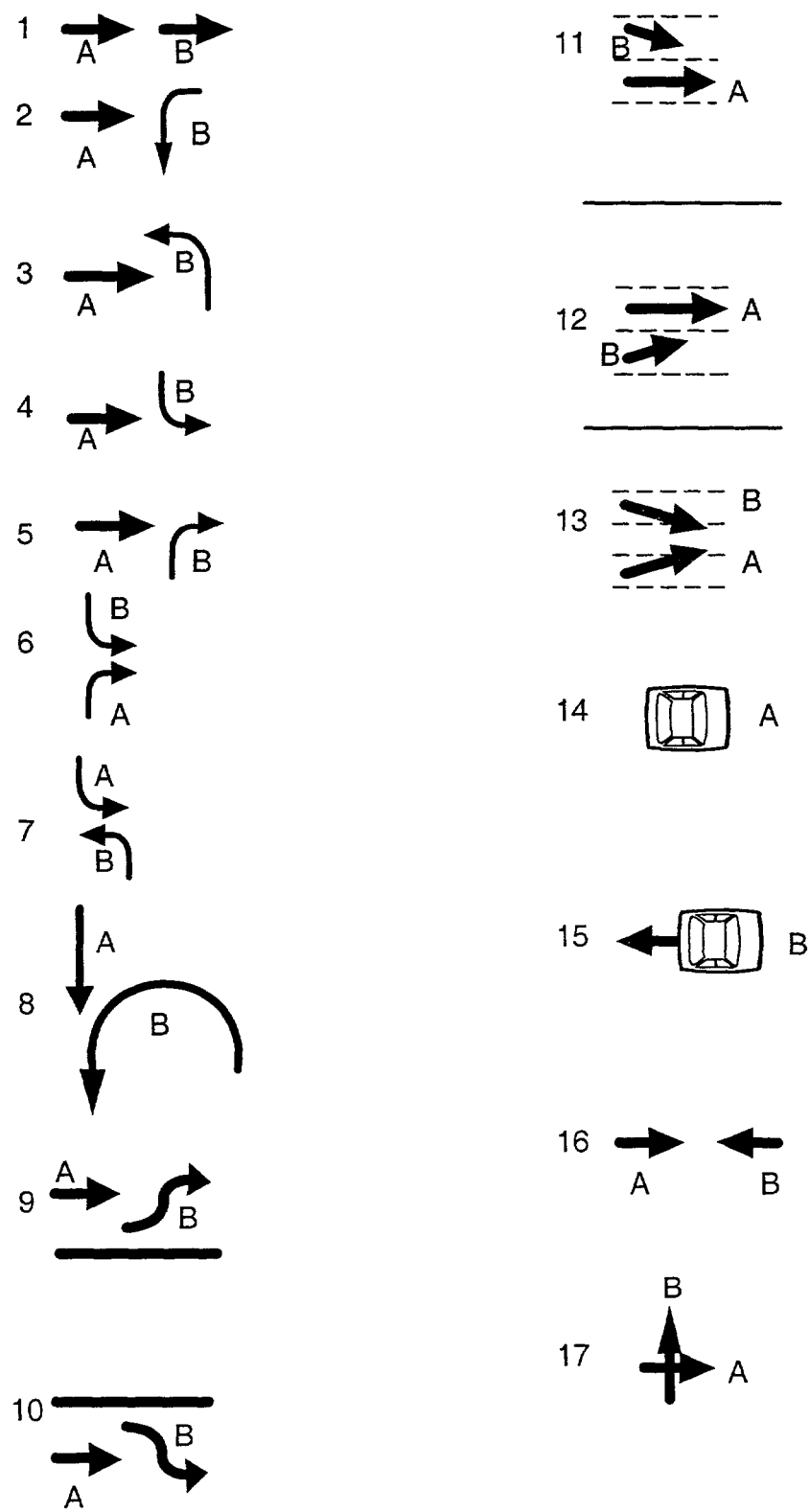
FIG. 4 is a diagram representing accident types according to one embodiment.

FIG. 4 illustrates graphical representations of various different accident types involving motor vehicles according to one embodiment. The arrows represent the paths of motor vehicle A and motor vehicle B at or near the time of the accident. Solid lines with no arrows represent the edge of a roadway. Dashed lines represent lanes. The user may select an accident type that corresponds to the real vehicle accident as shown in the screen shot in FIG. 47. As used herein, the term "user" generally refers to a claims adjuster or another individual employed by a claims organization. Accident types graphically represented in FIG. 4 may include: (1) a rear ender, (2) a left turn crossing traffic, (3) a left turn across traffic, (4) a left turn entering traffic, (5) a right turn entering traffic, (6) dual turns to same lane, (7) concurrent left turns, (8) a U-turn, (9) a parked vehicle merging into traffic from right, (10) a parked vehicle merging into traffic from left (e.g. on a one way street), (11) a merge from the left, (12) a merge from the right, (13) concurrent merges to a single lane, (14) a collision with a parked vehicle, (15) a collision while backing, (16) a head on, and (17) a straight cross traffic collision. Additionally, in some embodiments, a right turn across traffic accident type (not shown) may be represented.

Figure 5:
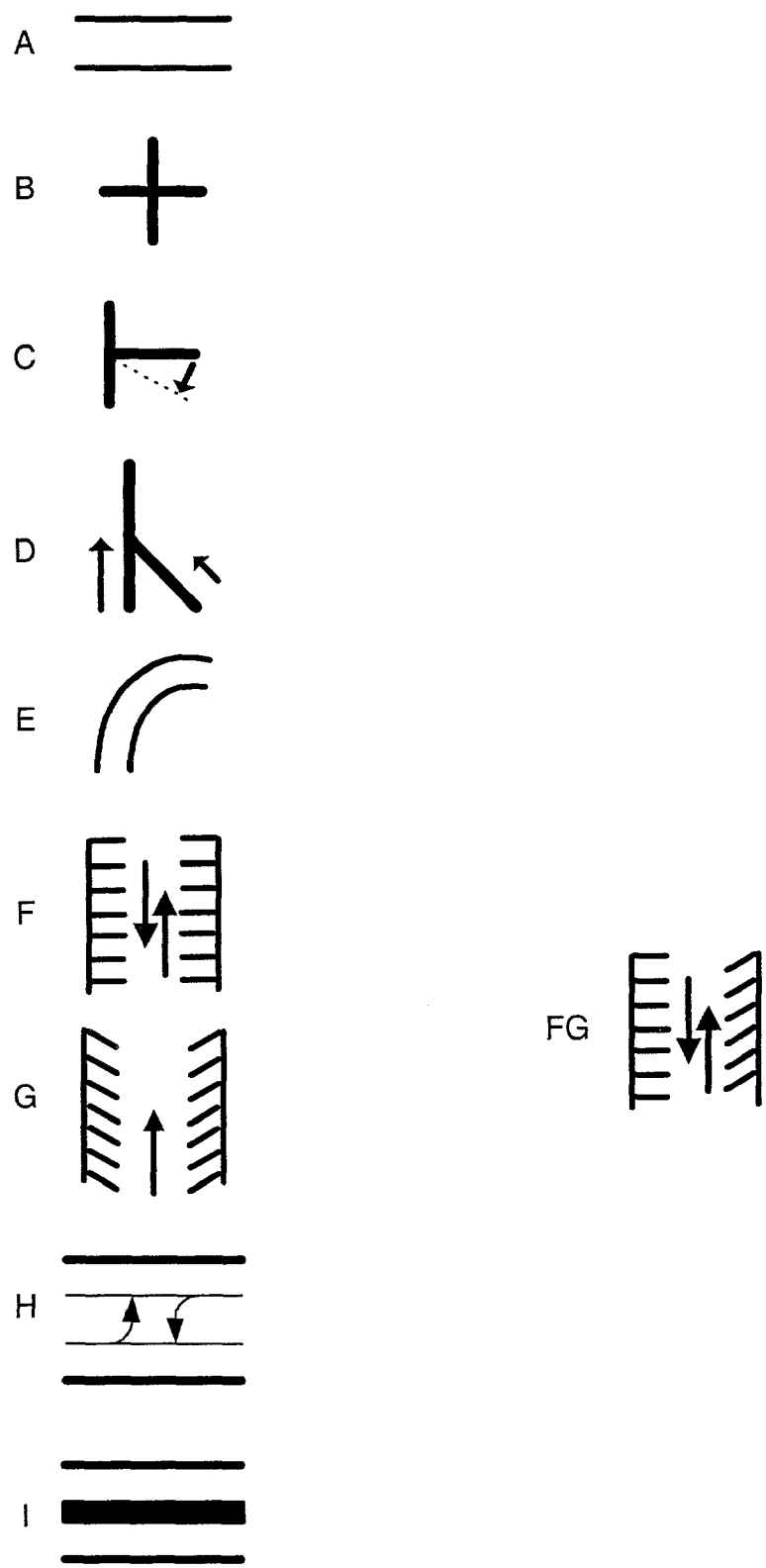
FIG. 5 is a diagram representing roadway configurations according to one embodiment.

FIG. 5 illustrates graphical representations of various different roadway configurations according to one embodiment. The user may select one of the roadway configurations that correspond to a real vehicle accident as shown in the screen shot in FIG. 47. Roadway configurations graphically represented in FIG. 5 may include: (A) a two or more lane road (including a divided road with a median that may be crossed), where the solid lines are the roadway and the space between is the median; (B) a four-way intersection with the lines representing the crossing roadways; (C) a T-angle intersection (the T-angle that may vary), where the solid lines are the roadway and where the dashed line represents the variation of the angle of the intersection; (D) a merging of one roadway into another with no turns and in one direction with the arrows showing the direction of the vehicles; (E) a curve with the lines showing the roadway; (F) a parking lot with two-way traffic where the arrows show the direction of the vehicles, the vertical lines represent the boundary of the parking lot, and the spaces between the horizontal lines represent the parking spaces; (G) a parking lot with one way traffic where the arrow shows the direction of the vehicles, the vertical lines represent the boundary of the parking lot, and the spaces between the diagonal lines represent the parking spaces; (H) a center turn lane with the bold lines representing the boundary of the roadway, the thin lines marking the boundary between the driving lanes and the center turn lane, and the arrows representing the direction of the center lane turns; (I) a two or more lane road divided by a physical barrier with the thicker center line representing the physical barrier and the thinner lines representing the outer boundaries of the roadway.

Alternatively, the roadway configurations of the parking lots, (F) and (G), may be represented by a single diagram, (FG), shown in FIG. 5. (FG) is the same as (F), except that the parking spaces on the right of the diagram are formed by diagonal lines. In an embodiment, (FG) may be used to represent a parking lot of any configuration.

FIG. 6 is a matrix illustrating the applicable roadway configuration/accident type combinations in liability estimation according to one embodiment. Accident types, (1) to (17) from FIG. 4, are listed on the vertical axis. Roadway configurations, (A) to (I) from FIG. 5, are listed on the horizontal axis. The alternative representation of the parking lots (F) and (G), (FG) is also included on the horizontal axis.

Figure 38:
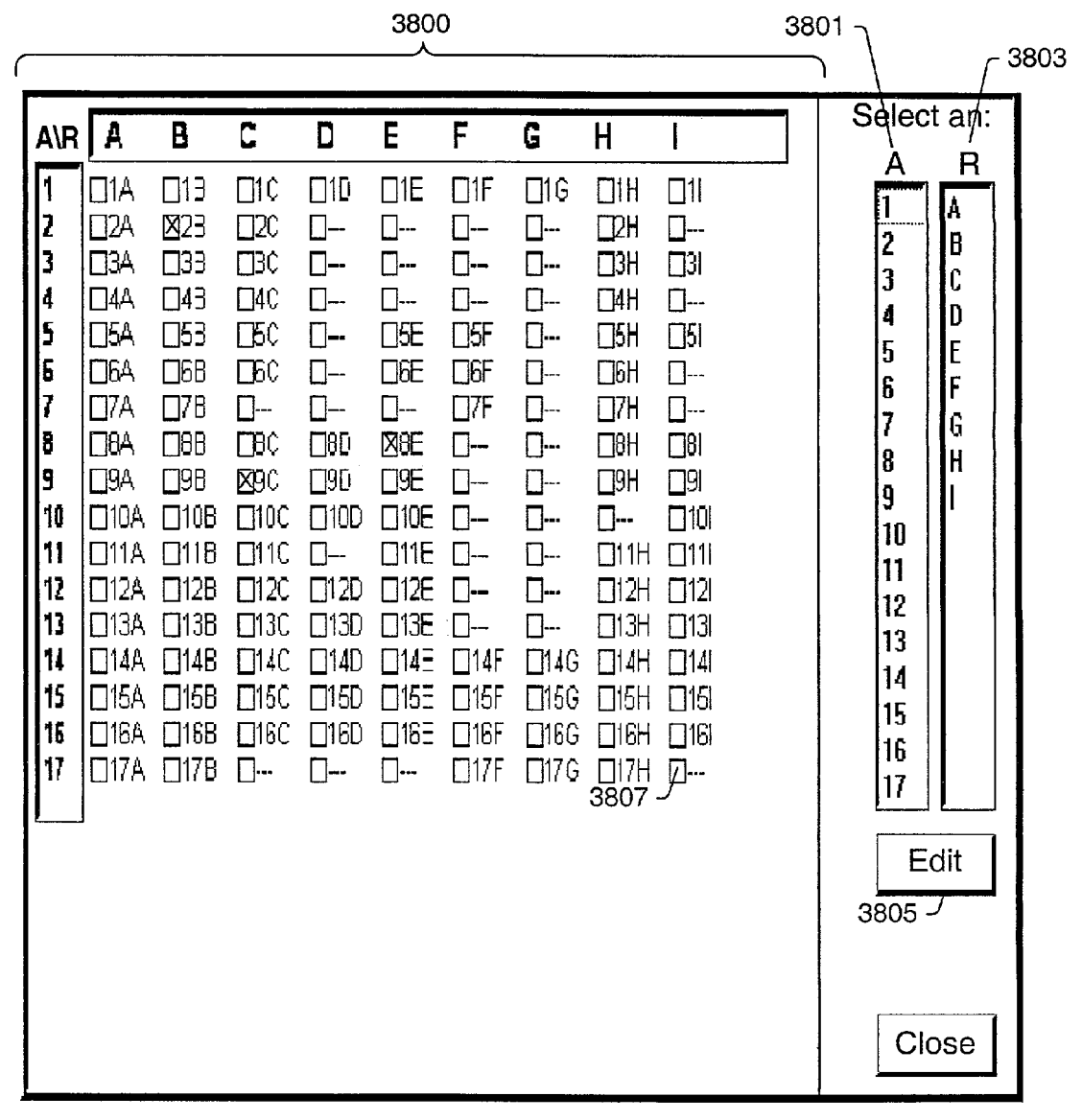

Experienced claims adjusters may consider combinations labeled "N" to be implausible accident scenarios and, therefore, not significant in liability assessment of motor vehicle accidents. Thus, combinations labeled "Y" may be considered a set of theoretical accident scenarios. FIG. 38 is a screen shot of a Knowledge Acquisition Utility, which shows a matrix of roadway configuration/accident types similar to FIG. 6. In FIG. 38, the elements of the matrix labeled with a "--" indicate implausible combinations. In the embodiment of FIG. 38, the implausible combinations are a subset of the combinations labeled with an "N" in FIG. 6 because the knowledge acquisition utility allows the user to consider some implausible combinations. An example of a combination marked as implausible in both FIGS. 6 and 38 is D2, left turn crossing traffic on a merge with no turns in one direction. An example of a combination that may be considered implausible in FIG. 6, but may be allowed for consideration in FIG. 38 is I16, a head on collision on a 2 or more lane road divided by a physical barrier.

FIG. 7a and 7b depict flowcharts for determining whether vehicle A or vehicle B has the right of way in traffic according to one embodiment. As used herein, the term "right of way" generally refers to the right of a vehicle to take precedence in traffic. The determination of right of way may require identification of one or more of the characteristics of the real accident (e.g., the roadway configuration, accident type, traffic control, or jurisdiction). Additionally, determining the right of way may require answering one or more questions concerning the accident. Alternatively, in some embodiments, the right of way may be specified by the user. FIG. 7b includes flowcharts of determinations that appear in the flowchart in FIG. 7a. In FIG. 7b, the Intersection flowchart identifies the accident types that involve intersections. The Perpendicular Directions flowchart identifies the accident types that involve vehicles approaching from perpendicular directions. In Adjuster Preference, the claims adjuster may either assign the right of way to vehicle A or B, or defer to the insurance carrier's or claims organization's preference.

As shown by decision point 501 in FIG. 7a, the determination of the right of way may depend on the accident types illustrated in FIG. 4. The right of way may be determined from the accident type alone in some cases. For example, in accident types 9 and 10, merge of a parked vehicle, the vehicle already in traffic may have the right of way. Likewise, in accident types 11 and 12, the merge of a moving vehicle, the vehicle already in the lane may have the right of way. These determinations are shown by step 503 in which vehicle A in accident type diagrams 9, 10, 11 and 12 in FIG. 4 has the right of way. Additionally, as depicted in step 505, vehicle A may be determined to have the right of way if vehicle A is parked (accident type 14) or vehicle B is backing up (accident type 15).

For accident type 1, decision point 507 shows that the right of way may depend on which vehicle was ahead in the rear-ender. If vehicle B was ahead (as depicted in FIG. 4), step 511 shows that B may have the right of way. If vehicle A was ahead, step 509 shows that A may have the right of way. Alternatively, if it is unknown which vehicle was ahead (e.g., due to the circumstances or severity of the accident), step 513 indicates that the right of way may be undetermined. For an undetermined right of way the base liability of each vehicle may be set at 50%.

As shown in FIG. 7a, for accident types 2, 3, 4, 5, 6, 7, 8, 13, 16, and 17, the first step 515 is the intersection decision point, which is determination of whether the accident occurred at an intersection. The intersection flowchart is illustrated in FIG. 7b. Decision point 582 indicates that the presence of an intersection may be found from the accident type. If the accident type is 2, 3, 4, 5, 6, 7, 8, or 17, step 583 indicates that there may be an intersection. If the accident type is 1, 9, 10, 11, 12, 13, 14, 15, or 16, step 584 indicates an intersection may not be present. Alternately, in some embodiments, the presence of an intersection may be determined from roadway configuration information provided by the user. For example, roadway configurations A, E, F, G, I and FG may indicate that in intersection may not be present. Roadway configurations B, C, D, and H may indicate that an intersection may be present.

FIG. 7a shows that if there is no intersection, the next step is decision point 519. Decision point 519 is the determination of which vehicle left the lane it was in. As shown by steps 521 and 523, the vehicle that remained in the lane it was in may have the right of way. Alternatively, if both vehicles left their lanes, step 525 indicates that the right of way may be undetermined. In this case, the base liability may be assessed at 50% for each vehicle.

FIG. 7a shows that when there is an intersection, the next step is decision point 517 which is a determination of whether there is a traffic control for either vehicle A or B. If not, decision point 529 indicates that the right of way may depend on which vehicle left the lane it was in. Steps 531, 533, and 535 are analogous to steps 521, 523, and 525. However, if neither vehicle left the lane it was in, step 525 indicates that the vehicle that controls the intersection may have the right of way as shown by flowchart 537. The vehicle that controls the intersection may be determined by flowchart 537 shown in FIG. 7b. Decision point 589 in FIG. 7b is the first step in determining who controls the intersection. Decision point 589 asks which vehicle arrived at the intersection first. As shown by steps 590 and 591, the vehicle that arrived first at an intersection may control it. If neither vehicle arrived first, decision point 592 asks which vehicle is to the right. Steps 593 and 594 show that the vehicle to the right may control the intersection.

As illustrated in FIG. 7a, if the answer to decision point 517 is yes, then decision point 527 is next which asks the type of traffic control. Decision point 539, which is reached if the traffic control is a sign, asks if the sign is obscured or down. If the sign is obscured or down, step 543 shows that right of way may be determined by the adjuster. Adjuster determination is shown by the flowchart in FIG. 7b. Decision point 585 in FIG. 7b is the adjuster's answer for which vehicle, A or B, has the right of way, which is shown as steps 586 and 587. If the adjuster does not have an answer, then the right of way may be the carrier's preference as shown by step 588.

However, if the answer to decision point 539 is no, decision point 545 asks which vehicle had a non-yielding traffic control. Step 547 shows that if A had the non-yielding traffic control, then B may have the right of way. Step 549 shows that if B had the non-yielding traffic control, then A may have the right of way. Step 551 applies if neither A nor B has the non-yielding traffic control. The right of way may be determined by the vehicle that controls the intersection, which may be determined by the flowchart shown in FIG. 7b.

Alternatively, if the answer to decision point 527 is a traffic light, then decision point 541 asks if the light was out for both vehicles. If the light was out for both, then right of way may be determined by who controls the intersection, which is shown in FIG. 7b. If the answer to decision point 541 is no, decision point 555 asks if the light was out for only one vehicle. If the light was out for only one vehicle, then right of way may be found from adjuster determination, which is given by the flowchart in FIG. 7b. However, if the answer to decision point 555 is no, decision point 559 is reached. Decision point 559 asks which vehicle has a non-yielding traffic control. As step 561 shows, if A has the non-yielding traffic control and B does not, then B may have the right of way. As step 563 shows, if B has the non-yielding traffic control and A does not, then A may have the right of way. If neither A nor B has the non-yielding traffic control, then decision point 565 is reached, which inquires whether both had a red light. If the answer to decision point 565 is yes, the right of way may be undetermined, as shown in step 567. In this case, the base liability may be assessed at 50% for each vehicle. If the answer to decision point 565 is no, then right of way may be determined by the vehicle that controls the intersection. The vehicle that controls the intersection may be determined by the flowchart shown in FIG. 7b. If both vehicles in decision point 559 have non-yielding traffic controls, then decision point 571 is reached. Decision point 571 asks whether the vehicles were approaching in perpendicular directions, which may be determined from the flowchart in FIG. 7b. As shown by decision point 595 in FIG. 7b, whether the vehicles were approaching in perpendicular directions may be determined from the accident types shown in FIG. 4. Step 596 shows that the answer is yes if the accident type is 3, 4, 5, or 17. Step 597 shows that the answer is no if the accident type is 1, 2, 6, 7, 8, 9, 10, 11, 12, 13, 14, 15, or 16. If the vehicles were approaching in perpendicular directions, then right of way may be determined by the adjuster. Adjuster determination may be given by the flowchart in FIG. 7b. If the vehicles were not approaching in a perpendicular direction, then decision point 529 shows that the right of way again may depend on which vehicle left the lane it was in. Steps 577, 579, and 581 are analogous to steps 521, 523, and 525.

Figure 42:
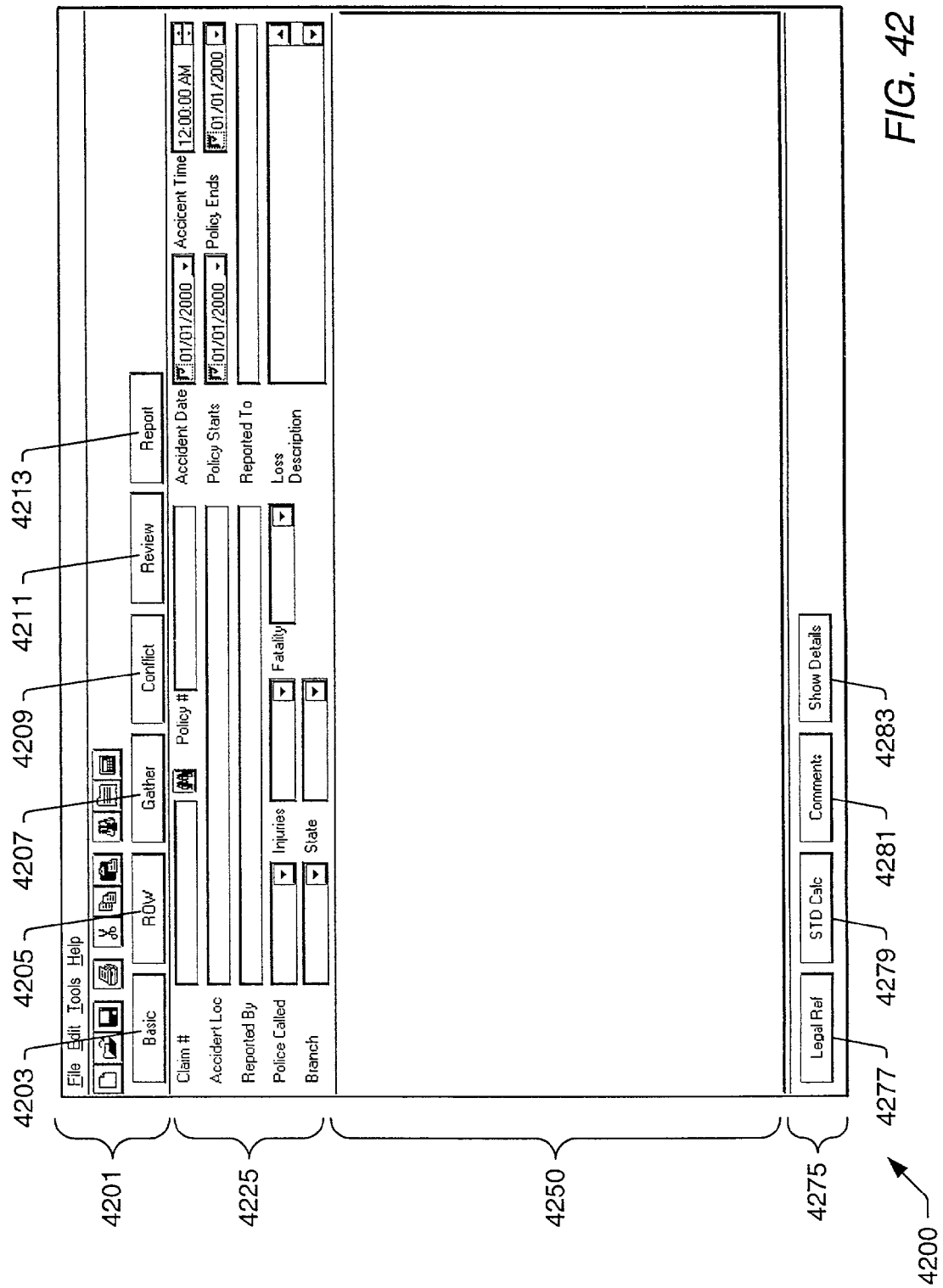
FIG. 42 is a screen shot of a Claim Data window according to one embodiment.
Figure 48:
FIG. 48 is a screen shot of a Traffic Controls data frame according to one embodiment.

An example of a screen shot of user input of a traffic control is shown in FIG. 48. An example of a screen shot of user input of the jurisdiction is shown in FIG. 42. Jurisdiction may include each of the fifty states of the United States and territories of the United States. In another embodiment, jurisdiction may include any governmental entity with traffic laws, such as a foreign country. The vehicle that does not have the right of way may generally be referred to as the "tortfeasor" ("TF") and the vehicle that has the right of way may generally be referred to as the "other party" ("OP"). For the case of an undetermined right of way, both parties may be considered the "other party" when determining the effect of one or more factors on the liability.

In an embodiment, a traffic control may be considered as "yielding" or "nonyielding." As used herein, the term "yielding traffic control" generally refers to a traffic control that informs a driver that he or she must give way (or stop) for other traffic. As used herein, the term "nonyielding traffic control" generally refers to a traffic control that informs the driver that he or she may proceed. Traffic controls may be further divided into three categories: pure, other explicit controlling devices, and markings and signs. Yielding pure traffic controls may include, but are not limited to, no traffic control present, a red light, a stop sign, a yield sign, a flashing red light, or a police officer signaling stop. Nonyielding pure traffic controls may include, but are not limited to, a yellow light, a green light, a green arrow left, a green arrow right, a flashing yellow light, or a police officer signaling proceed.

Yielding other explicit controlling devices may include a crossing guard signaling stop, a flagger signaling stop, another person signaling stop, and a school bus loading or unloading. Nonyielding other explicit controlling devices may include a crossing guard signaling proceed, a flagger signaling proceed, or another person signaling proceed. In some embodiments, emergency vehicle may also be yielding traffic controls depending upon the jurisdiction.

Whether a traffic control in the pure category overrides a selection in the other explicit controlling devices category may depend upon the jurisdiction. For example, whether a vehicle with a green light must yield to an approaching emergency vehicle may vary depending on the jurisdiction.

In one embodiment, a user may only select one traffic control from each category. The user may not have to select a traffic control from more than one category. If a user does select more than one, then the user may select which category should be considered as the governing control. A secondary traffic control may be listed in a report as informational only.

Markings and signs such as lane markings may also be traffic controls. In some embodiments, the presence of markings or signs may be noted for informational purposes. For example the presence of a disobeyed marking may be noted for use as a negotiation or talking point rather than being used to estimate liability or right of way. The markings and signs may include, but are not limited to: a one way sign or marking, a do not enter sign or marking, a no passing sign or marking, a no parking zone sign or marking, a straight only sign or marking, a left turn only sign or marking, a right turn only sign or marking, no U turn sign or marking, a no right turn on red sign, cones and/or barricades, a solid yellow line, a solid white line, or a no stopping sign or marking.

Figure 8A:
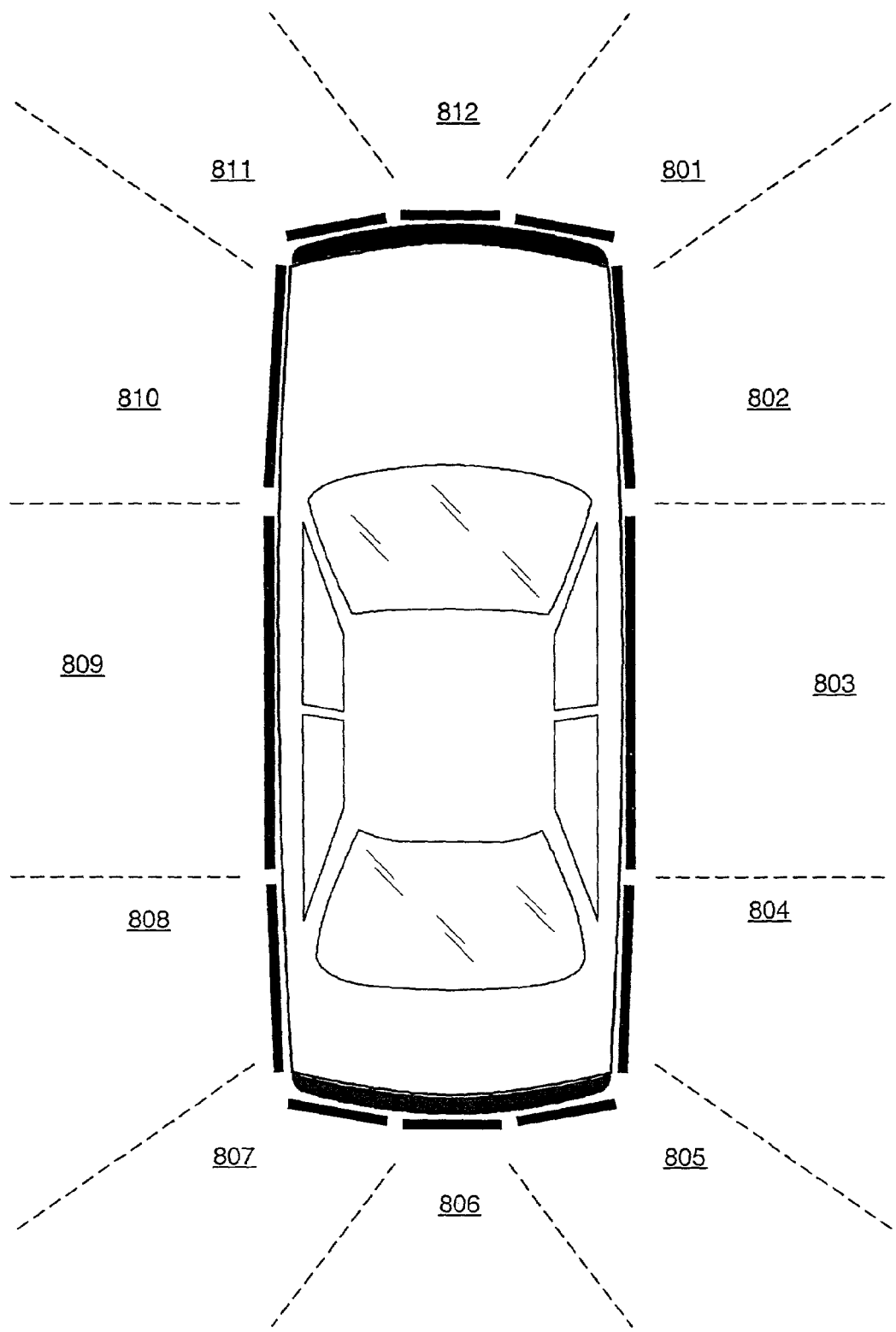
FIG. 8a is a diagram illustrating impact points on a motor vehicle according to one embodiment.

FIG. 8a is an illustration of a graphical representation of the impact points on a vehicle according to one embodiment. FIG. 8a is a graphical representation of a vehicle that is divided into twelve sections: 801-right front corner, 802-right front fender, 803-right middle, 804-right rear quarter-panel, 805-right rear corner, 806-rear middle, 807-left rear corner, 808-left rear quarter-panel, 809-left middle, 810-left front fender, 811-left front corner, and 812-front middle. Each of the labeled sections may correspond to a possible point of impact in a motor vehicle accident.

FIG. 8b is a table showing impact groups for combinations of roadway configuration and accident type according to one embodiment. A given roadway configuration/accident type combination may have a number of possible impact groups. As used herein, the term "impact group" generally refers to a collection of pairs of impact points for a past or theoretical accidents. A pair of impact points may include the impact point for each of two vehicles involved in an accident. In some embodiments, each pair of impact points may be associated with sets of liability estimate values. One set of values may correspond to vehicle A having the right of way and the other set of values to vehicle B having the right of way. Each set of values may include a value of base liability, a lower bound of liability, and an upper bound of liability for each vehicle. Alternately, in some embodiments, each impact group may be associated with sets of values corresponding to base liability values. It is anticipated that there may be various ways to arrange impact points in impact groups.

For example, as shown in FIG. 8b, impact points associated with the roadway configuration/accident type combination 2B (a four-way intersection with vehicle A from top turning left and B from bottom going straight), may be grouped into four impact groups. A first impact group may include three pairs of impact points: A811B809, A811B810, and A810B808. A and B refer to motor vehicle A and motor vehicle B, respectively, and the numbers refer to points on the impact point diagram in FIG. 8a. For example, the impact point pair, A811B809, corresponds to vehicle A with an impact point on the left front fender (811) and vehicle B with an impact point on the left middle (809).

In an embodiment, each of the pairs of impact points in a given impact group may have the same base liability and lower and upper bound of liability. The estimation of the base liability values, lower and upper bounds of liabilities, and the impact groups may be estimated by expert claims adjusters through a process called knowledge acquisition.

In an embodiment, the base liability and the bounds of the liability for two vehicles involved in an accident may be estimated for a real accident by first specifying the roadway configuration (as shown in FIG. 5), accident type (as shown in FIG. 4), and pair of impact points (as shown in FIG. 8a) of vehicles A and B for the real accident. The vehicle that had the right of way may be determined as shown in FIGS. 7a and 7b. A table, like the one shown in FIG. 8b, may be searched for the impact group corresponding to the given roadway configuration/accident type combination that contains the specified pair of impact points that correspond to a past or theoretical accident. Once the roadway configuration/accident type combination and impact group of the past or theoretical accident are known, the base liability and bounds may be extracted from a table in a database that lists the base liabilities and bounds for each impact group for all applicable roadway configuration/accident type combinations.

FIG. 9a illustrates an embodiment of a method of estimating the effect of one or more factors on the liability. Factor adjustments may be considered for each vehicle based on data specific to condition of vehicles in the accident, condition of drivers in the accident, actions of drivers in the accident, or environmental conditions common to vehicles in the accident. Each factor may have an associated penalty value that may correspond to an amount that an experienced claims adjuster may add to the base liability when this factor is present alone. A user may identify the presence of factors in a real accident and provide a list of factors to the computer system.

In an embodiment, factors related to the condition of vehicles in the accident may include the presence of faulty equipment. As used herein, the term "faulty equipment" generally refers to any vehicle equipment malfunction that causes an action (e.g., stuck accelerator causes unwanted acceleration), prohibits the operator from taking action (e.g., failed braking system prevents stopping), or fails to perform an action (e.g., failed brake lights do not warn other drivers of braking). In an embodiment, factors related to environmental conditions common to the vehicle may include, but are not limited to, presence of a construction zone, an obstructed view or glare, a road condition, a road character, a road surface, a defective traffic control, weather or visibility. In an embodiment, the factors related to a driver's condition may include, but are not limited to, consumption of alcohol, consumption of illicit drugs, consumption of medications, driver inattention, lack of required corrective lenses, driver inexperience, driver fatigue, or driver illness. In an embodiment, factors related to a driver's actions may include, but are not limited to, following too closely, driving with headlights off, driving at an unsafe speed, a sudden stop or swerve, driving with taillights brake lights off, unsafe backing, failure to take evasive action, driving with high beams on, an improper lane change, improper parking, or improper signaling.

FIG. 9a is an illustration of one embodiment for estimating the effect on liability of one or more factors. The decision to apply a particular factor in a given situation may be made by an experienced claims adjuster. In alternate embodiments, the factor may be applied by a computer system based on input provided by a claims adjuster. The computer system may ask the claims adjuster one or more questions regarding the accident. Based on answers provided by the claims adjuster, the computer system may determine that one or more factors apply.

In the embodiment depicted in FIG. 9a, the effect of a factor on the liability may be adjusted by a situational weight for each roadway configuration/accident type and vehicle. A situational weight may have four levels: N/A (factor not applicable), low, normal, and high. An experienced claims adjuster may determine an appropriate situational weight to apply. In an alternate embodiment, a computer system may be configured to determine an appropriate situational weight based on information provided by a claims adjuster. For example, in a rear-ender, a factor related to the consumption of alcohol (e.g., being drunk) may be considered more important than it is in other types of accidents. Therefore, the situational weight may be "high" for the rear vehicle. However, whether the driver of the lead vehicle has consumed alcohol may be irrelevant. Thus, a situational weight of "N/A" may be assigned to the factor. Each level of the situational weight may be assigned a percentage. For example, the situational weight may be 50 per cent for low and 150 per cent for high.

In the example depicted in FIG. 9a, base liability values may have already been determined from a table of base liabilities of past or theoretical accidents, as was described in reference to FIG. 8b. For example, the insurance carrier may have determined that the base liability for the insured was 80%, with a lower bound of 50% and an upper bound of 100%. Consequently, base liability for the claimant may be 20%.

In an embodiment, the levels of the situational weights (e.g., N/A, low, normal, and high) may be represented as percent weights (e.g., 0%, 50%, 100%, and 150%, respectively). In some embodiments, for a given factor, the penalty value, the situational weight, the percent weight, and whether or not the factor may apply may be specified by the user. If the factor applies, the adjusted penalty may be estimated by multiplying the penalty value by the percent weight associated with the determined situational weight. For example, the adjusted penalty of 22.5% for alcohol for the insured may be estimated by multiplying the penalty (e.g., 15%) by the percent weight (e.g., 150%) associated with the determined situational weight (e.g., "high"). In an embodiment, answers to questions in the flowcharts may be used to determine whether a situational weight associated with a factor is low, medium, high, or not applicable.

In other embodiments, the penalty, and/or situational weight may not be determined directly by a user. In such an embodiment, the penalty and/or situational weight may be determined from the answers to a series of questions. The questions may be specific to one party (e.g., the tortfeasor or other party). The questions may relate to roadway configuration, accident type, and/or other characteristics of the accident. FIGS. 10a to 36 are flowcharts that depict methods of determining penalties values associated with various factors. In the FIGS. 10a to 36, the penalty values may be represented in certain of the flowchart terminuses as percentage values. In certain flowcharts, the penalty values may be represented by the terms "low," "medium," or "high." These terms may represent variables that correspond to penalty values. For example, the "low" term may correspond to a penalty value of 10%, the "medium" term may correspond to a penalty value of 20%, and the "high" term may correspond to a penalty value of 30%. In some embodiments, the penalty values associated with each of these terms may be configurable by the claims organization. In some embodiments, all of the penalty values determined by methods such as those depicted in FIGS. 10a through 36 may be configurable by the claims organization.

In some cases, a factor may be determined to be a talking point ("TP"). As used herein, the term "talking point" generally refers to a factor that may not affect liability and may be informational only because the liability may be inherent in the base liability for the roadway configuration/accident type combination and the right of way. In certain embodiments, a computer system may gather information related to an accident and note for the user talking points identified from the information. Talking points may be useful if two or more parties must come to a negotiated agreement regarding the assessment of liability from the accident. A factor may also be determined to be an ALV.

In some embodiments, the situational weight for a factor may not be controlled directly by the user. In such embodiments, a factor ranking may be provided by the user to indirectly adjust the effect of a factor. For example, the user may rank factors on a scale of 0 to 5. The ranking factor may take into account the importance that a given factor has to a claims organization when it is not related to the characteristics of a particular accident. A knowledge acquisition utility may be provided via a computer system. The knowledge acquisition utility may ask the user a series of questions related to one or more factors, and determine a ranking factor from answers provided by the user. Alternately, the user may be presented directly with a list or factors and may be asked to rank each factor on a provided scale. In such embodiments, factors ranked as having a greater importance may be provided a situational weight. Such a method may be used in some embodiments to determine penalty values associated with one or more factors.

One method of applying the factor ranking to situational weights may be to assign a weight in terms of a percentage value between 0 and 100%. A rank of 0 may correspond to 0% and a rank of 5 may correspond to 100%. Ranks between 0 and 5 may be assigned values in 20% increments. If a value is assigned to the situational weight for a given factor, the situational weight may be adjusted by the ranking factor. For example, if the system estimates that high beams have a situational weight of 10 percent, and the claims organization gave a rank of 4 to high beams, the adjusted situational weight may be 8 percent.

As used herein, the term "penalty value" generally indicates that a portion of liability that would otherwise be assessed to a first party is not assessed to the first party. In some cases, that portion of the liability may be shifted to a second party, where the second party may be another driver involved in the accident. In other cases, the liability may be shifted to a third party, where the third party was not a driver involved in the accident. For example, the third party may be an owner of an animal that contributed to the accident.

Adjusting the base liability based on factors may be done in a number of ways. For example, a direct shift may be used. In an embodiment, a portion of the base liability assessed to the first party may be shifted to the second party. In such a case, a penalty factor may be a percentage of the liability to shift. For example, if the first and second party would each be assessed with 50% of the liability for the accident. A penalty value of 80% for the second party means that the first party is assessed with 10% of the liability and the second party is assessed with 90% of the liability.

In some embodiments, a debit/credit system may be used. In such embodiments, an effect on liability for a particular factor may be determined. One half of the determined penalty value may then be added to a first party, and the other half subtracted from the second party. After all of the factors may have been considered, the penalty values for each party may be summed and applied to the base liability. For example, FIGS. 9b and 9c depict examples of applying a debit/credit system for assessing the effect of several factors on the liability. In the example of FIG. 9b, Factors 1 and 2 apply to the first party, having penalty values of 20% (i.e., 10%+10%) and 30% (i.e., 15%+15%), respectively. Additionally, Factor 3 applies to the second party, having a penalty value of 10%. Therefore, a total of 20% may be added to the base liability of the first party, leaving a 70% liability assessment for the first party. The second party may receive a 30% liability assessment as a result of 20% being subtracted from the base liability of the second party. In some embodiments, effects on liability adjust the base liability by multiplying the sum of the effects on liability times the base liability. For example, using the same numbers as in FIG. 9c, but multiplying the sum by the base liability the first and second parties may be assessed with 60% and 40%, respectively. In addition to the calculation demonstrated in FIGS. 9b and 9c, one or more situational weights may be used to adjust the penalty values associated with each factor before the penalty values are assessed to the parties.

Figure 10A:
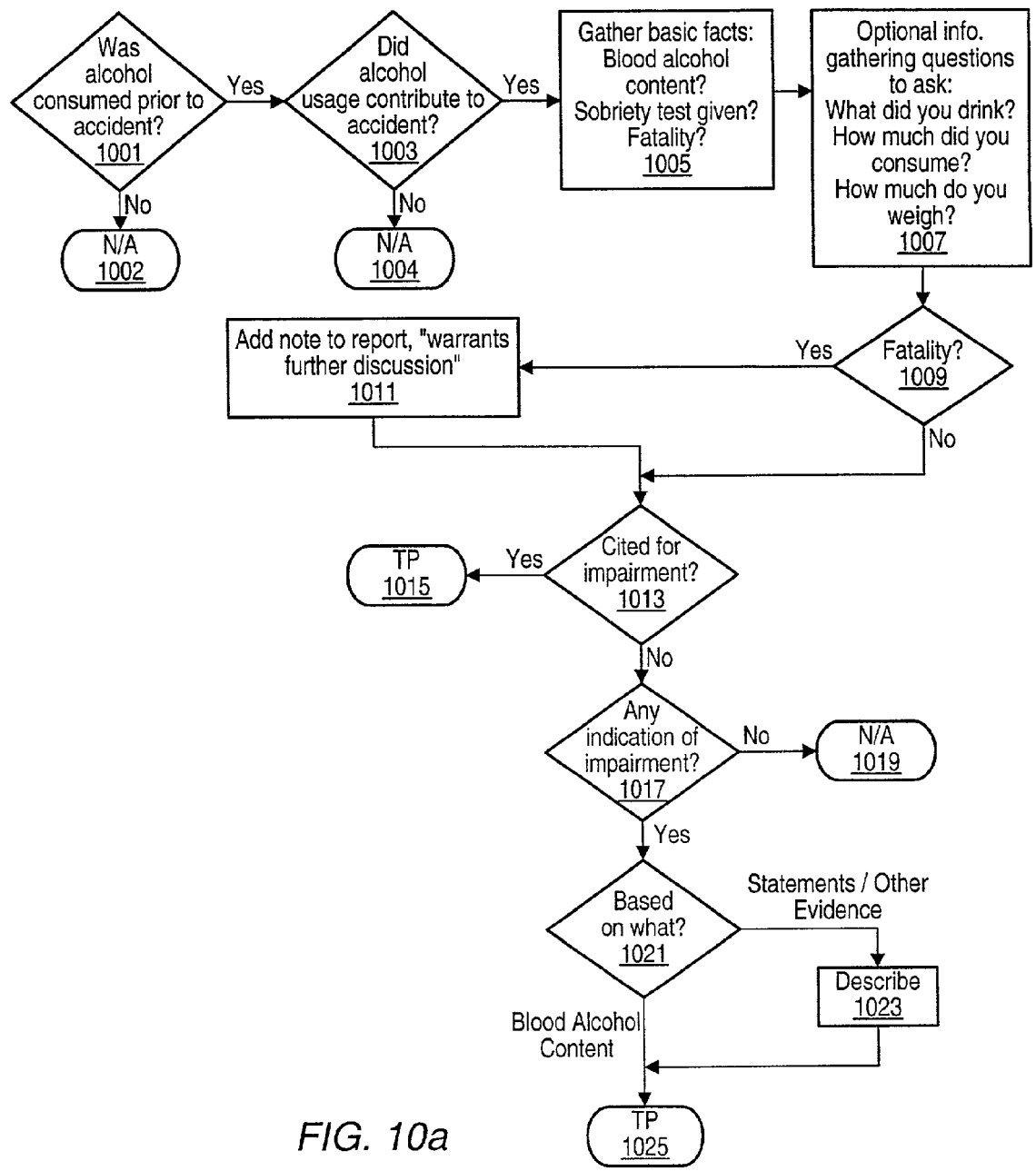
FIG. 10a is a flowchart for assessing the contribution of alcohol usage to liability in a motor vehicle accident according to a first embodiment.
Figure 10B:
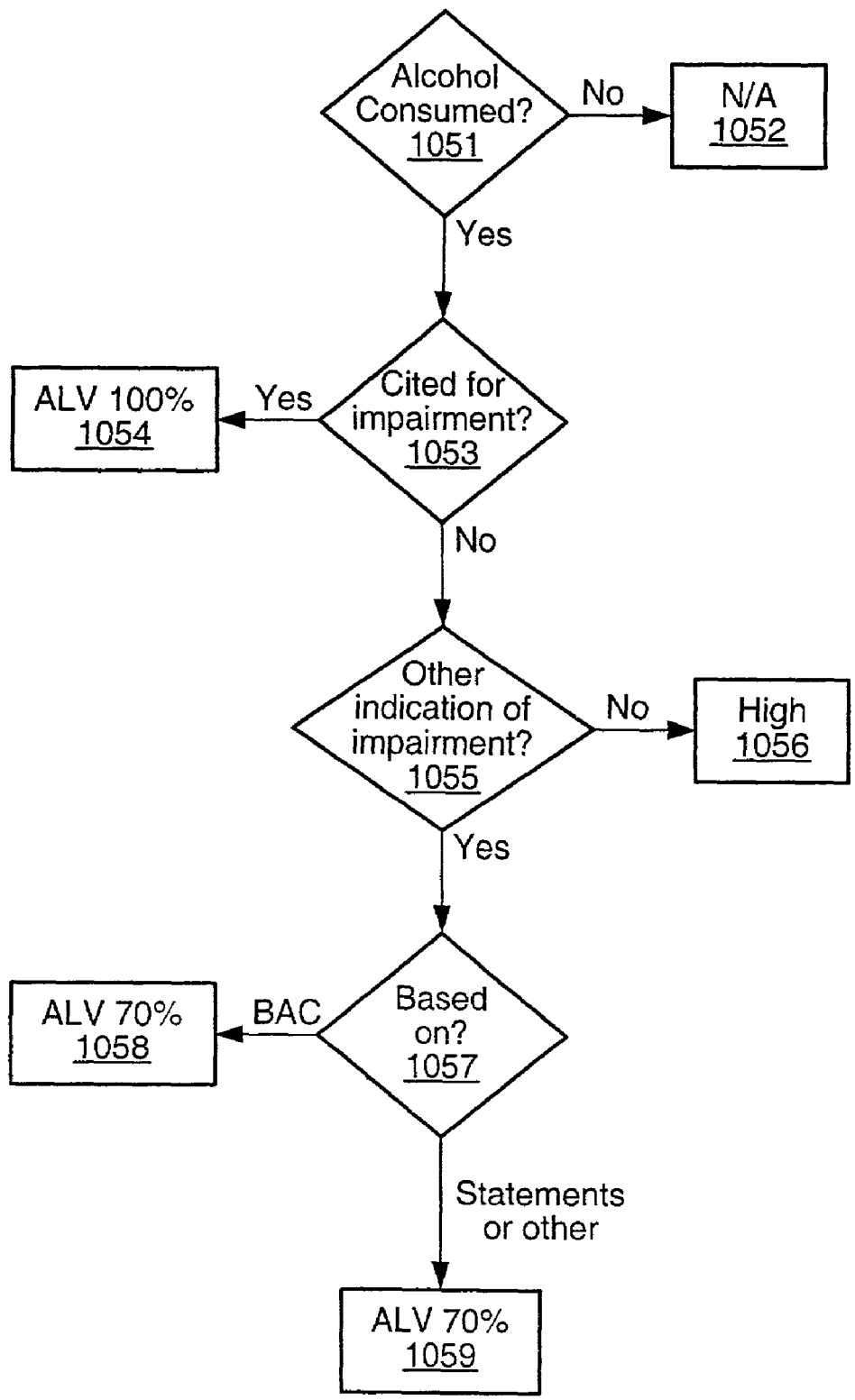
FIG. 10b is a flowchart for assessing the contribution of alcohol usage to liability in a motor vehicle accident according to a second embodiment.

FIGS. 10a and 10b depict flowcharts of alternate embodiments of methods for estimating the effect on liability of an alcohol factor In an embodiment, the alcohol factor may apply to either the tortfeasor or the other party for all accident types.

If at decision point 1001 in FIG. 10a, it is determined that alcohol was not consumed prior to the accident, then the alcohol factor may not be applicable as shown by step 1002. If alcohol was consumed prior to the accident, the next step, shown by decision point 1003, may be to determine if the alcohol usage contributed to the accident. If not, then the alcohol factor may not be applicable as shown by step 1004. If it is determined that alcohol usage did contribute to the accident, information of basic facts may be gathered as shown by step 1005. Basic information may include blood alcohol content, whether or not a sobriety test was given, and whether or not the accident involved a fatality. Optional information may also be gathered, as shown by step 1007, such as the type and amount of alcohol consumed, where the alcohol was served and by whom, and the weight of the user.

If the accident involved a fatality, as determined at decision point 1009 shown in FIG. 10a, "warrants further discussion" may be added to the accident report, as shown in step 1011. However, whether or not there was a fatality involved in the accident, the next decision point 1013 may be to determine if the user was cited for impairment. If the user was cited for impairment, a talking point may be reached, as shown by step 1015. If the user was not cited for impairment, the next decision point 1017 may be to determine if there was any indication of impairment. If there was no indication of impairment, the alcohol factor may not be applicable as shown by step 1019. If there was any indication of impairment, the next step may be to determine what the indication was based on at decision point 1021. A blood alcohol content may indicate a level of impairment. Statements or other evidence may also provide some indication of impairment, which would be described as shown by step 1023. After it is determined what the indication of impairment was based on, a talking point may be reached as shown by step 1025.

An alternate method of determining an effect on liability of alcohol is depicted in FIG. 10b. At step 1051, the method may include determining if alcohol was consumed by a driver of a vehicle involved in the accident prior to the accident. If it is determined that no alcohol was consumed prior to the accident, the factor may not apply, as shown by step 1052. If alcohol was consumed by a driver of a vehicle involved in the accident, step 1053 may determine whether the driver was cited for impairment. In certain embodiments, prior to step 1053, the method may also include a step to determine if the alcohol consumption contributed to the accident. If it is determined that the driver was cited for impairment, step 1054 may be reached and an ALV may assign 100% of the liability to the driver cited for impairment. If the driver was not cited for impairment, decision point 1055 may determine if other indications of impairment were present. If no indications of impairment were present, a "high" penalty value may be assessed to the driver that had consumed alcohol, as depicted in step 1056. If indications of impairment were present, the method may determine the nature of the indications of impairment at step 1057. Indications of impairment based on blood alcohol content (step 1058), or statements or other evidence (step 1059) may result in a penalty value of 70% of the liability to the impaired driver.

Figure 11:
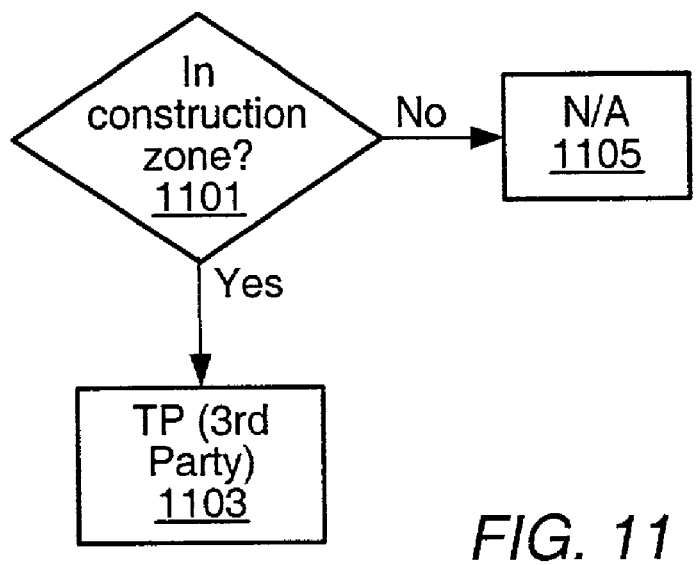
FIG. 11 is a flowchart for assessing the contribution of a construction zone to liability in a motor vehicle accident according to one embodiment.

FIG. 11 is a flowchart illustrating a method for estimating the effect on liability of a factor that accounts for the presence of a construction zone on a motor vehicle accident according to one embodiment. The construction zone factor may be applied to a tortfeasor and/or other party for any accident type.

If a motor vehicle accident occurred in a construction zone where a third party, other than the driver(s) or vehicle(s) involved in the accident may be involved, as determined at decision point 1101 in FIG. 11, then a talking point may be reached at step 1103. If the accident did not occur in a construction zone, then the factor may not be applicable in estimating liability, as shown by step 1105.

Figure 12:
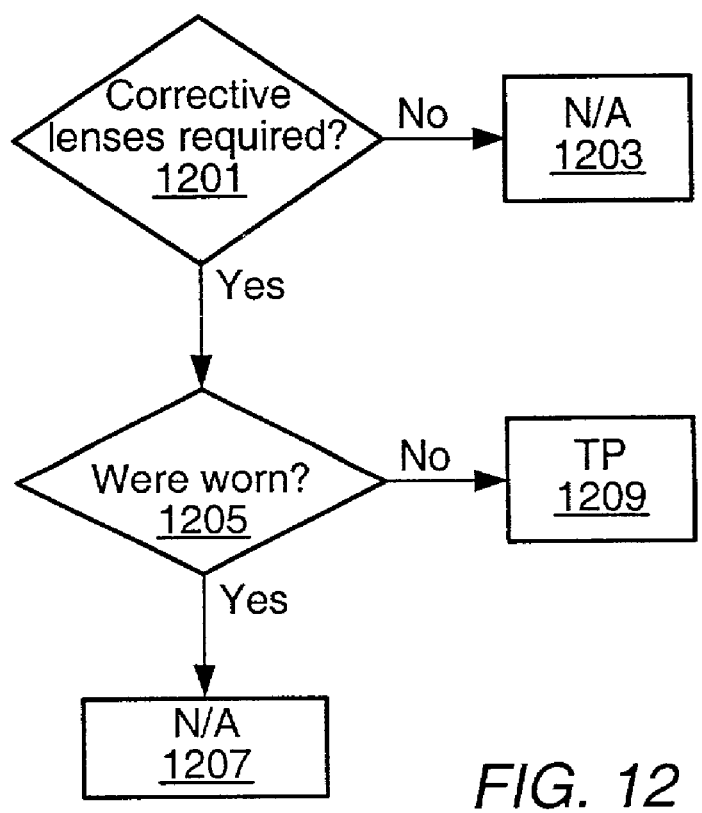
FIG. 12 is a flowchart for assessing the contribution of corrective lenses to liability in a motor vehicle accident according to one embodiment.

FIG. 12 is a flowchart for estimating the effect on liability of a factor that accounts for corrective lenses in a motor vehicle accident according to one embodiment. The corrective lenses factor may be applied to a tortfeasor and/or other party for any accident type.

If it is determined at decision point 1201 in FIG. 12 that a driver involved in a motor vehicle accident did not require corrective lenses, then the factor may not be applicable as shown by step 1203. If corrective lenses were required, the next decision point 1205 may be to determine whether they were worn at the time of the accident. If the corrective lenses were worn at the time of the accident, the factor may not be applicable in estimating liability, as shown by step 1207. If required corrective lenses were not worn by the driver at the time of the accident, a talking point may be reached as shown by step 1209.

Figure 13:
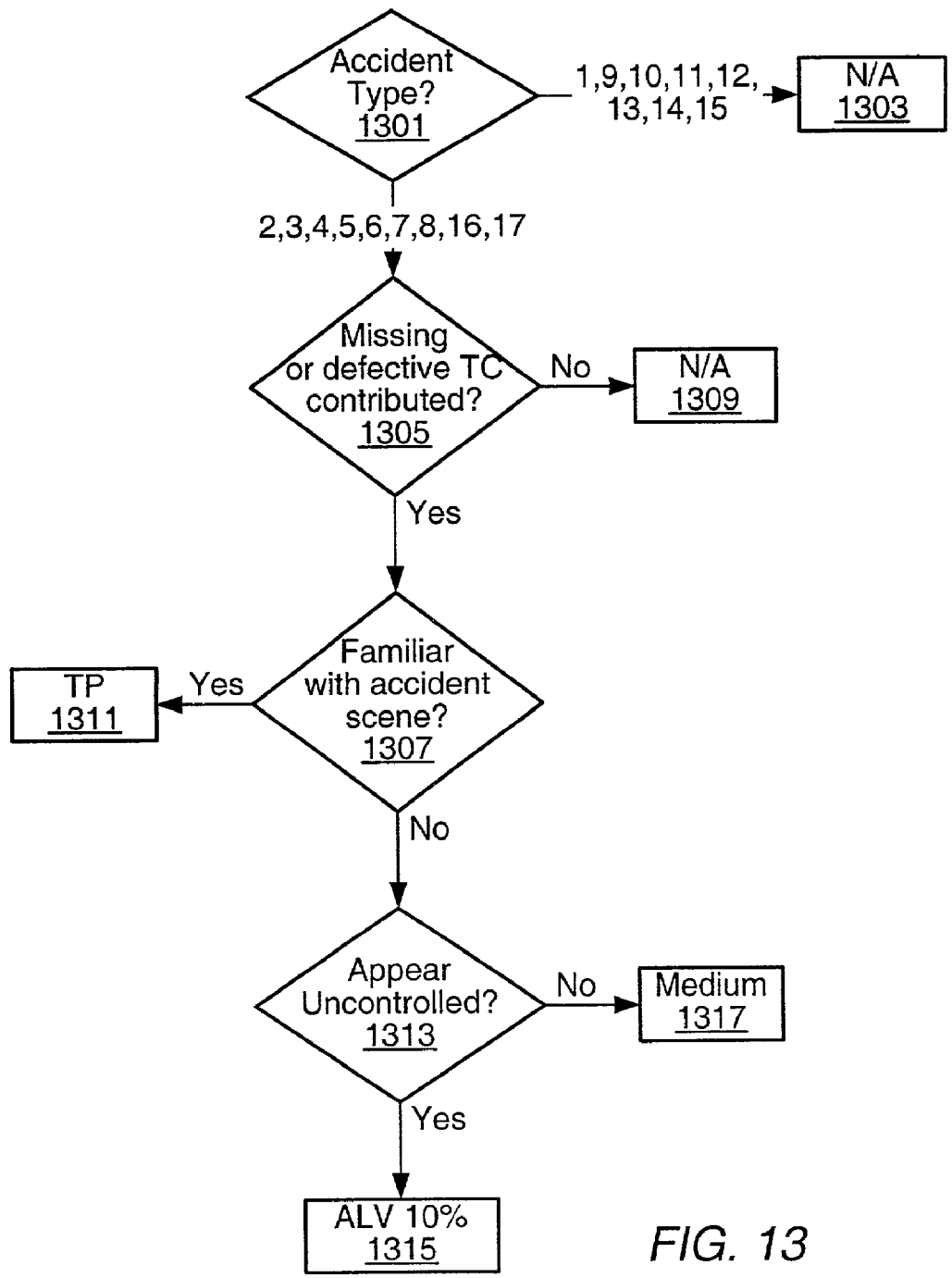
FIG. 13 is a flowchart for assessing the contribution of defective, obscured, or missing traffic control to liability in a motor vehicle accident according to one embodiment.

FIG. 13 is a flowchart for estimating the effect on liability of a factor that accounts for a defective, obscured, or missing traffic control on a motor vehicle accident according to one embodiment. The traffic control may be missing or completely obscured. A defective light may be one that may not be lit for either party (e.g., not lit for TF or not lit for OP). The traffic control factor may be applied to a tortfeasor and/or other party for accident types 2, 3, 4, 5, 6, 7, 8, 16, and 17.

If at decision point 1301 shown in FIG. 13, the accident type was determined to be 1, 9, 10, 11, 12, 13, 14, or 15, then the traffic control factor may not be applicable to estimating liability, as shown by step 1303. For accident types 2, 3, 4, 5, 6, 7, 8, 16, and 17, a decision point shown by step 1305 may be reached to determine if an obscured, defective, or missing traffic control contributed to the accident. If an obscured, defective, or missing traffic control did not contribute to the accident, then the factor may not applicable for estimating liability, as shown in step 1309.

If it is determined that an obscured, defective, or missing traffic control contributed to the accident, then decision point 1307 may be reached to determine if a driver was familiar with the accident location. If the answer is yes, then a talking point may be reached as shown by step 1311. If the answer is no, the next decision point 1313 may be whether or not the intersection appeared to be an uncontrolled intersection. If not, a "medium" penalty value may be assessed to the party in question, as shown in step 1317. If the intersection appeared to be a controlled intersection, an ALV of 10% may be assessed to the party in question.

Figure 14:
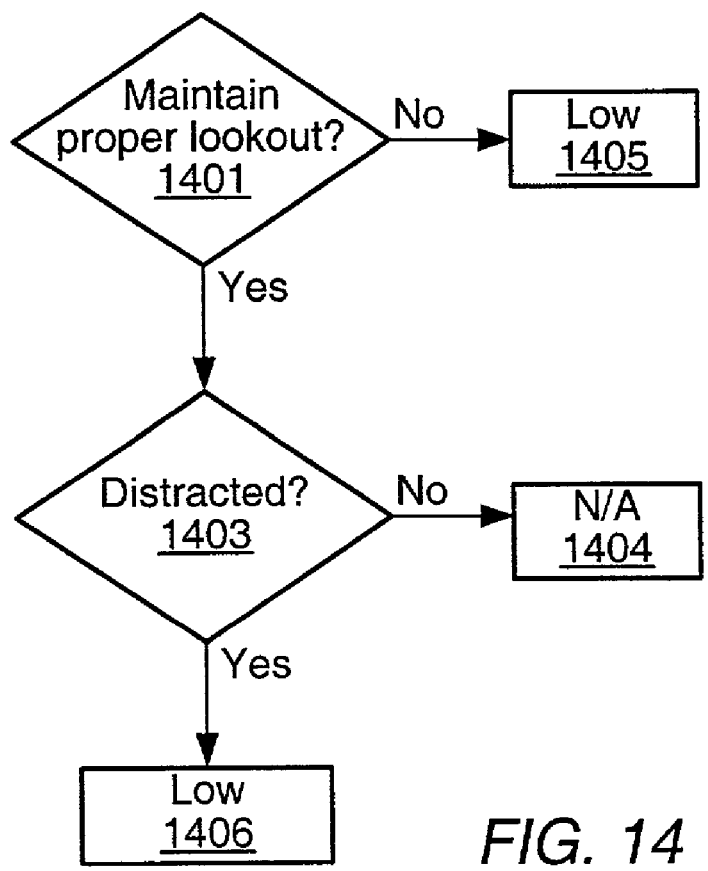
FIG. 14 is a flowchart for estimating the contribution of driver inattention to liability in a motor vehicle accident according to one embodiment.

FIG. 14 is a flowchart for estimating the effect on liability of a factor that accounts for the contribution of driver inattention to a motor vehicle accident according to one embodiment. The driver inattention factor may be applied to a tortfeasor and/or other party for any accident type.

As shown by decision point 1401 in FIG. 14, if the driver failed to maintain a proper lookout (e.g., not looking at the road ahead), then a "low" penalty value may be assessed against the driver, as shown in step 145. If the driver maintained a proper lookout, the step 1403 may be reached. Step 1403 may determine if the driver was distracted prior to the accident (e.g., by a conversation, a cell phone, shaving, etc.). If the driver was distracted, then a "low" penalty value may be assessed to the driver at step 1406. If the driver was not distracted then, as step 1404 indicates, the factor may be not applicable for the driver.

Figure 15:
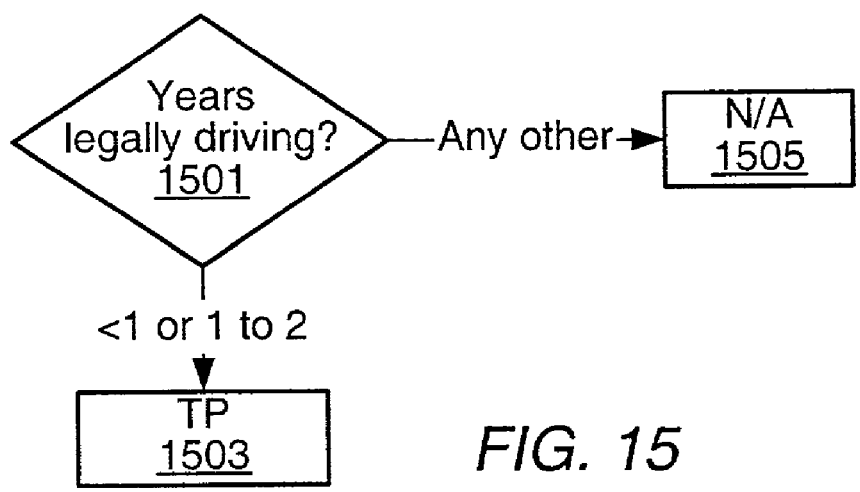
FIG. 15 is a flowchart for estimating the contribution of driver inexperience to liability in a motor vehicle accident according to one embodiment.

FIG. 15 is a flowchart for estimating the effect on liability of a factor that accounts for the contribution of driver inexperience to a motor vehicle accident according to one embodiment. The driver inexperience factor may be applied to a tortfeasor and/or other party for any accident type.

As shown by decision point 1501 in FIG. 15, the duration of time the driver has been legally driving may be a determining factor. If the driver has been driving for two years or less, then the factor may be a talking point as shown by step 1503. If the driver has been driving for more than two years, then the driver inexperience factor may not be applicable as shown by step 1505. In some embodiments, decision point 1501 may be directed to how long a driver has been legally driving a particular class of vehicle that was involved in the accident. For example, if the driver was driving a motorcycle at the time of the accident, decision point 1501 may determine how long the driver has been legally driving motorcycles.

Figure 16:
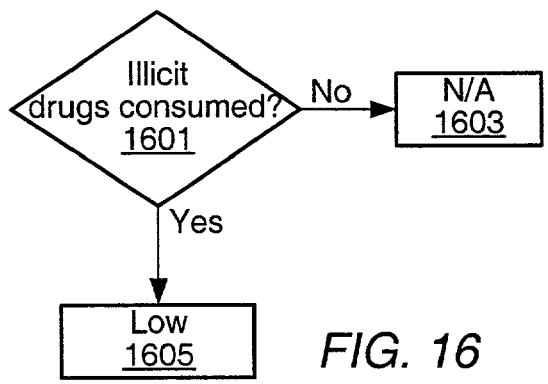
FIG. 16 is a flowchart for estimating the contribution of taking an illicit drug to liability in a motor vehicle accident according to one embodiment.

FIG. 16 is a flowchart for estimating the effect of a factor that accounts for the contribution of taking an illicit drug to a motor vehicle accident according to one embodiment. The illicit drug factor may be applied to a tortfeasor and/or other party for any accident type. As used herein, the term "illicit drug" generally refers to an illegal, or unlawfully used drug. For example, an unlawfully used drug may include a prescription drug taken in a fashion other than the prescribed manner or a prescription drug taken by a person to whom it has not been prescribed.

Decision point 1601 in FIG. 16 may determine if an illicit drug was consumed prior to the accident. If no illicit drug was taken before the accident, the illicit drug factor may be not applicable, as shown in step 1603. If an illicit drug was taken prior to the accident, a "low" penalty value may be assessed to the party that took the illicit drug, as shown in step 1605.

In other embodiments, factors accounting for the consumption of illicit drugs and the consumption of alcohol may be treated simultaneously through an alcohol factor flow chart as depicted in FIGS. 10*a* and 10*b*.

Figure 17:
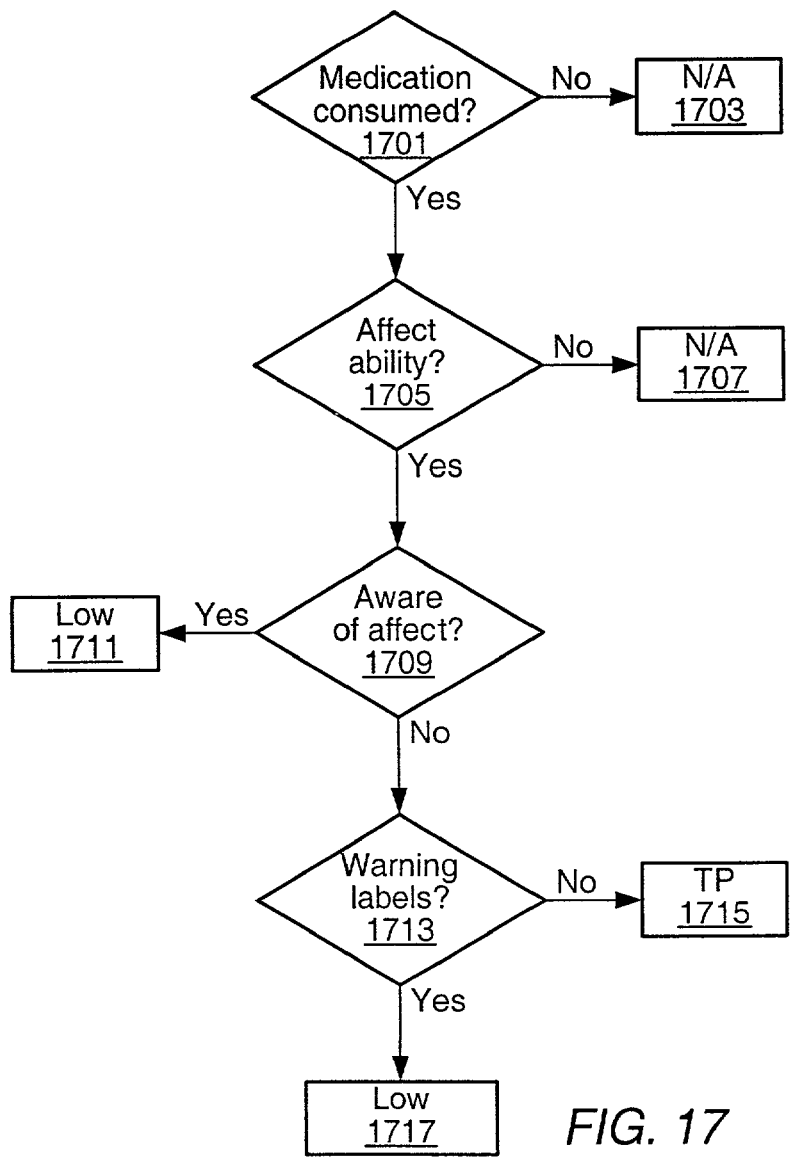
FIG. 17 is a flowchart for estimating the contribution of taking a medication to liability in a motor vehicle accident according to one embodiment.

FIG. 17 is a flowchart for estimating the effect of a factor that accounts for the contribution of an affirmative action of taking a medication to a motor vehicle accident according to one embodiment. The medication factor may be applied to a tortfeasor and/or other party for any accident type. In an embodiment, the medication factor may not include failing to take required medicine since the illness factor may take this into account. As used herein, the term "medication" generally refers to either a prescription drug, or an over-the-counter drug. Additionally, in some embodiments, a medication may include any legal chemical substance that may be consumed by an individual for medical reasons (e.g., herbs, or other nontraditional medications).

At decision point 1701 in FIG. 17, it is determined whether a medication was taken prior to the accident. If not, as shown by step 1703, then the medication factor may not be applicable. If a medication was taken prior to the accident, then the next decision point 1705 may determine if the medication had an affect on the ability to drive. If not, then the factor may not be applicable, as shown by step 1707.

If the medication affected the ability to drive, it may then be determined if the party was aware of this effect, as shown by decision point 1709. If the party was aware of the effect of the medication on the ability to drive, then a "low" penalty value may be assessed for the medication factor, as shown by step 1711. If the party was not aware of the effect of the medication on the ability to drive, then decision point 1713 may ask if the medication had appropriate warnings and labels. If there were not proper warnings or labels on the medication, then the factor may be a talking point as shown by step 1715. In some embodiments, if there were not proper warnings or labels on the medication, step 1715 may indicate that a portion of the liability may be attributed to a third-party (e.g., the medication vendor, or manufacturer). If the medication was properly labeled, then a "low" penalty value may be assessed to the party as shown by step 1717.

Figure 18:
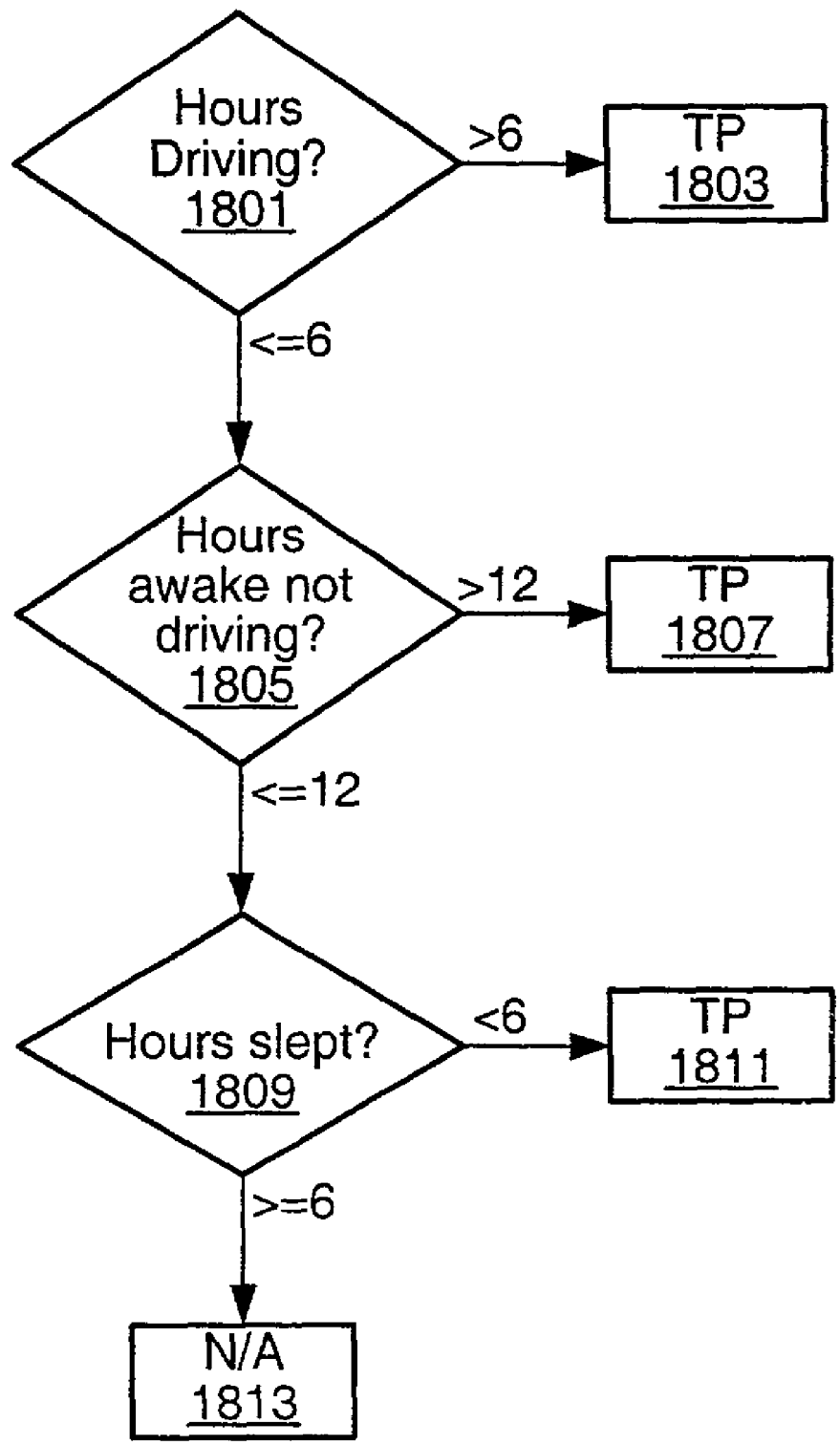
FIG. 18 is a flowchart for estimating the contribution of fatigue to liability in a motor vehicle accident according to one embodiment.

FIG. 18 is a flowchart for estimating the effect of a factor that accounts for the contribution of fatigue to a motor vehicle accident according to one embodiment. The fatigue factor may be applied to a tortfeasor and/or other party for any accident type.

At decision point 1801 in FIG. 18, the number of hours the party had been driving may be determined. If the driver had been driving for more then 6 hours, then the factor may be a talking point as shown by step 1803. If the driver had been driving for 6 hours or less, then decision point 1805 asks how long the driver had been awake, but not driving. If the driver was awake but not driving for more than 12 hours, then the factor may be a talking point as shown by step 1807. If the driver was awake for 12 hours or less prior to driving, then the number of hours the driver last slept may be determined at decision point 1809. If the driver slept less than 6 hours, the factor may be a talking point, as shown by step 1811. If the driver slept 6 hours or more, then the fatigue factor may not be applicable, as shown by step 1813.

Figure 19:
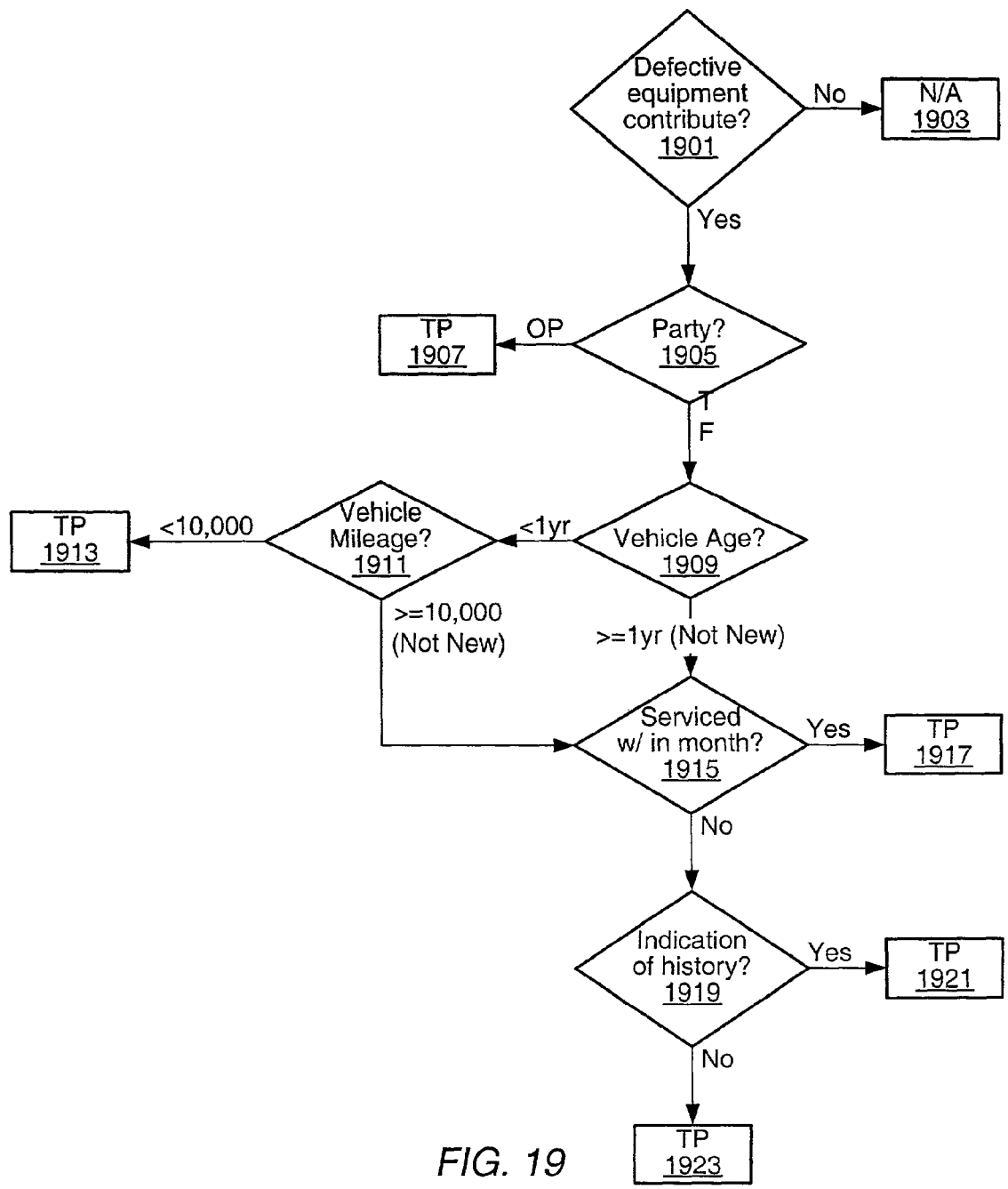
FIG. 19 is a flowchart for estimating the contribution of faulty equipment to liability in a motor vehicle accident according to one embodiment.

FIG. 19 is a flowchart for estimating the effect of a factor that accounts for the contribution of faulty equipment to a motor vehicle accident according to one embodiment. As used herein, the term "faulty equipment" generally refers to any vehicle equipment malfunction that causes an action, prohibits the operator from taking action, or fails to perform an action. In an embodiment, the faulty equipment factor may not apply to headlights, taillights, or brake lights that do not function as other factors may be provided that account for these potential equipment failures. The faulty equipment factor may be applied to a tortfeasor and/or other party for any accident type.

Decision point 1901 may ask whether defective equipment contributed to the accident, as depicted in FIG. 19. If defective equipment did not contribute to the accident, then the faulty equipment factor may not be applicable, as shown in step 1903. If defective equipment contributed to the accident, the next step may be decision point 1905, which may determine the party that faulty equipment affected. If the faulty equipment affected the other party, as shown in step 1907, then a talking point may be reached. If the faulty equipment affected the tortfeasor, the next step may be decision point 1909, which may determine the age of the vehicle.

If the vehicle was one year old or greater, then the vehicle may not be considered new. If the vehicle was less than one year old, then the next decision point 1911 may ask the mileage on the vehicle. If the vehicle mileage was less than 10,000 miles at the time of the accident, the vehicle may be considered new. If the vehicle mileage was 10,000 miles or greater at the time of the accident, the vehicle may not be considered new.

In some embodiments, if the vehicle was new, then step 1913 may be a talking point. Alternately, in some embodiments, step 1913 may indicate that the faulty equipment may be attributed to a third party. The third party may include the person or entity from which the vehicle was purchased or serviced. If the vehicle was not considered new by steps 1909 or 1911, the next step may be decision point 1915 that may ask whether the defective part was serviced within the last month. If service was performed on the defective part within the last month, a talking point may be reached, as shown by step 1917. In some embodiments, step 1917 may be an ALV of 0% for the driver of the vehicle with the defective part. In some embodiments, at least a portion of the liability for the accident may be attributed to a third party at step 1917. For example, the third party may be an individual or entity that last serviced the defective part. The third party may also include the manufacturer of the defective part. If the defective part was not serviced within the last month, decision point 1919 may ask if there was any indication or history of the problem. Whether or not there was an indication or history of the problem, the faulty equipment factor may reach a talking point as shown by steps 1921 and 1923. Steps 1921 and 1923 may be indicated differently in an assessment report as discussed with reference to FIG. 55. In alternate embodiments, if there was no indication or history of the problem at step 1919, another decision point may be reached. The decision point may be to determine whether or not unwanted acceleration occurred. If not, then a talking point may be reached and noted in the assessment report. However, if an unwanted acceleration did occur, the driver of the affected vehicle may be assessed an ALV of 0% liability. Additionally, a portion of the liability may be assessed to a third party. For example, the third party may include a manufacturer or seller of the vehicle or the defective part.

Figure 20A:
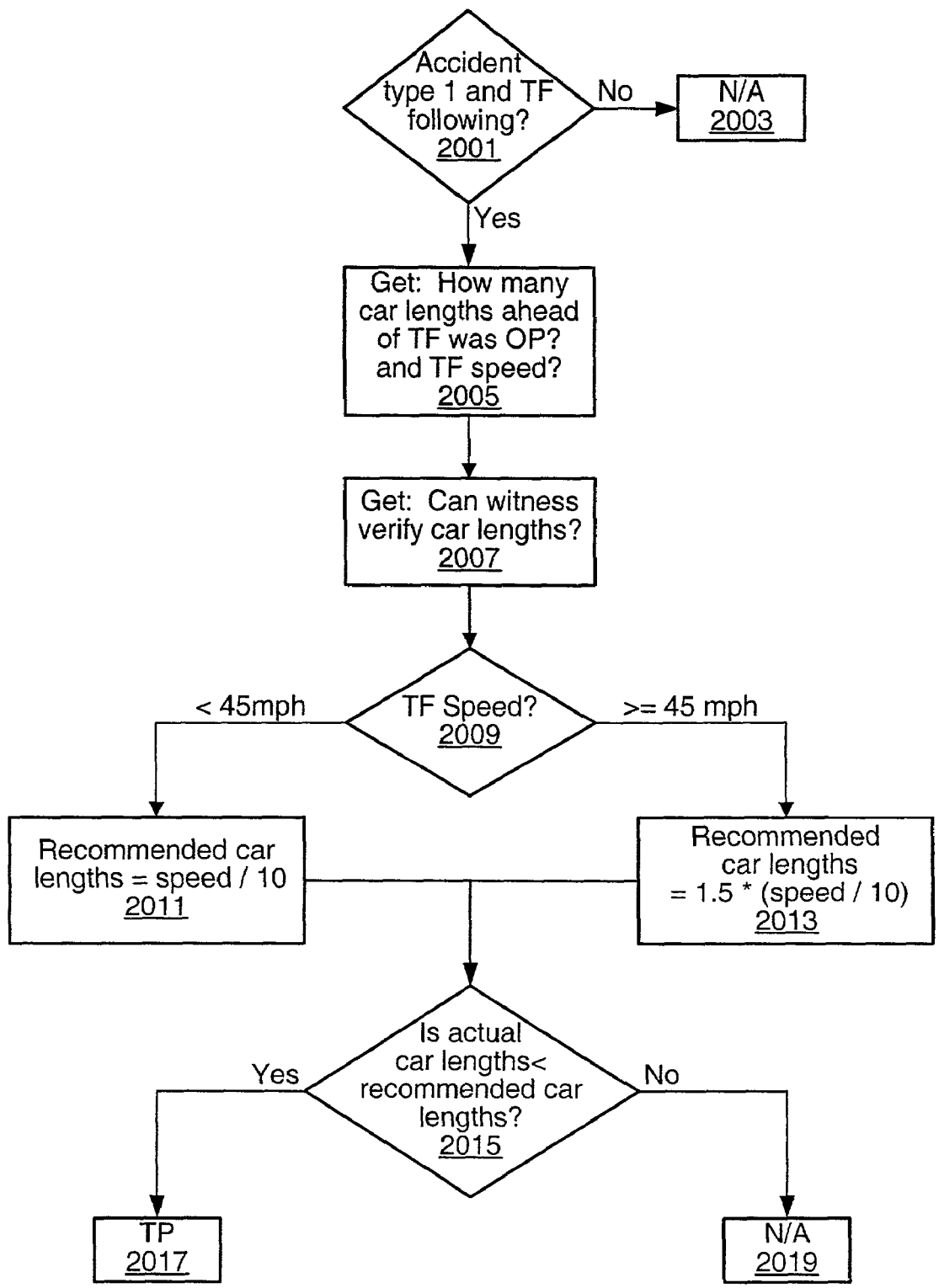
FIG. 20a is a flowchart for estimating the contribution of following too closely to liability in a motor vehicle accident according to a first embodiment.

FIG. 20a is a flowchart for estimating the effect of a factor that accounts for the contribution of following too closely to a motor vehicle accident according to a first embodiment. As used herein, the term "following too closely" generally refers to an action by the driver of a rear vehicle in which the driver of the rear vehicle fails to remain a safe distance from a vehicle in front of them before the accident, thus contributing to the accident. In some embodiments, the following too closely factor may be applied only to the tortfeasor and may only be applied for accident type 1.

As shown by decision point 2001 in FIG. 20a, if the accident type was not type 1 or the tortfeasor was not behind or following the other party, then the factor may not be applicable as shown by step 2003. If the accident type was type 1 and the tortfeasor was following the other party, then the next step 2005 may be to gather information regarding the accident. The information may include the number of car lengths between the other party and the tortfeasor before the accident, and the speed that the tortfeasor was traveling. Additionally, as shown by step 2007, information may be gathered from any witnesses who may verify the number of car lengths that were between the other party and the tortfeasor.

The next decision point 2009 may ask for the speed of the tortfeasor. The speed of the tortfeasor may be used to determine a recommended safe following distance the tortfeasor should have been traveling behind the other party in steps 2011 or 2013. For example, if the tortfeasor was traveling less than 45 mph, then the recommended safe following distance in car lengths may be determined by: speed/10, as shown by step 2011. If the tortfeasor was traveling 45 mph or greater, the recommended safe following distance may be: 1.5* (speed/10), as shown by step 2013. From this determination, the decision point 2015 may ask whether the actual number of car lengths was less than the recommended safe following distance. If the actual car lengths were less than the recommended safe following distance, then the factor may be a talking point as shown by step 2017. If the actual car lengths between the tortfeasor and other party were not less than the recommended safe following distance, then the following too closely factor may not be applicable, as shown by step 2019.

Figures 20B, 20C:
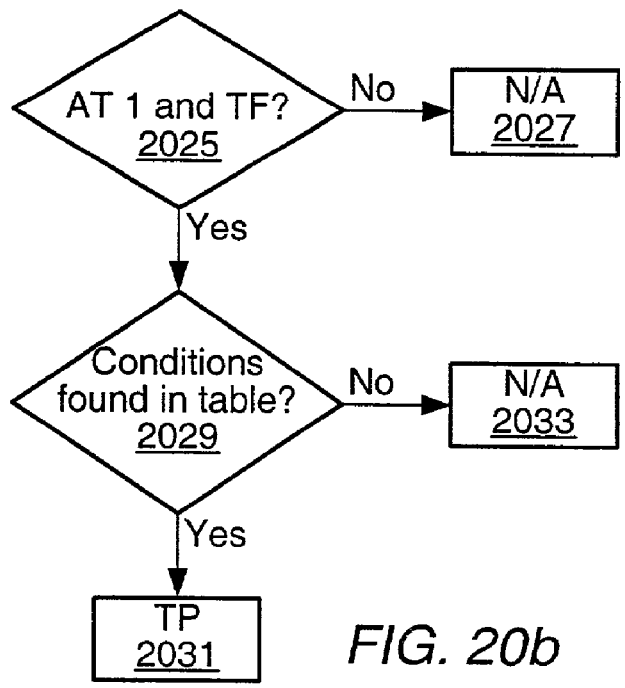
FIG. 20b is a flowchart for estimating the contribution of following too closely to liability in a motor vehicle accident according to a second embodiment.
FIG. 20c is a table for estimating the contribution of following too closely to liability in a motor vehicle accident according to the embodiment illustrated in FIG. 20b.

FIG. 20b is a flowchart for estimating the effect of a factor that accounts for the contribution of following too closely to a motor vehicle accident according to a second embodiment. As shown by decision point 2025 in FIG. 20b, if the accident type was not type 1 or the tortfeasor was not behind or following the other party, then the factor may not be applicable as shown by step 2027. If the accident type was type 1 and the tortfeasor was following the other party, then the next step 2029 may be to determine if the actual following distance was less than a recommended safe following distance according to the table in FIG. 20c.

FIG. 20c depicts a table for determining a recommended safe following distance. If the driver of the rear vehicle was traveling at less than or equal to 45 mile per hour (mph), then row 2050 may be used to determine the recommended safe following distance. If the driver of the rear vehicle was traveling at greater than 45 mph, then row 2052 may be used to determine the recommended safe following distance. Column 2054 may determine a surface of the road.

At speeds of less than or equal to 45 mph and with a gravel road surface the recommended safe following distance may be at least 20% of the speed in car lengths (e.g., speed*0.2=number of car lengths). Thus, at 40 mph, the recommended safe travel distance may be 8 car lengths (i.e., 40*0.2=8 car lengths). At speeds of greater than 45 mph and with a gravel road surface the recommended safe following distance may be at least 30% of the speed in car lengths.

For non-gravel road surfaces, a condition of the road surface may be considered in column 2056. The condition of the road surface may include, but is not limited to, dry, wet, or muddy. In addition, the condition of the road surface may consider whether the road is covered with snow or ice, has patches of snow or ice, or has plowed snow or ice. In various embodiments, other road conditions may also be considered.

For example, a road condition that may be prevalent in a particular region may be considered, such as having ruts. Once the road condition has been determined, a recommended safe following distance may be determined based on a percentage of the speed as specified in column 2058. It is envisioned that the specific percentage of speed specified by various combinations of speed, road surface, and road condition may be varied according to the preference of the insurance carrier, or regional or jurisdictional preferences.

Figure 21:
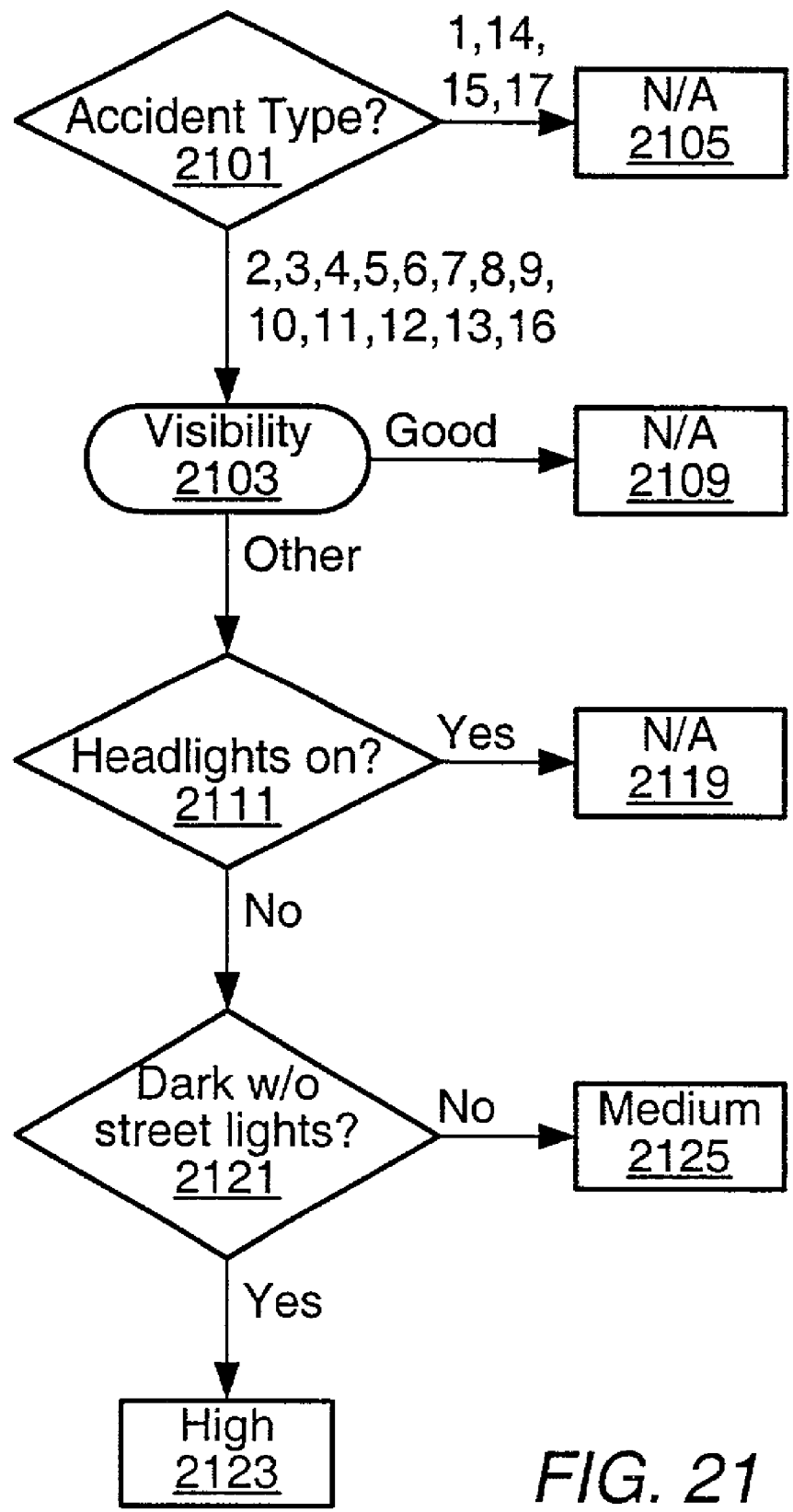
FIG. 21 is a flowchart for estimating the contribution of headlights being off to liability in a motor vehicle accident according to one embodiment.

FIG. 21 is a flowchart for estimating the effect of a factor that accounts for the contribution of driving with headlights off to a motor vehicle accident according to one embodiment. In some embodiments, the headlights off factor may not apply to accident types 1, and 14. The factor may be applied to a tortfeasor and/or other party.

Figure 35:
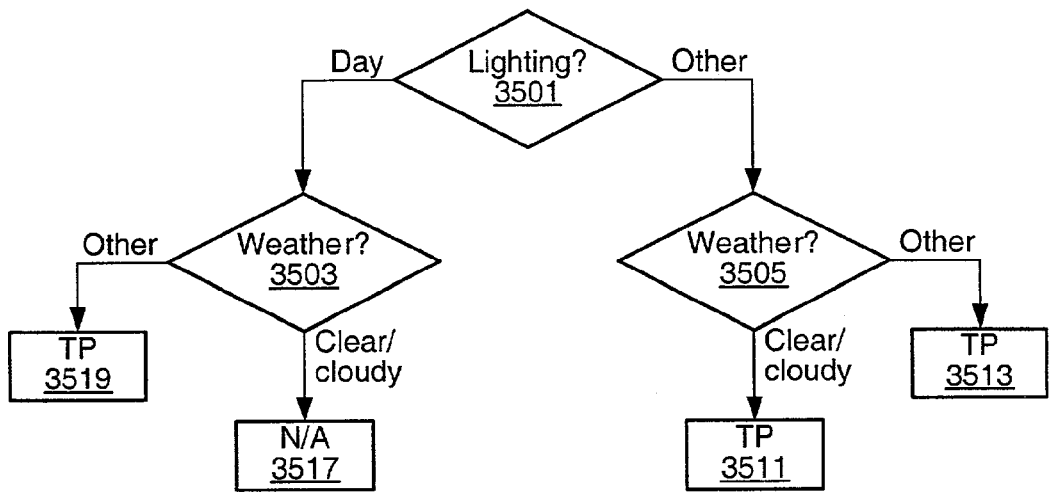
FIG. 35 is a flowchart for estimating the contribution of visibility to liability in a motor vehicle accident according to one embodiment.

In FIG. 21, decision point 2101 asks for the accident type. For accident types 1, and 14, the factor may not be applicable as shown by step 2105. Additionally, in some embodiments, the factor may not apply for accident types 15 and 17. For the remaining accident types, the next step may be decision point 2103 in which visibility at the time of the accident may be determined. The visibility factor is illustrated in FIG. 35. If visibility was good, then the driving with headlights off factor may not be applicable as shown by step 2109. Otherwise, if visibility was poor, decision point 2111 may determine if the party was driving with the vehicle's headlights on. If it is determined that the party had the headlights on, then the factor may not be applicable, as shown by step 2119. If the vehicle's headlights were off at the time of the accident, then decision point 2121 may be reached. Decision point 2121 asks whether the location of the accident was relatively dark, for example, without streetlights at the time. If it was dark without streetlights, the party may have a "high" penalty value assessed, as shown by step 2123. If it was not dark and/or streetlights were on, then the other party may have a "medium" penalty value assessed, as shown by step 2125.

In some embodiments, the method of determining the effect on liability of driving with headlights off may determine different penalty values depending on the party being considered. For example, if it is determined that the tortfeasor was driving with headlights off, a talking point may be reached. If it is determined that the other party was driving with headlights off, then penalty values as described above may be assessed to the other party.

In some embodiments, the method of determining the effect on liability of driving with headlights off may determine if both headlights were off or if only one headlight was off. If only one headlight was on, the method may determine if the one headlight would have provided adequate lighting for the driver of the vehicle to drive safely. If it is determined that the one headlight may not have provided adequate lighting, the method may proceed to step 2121 to determine a penalty value to assess. The method may also consider whether the one headlight would have made the vehicle visible to the driver of the other vehicle (e.g., was the one working headlight visible to the driver of the other vehicle). If it is determined that the one headlight may not have made the vehicle visible to the driver of the other vehicle, the method may proceed to step 2121 to determine a penalty value to assess.

Figure 22:
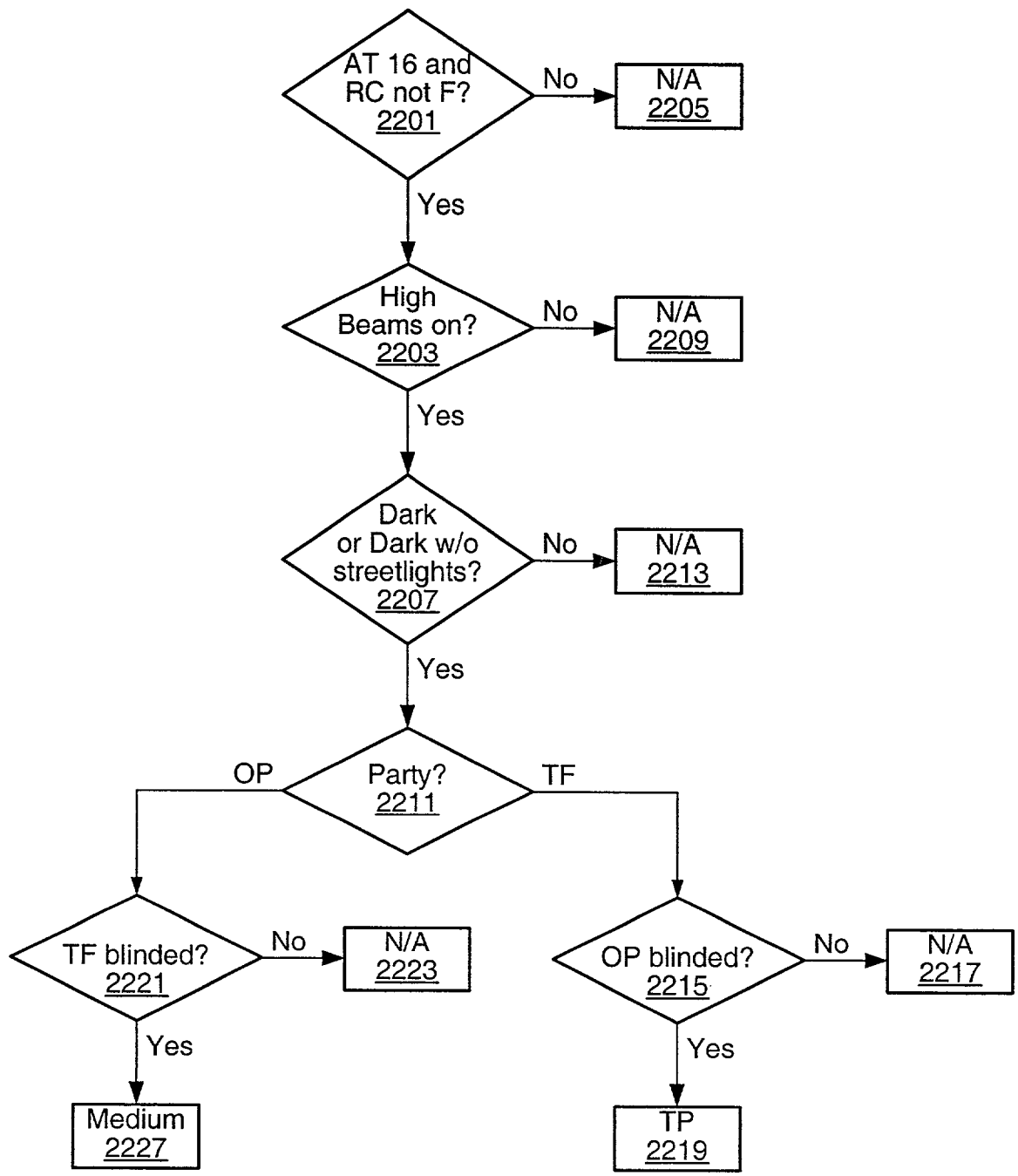
FIG. 22 is a flowchart for estimating the contribution of high beams being on to liability in a motor vehicle accident according to one embodiment.

FIG. 22 is a flowchart for estimating the effect of a factor that accounts for the contribution of driving with high beams on to a motor vehicle accident according to one embodiment. The high beams factor may be applied to a tortfeasor and/or the other party. In some embodiments, the factor may only be applied for accident type 16. In such embodiments, the factor may not be applied for the roadway configuration/accident type combination F16. The high beams factor may be related to glare that causes a driver to be blinded.

In FIG. 22, decision point 2201 and step 2205 indicate the factor may only be applicable for accident type 16, not including roadway configuration F. If the answer to decision point 2201 is yes, then decision point 2203 may ask whether high beams were on at the time of the accident. If not, then the factor may not be applicable, as shown by step 2209. If the high beams were on, the lighting may be determined at step 2207. If the lighting was dark, with or without streetlights, then liability may depend upon which party is being considered, as shown by decision point 2211. If the lighting was other than dark, with or without streetlights (e.g., daylight, dawn, or dusk) then the factor may not be applicable, as shown by step 2213. If the party is the tortfeasor, then decision point 2215 may ask whether the other party was blinded. If the other party was blinded, then the factor may be a talking point, as shown by step 2219. If the other party was not blinded, then the factor may not be applicable, as shown by step 2217. In other embodiments, a "medium" penalty value may be assessed to the tortfeasor if the other party was blinded, and a "low" penalty value may be assessed if the other party was not blinded.

If the party is the other party, then decision point 2221 may ask if the tortfeasor was blinded. If not, then the factor may not be applicable, as shown by step 2223. If the tortfeasor was blinded, the factor may apply a "medium" penalty value, as shown in step 2227. In alternate embodiments, if the tortfeasor was blinded, then another decision point may be reached that may depend on the roadway configuration. If the roadway configuration was E, then a "medium" penalty value may be assessed. If the roadway configuration was A, B, or H, then a "low" penalty value may be assessed. If the roadway configuration was other than A, B, E, or H, than the factor may not be applicable.

Figure 23:
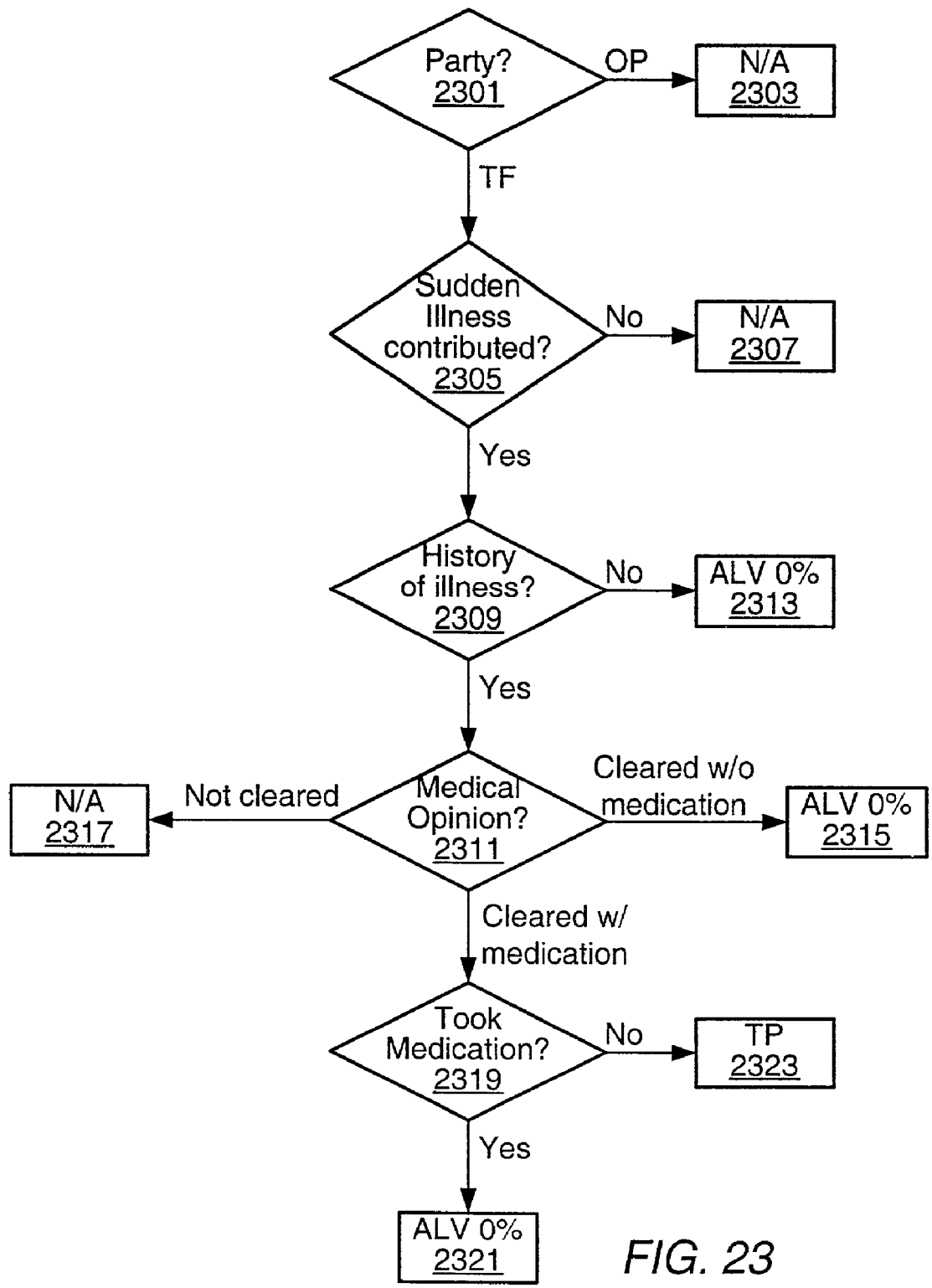
FIG. 23 is a flowchart for estimating the contribution of illness to liability in a motor vehicle accident according to one embodiment.

FIG. 23 is a flowchart for estimating the effect of a factor that accounts for the contribution of illness to a motor vehicle accident according to one embodiment. As used herein, the term "illness" generally refers to a physical condition that prohibits the safe operation of a vehicle. The illness factor may be applied to a tortfeasor only for any accident type.

If the party is determined to be the other party at decision point 2301 in FIG. 23, then the factor may not be applicable, as shown by step 2303. For the tortfeasor, the next step is decision point 2305, which may ask whether the illness contributed to the accident. If not, then the factor may not be applicable as shown by step 2307. If illness of the tortfeasor contributed to the accident, then decision point 2309 may ask if the tortfeasor had a history of the illness. If not, then an ALV of 0% liability may be assessed to the tortfeasor. If the tortfeasor had a history of illness, then decision point 2311 may ask if the tortfeasor was medically cleared to drive. If the tortfeasor was not cleared to drive, then the illness factor may not be applicable as shown by step 2317. If the tortfeasor was cleared to drive without medication, then an ALV of 0% liability may be assessed to the tortfeasor, as shown by step 2315. If the tortfeasor was medically cleared to drive with medication, then decision point 2319 may be reached, which may ask if the required medication had been taken. If the required medication had been taken, then an ALV of 0% liability may be assessed to the tortfeasor, as shown by step 2321. If the required medication had not been taken, then 2323 indicates that a talking point may be reached.

Figure 24A:
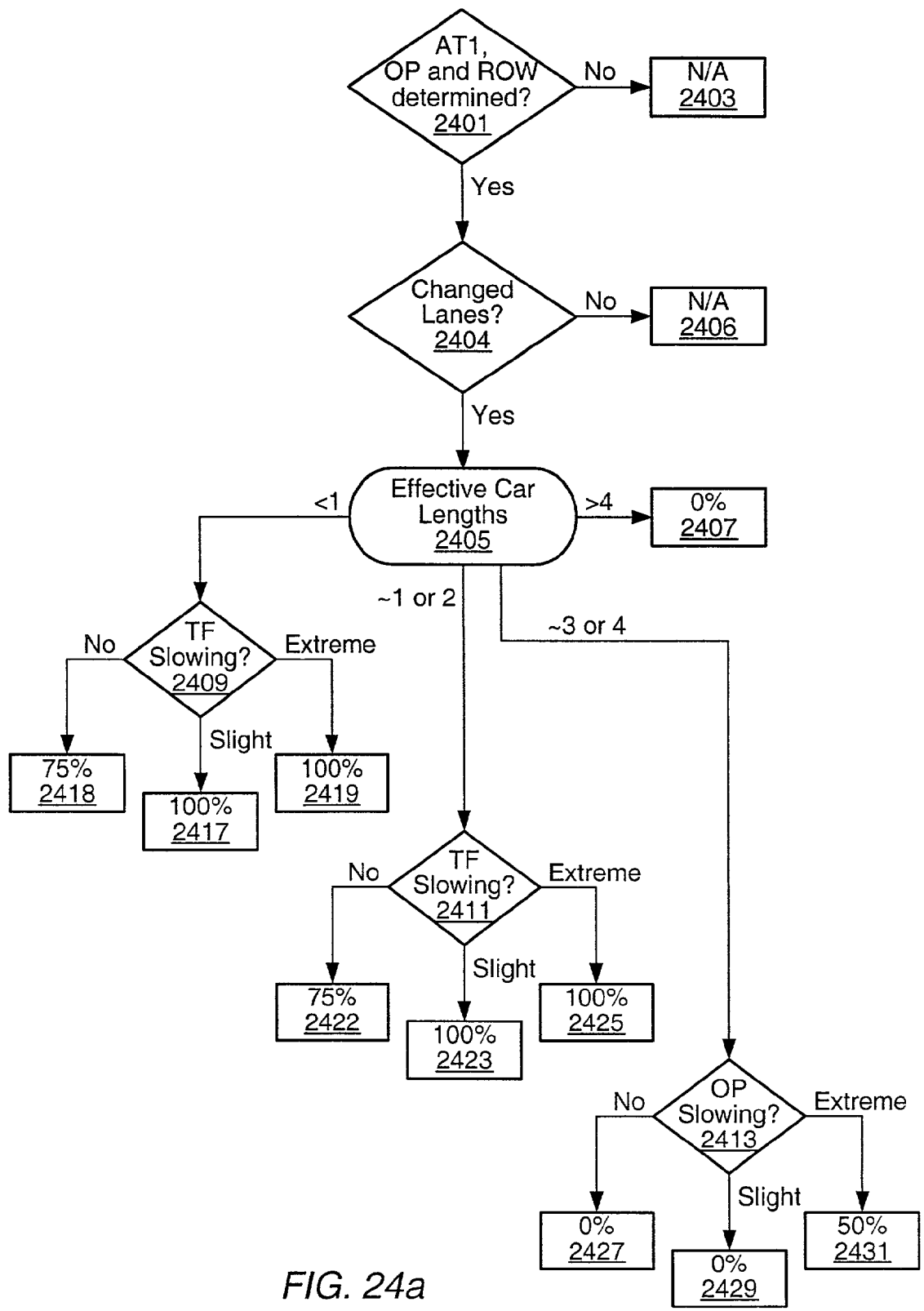
FIG. 24a is a flowchart for estimating the contribution of an improper lane change to liability in a motor vehicle accident according to one embodiment.
Figure 24B:
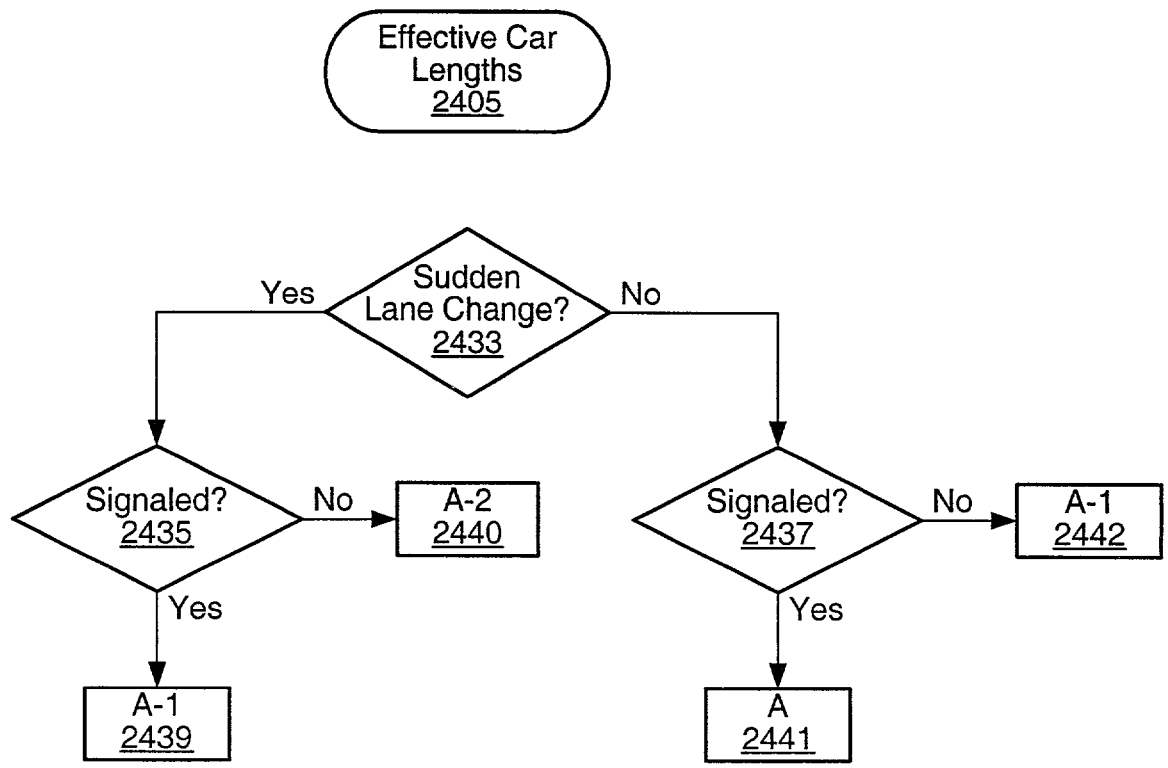
FIG. 24b is a flowchart corresponding to FIG. 24a according to one embodiment.

FIGS. 24*a* and 24*b* are flowcharts for estimating the effect of a factor that accounts for the contribution of an improper lane change to a motor vehicle accident according to one embodiment. An improper lane change may be a lane change that was completed before the accident and contributed to the accident. The improper lane change factor may be applied to the tortfeasor and/or other party only for accident type 1. In an embodiment, the factor may determine the effect on liability of an improper lane change based on car lengths between the vehicles before the accident and a subjective determination of the magnitude of deceleration of the parties. It is believed that an improper lane change may reduce the opportunity of the tortfeasor to avoid the accident and/or may reduce the tortfeasor's available stopping distance. For example, if other party and the tortfeasor are slowing and other party pulls in between the tortfeasor and whatever the other party and the tortfeasor are stopping for, the tortfeasor's available stopping distance may be reduced.

In FIG. 24a, decision point 2401 may ask whether the accident type was type 1, and whether the other party and right of way have been determined. If any of these conditions is not true, the factor may not be applicable, as shown in step 2403. If the accident type is 1, and the other party and right of way have been determined, then the next step 2404 may ask if the other party changed lanes prior to the accident. If the other party did not change lanes, then step 2406 indicates that the factor may not be applicable. If the other party changed lanes before the accident, the next step 2405 may be to determine effective car lengths between the other party and the tortfeasor. The term "effective car lengths," as used herein, generally refers to the actual car lengths between the parties minus an adjustment.

The determination of the effective car lengths 2405 is shown in FIG. 24b. Decision point 2433 may ask if the other party's lane change was a sudden lane change. If it was, then decision point 2435 may ask if the other party signaled the lane change. If the other party signaled, then the effective car lengths may be the actual car lengths minus one, as shown in step 2439. If the other party did not signal, then the effective car lengths may be the actual car lengths minus two, as shown by step 2440. If the answer to decision point 2433 is no, the decision point 2437 may ask if the other party signaled the lane change. If the other party did signal the lane change, then the effective car lengths may be the actual car lengths, as shown in step 2441. If the other party did not signal, then the effective car lengths may be the actual car lengths minus one, as shown by step 2442.

Turning again to FIG. 24a, if the effective car lengths are less than 1, then decision point 2409 may ask if the tortfeasor was slowing down when the lane change took place. If the tortfeasor was not slowing down, then a penalty value of 75% of liability may be assessed to the other party, as shown by step 2418. Alternately, in an embodiment, if the tortfeasor was not slowing down, then the liability may be determined by an experienced claims adjuster. If the tortfeasor was slowing down in either a slight or an extreme manner, then a penalty value of 100% of liability may be assessed to the other party at step 2417 or 2419. In some embodiments, an ALV of 100% liability may be assessed at steps 2417 and 2419 rather than a penalty value.

If the effective car lengths are about 1 or about 2, then decision point 2411 again may ask if the tortfeasor was slowing down. If the tortfeasor was not slowing down, then a penalty value of 75% of liability may be assessed to the other party, as shown by step 2422. Alternately, in an embodiment, if the tortfeasor was not slowing down, then the liability may be determined by an experienced claims adjuster. If the tortfeasor was slowing down in either a slight or an extreme manner, then a penalty value of 100% of liability may be assessed to the other party at step 2423 or 2425. In some embodiments, an ALV of 100% liability may be assessed at steps 2423 and 2425 rather than a penalty value.

If the effective car lengths are about 3 or about 4, then decision point 2413 may ask if the other party was slowing down. If the other party was either not slowing down or slightly slowing, then no penalty value may be assessed to either party, as shown by steps 2427 and 2429. If the other party was slowing down in an extreme manner at the time of the lane change, then a penalty value of 50% of liability may be assigned to the other party, as shown by steps 2431.

If the effective car lengths are greater than about 4, then no penalty value may be assessed to either party, as shown by steps 2407.

In other embodiments, the actual speed and/or distance between the vehicles before the accident or at the time of the lane change may be determined. An analysis like the one described above may then be used to determine the effect on liability of the lane change based on the actual speed and/or distance between the vehicles.

Figure 25:
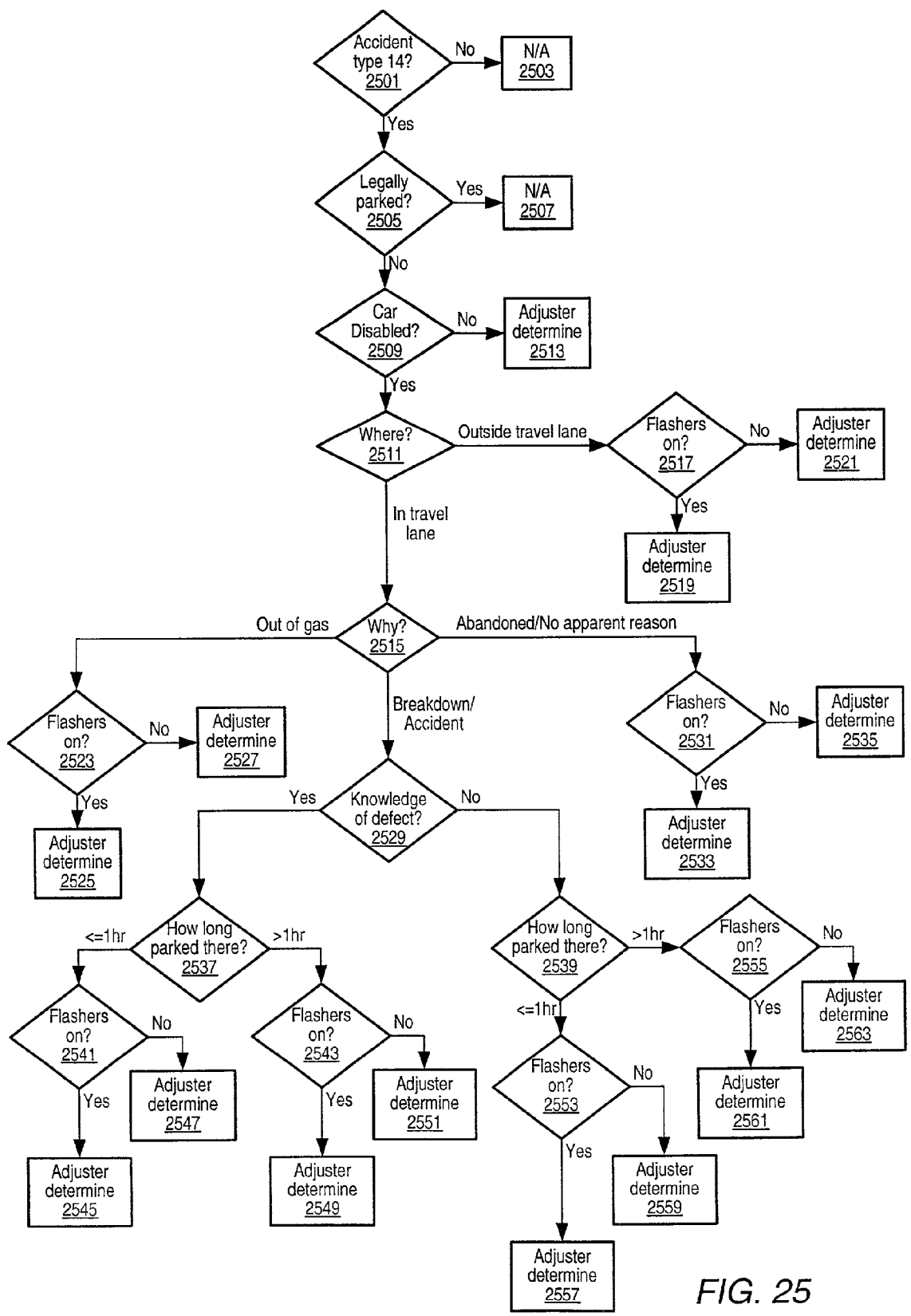
FIG. 25 is a logic diagram for estimating the contribution of improper parking to liability in a motor vehicle accident according to one embodiment.

FIG. 25 is a flowchart for estimating the effect of a factor that accounts for the contribution of an improperly parked vehicle to a motor vehicle accident according to one embodiment. The improperly parked vehicle factor may be applied only to the other party and only for accident type 14. In an embodiment, a parked vehicle may be considered legally parked, illegally parked, or disabled.

In FIG. 25, decision point 2501 and step 2503 indicate that the factor may not be applicable to accident types other than type 14. If the accident type is 14, then decision point 2505 may ask whether the vehicle was legally parked. If the vehicle was legally parked, then the factor may not be applicable, as shown by step 2507. If the vehicle was not legally parked, then decision point 2509 may ask if the vehicle was disabled. If the vehicle was not disabled and was not legally parked, then a penalty value may be estimated by an experienced claims adjuster, as shown by step 2513. If the vehicle was disabled and was not legally parked, then decision point 2511 may ask where the vehicle was parked. If the vehicle was outside a travel lane, then regardless of whether the vehicle had its flashers on, the factor may not be applicable, as shown by decision point 2517 and steps 2519 and 2521.

If the vehicle was parked in a travel lane, then decision point 2515 may ask why it was there. If the vehicle ran out of gas, then decision point 2523 asks if the vehicle had its flashers on. A penalty value may be determined by experienced claims adjusters in steps 2525 and 2527 for either a yes or no answer. If the vehicle was abandoned or there was no apparent reason why the vehicle was in the travel lane, then decision point 2531 may ask if the vehicle had its flashers on. A penalty value may be determined by an experienced claims adjuster in steps 2533 and 2535 for either a yes or no answer. If the vehicle was in the travel lane due to a breakdown or accident, then decision point 2529 may ask if the other party had knowledge of the defect, which may have caused the breakdown or accident. If yes, then decision point 2537 asks how long the vehicle had been parked at the location of the accident. If the vehicle was there for less than or equal to one hour, then decision point 2541 asks if the vehicle had its flashers on. A penalty value may be determined by experienced claims adjusters in steps 2545 or 2547 for either a yes or no answer. If the vehicle was sitting in the travel lane for more than one hour, then decision point 2541 asks if the vehicle had its flashers on. A penalty value may be determined by experienced claims adjusters in steps 2549 or 2551 for either a yes or no answer.

If the other party did not have knowledge of the defect at decision point 2529, then decision point 2539 may ask how long the vehicle had been parked at the location of the accident. If the vehicle was there for less than or equal to one hour, then decision point 2553 asks if the vehicle had its flashers on. A penalty value may be determined by experienced claims adjusters in steps 2557 or 2559 for either a yes or no answer. If the vehicle was sitting in the travel lane for more than one hour, then decision point 2555 may ask if the vehicle had its flashers on. A penalty value may be determined by experienced claims adjusters in steps 2561 or 2563 for either a yes or no answer, respectively.

In other embodiments, a parked vehicle may be assumed to always have the right of way. Thus, no improperly parked vehicle factor may be used.

Figure 26:
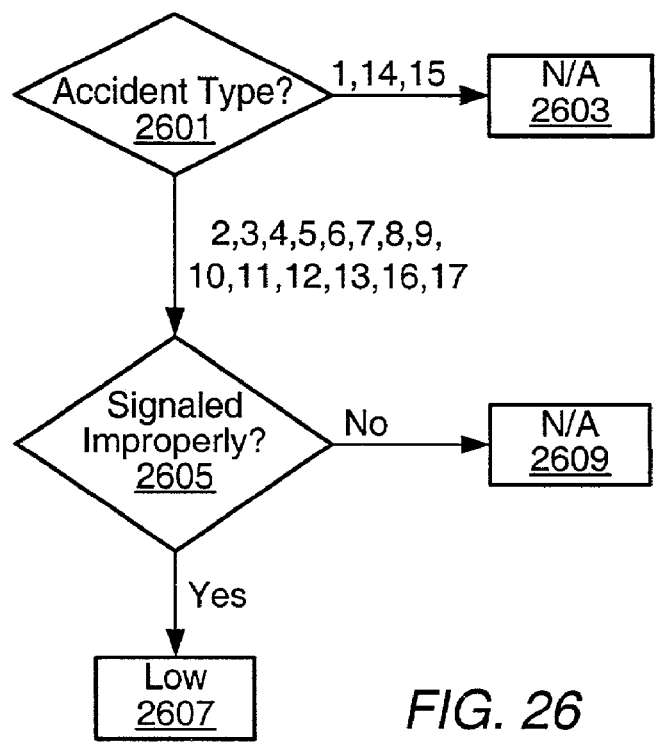
FIG. 26 is a flowchart for estimating the contribution of improper signaling to liability in a motor vehicle accident according to one embodiment.

FIG. 26 is a flowchart for estimating the effect of a factor that accounts for the contribution of improper signaling to a motor vehicle accident according to one embodiment. As used herein, the term "improper signaling" generally refers to signaling one action and doing another or not signaling at all. In certain embodiments, an improper signal may refer only to signaling one action and doing another (i.e., not to "no signal"). In such embodiments, an improper turn and lack of signal may not be part of the improper signaling factor. "No signal" and improper turn and lack of signal may already be taken into account by the roadway configuration/accident type combination.

As shown in FIG. 26, if it is determined at decision point 2601 that the accident type is 1, 14, or 15, then the factor may not be applicable, as shown in step 2603. For all other accident types, decision point 2605 may ask if a party signaled improperly. If the answer to decision point 2605 is no, then the factor may not be applicable, as shown by step 2609. If the answer is yes, then a "low" penalty value may be assessed against the party that signaled improperly, as shown in step 2607. In some embodiments, an additional decision point may follow decision point 2605 if a party did signal improperly. The additional decision point may determine which party signaled improperly. In such embodiments, if it is the other party that improperly signaled then a low penalty value may be assessed against the other party. If the tortfeasor improperly signaled, then a talking point may be reached.

Figure 27:
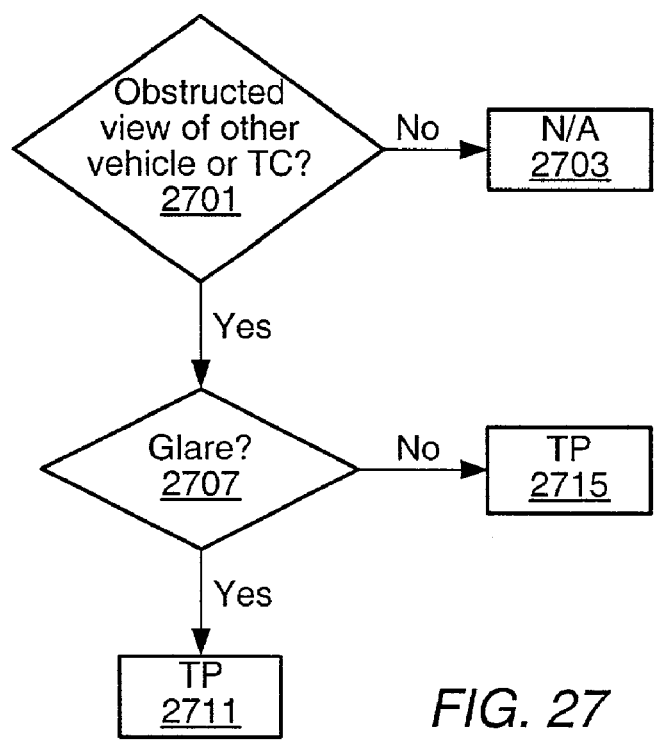
FIG. 27 is a flowchart for estimating the contribution of an obstructed view or glare to liability in a motor vehicle accident according to one embodiment.

FIG. 27 is a flowchart for estimating the effect of a factor that accounts for the contribution of an obstructed view or glare to a motor vehicle accident according to one embodiment. The obstructed view or glare factor may be applied to the tortfeasor and/or other party for any accident type. If an obstructed view or glare affected a party's view of other vehicles or a traffic sign, the factor may be a talking point.

In FIG. 27, decision point 2701 may ask if a driver's view of another vehicle or a traffic control was obscured. Step 2703 indicates that if the answer is no, then the factor may not be applicable. In some embodiments, if the answer to decision point 2701 is yes, then another decision point may ask if the obstructed view or glare contributed to the accident. If not, then the factor may not be applicable. If it is determined that the obstructed view or glare contributed to the accident, the decision point may lead to decision point 2707. Decision point 2707 may ask whether it was a glare obscured the driver's view. If it was a glare, then the factor may be a talking point, as shown by step 2711. In some embodiment, if the answer to decision point 2707 is no, then there may be a request to provide a description of the obstruction for use in an assessment report. In step 2715, the obstructed view may be a talking point.

Figure 28:
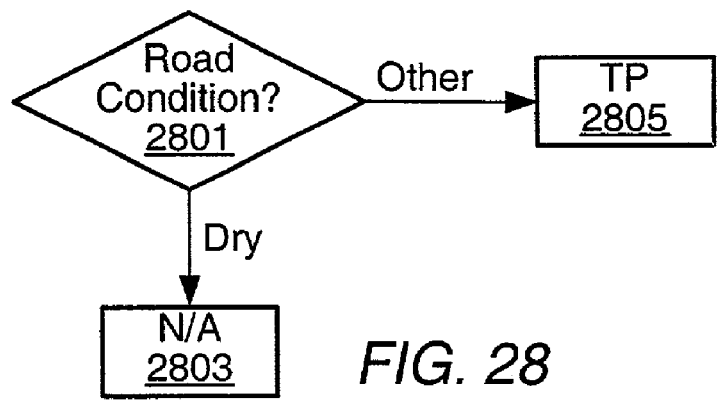
FIG. 28 are flowchart for estimating the contribution of the road condition to liability in a motor vehicle accident according to one embodiment.

FIG. 28 is a flowchart for estimating the effect of a factor that accounts for the contribution of road condition to a motor vehicle accident according to one embodiment. The road condition factor may be applied to the tortfeasor and/or other party for any accident type. As shown in FIG. 28, the road condition at decision point 2801 may be either dry or in some other condition. If the road condition is dry, then step 2803 may indicate that the factor may not be applicable. Other conditions may include, but are not limited to, a roadway that is wet, has snow and/or ice, is muddy, has plowed snow, has been salted, or has snow and/or ice patches. If other conditions apply to the roadway, then step 2805 may indicate that the factor may be a talking point.

Figure 29:
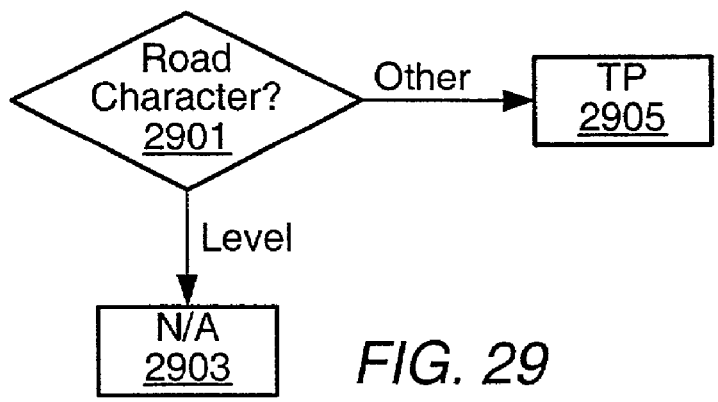
FIG. 29 are flowcharts for estimating the contribution of the road character to liability in a motor vehicle accident according to one embodiment.

FIG. 29 is a flowchart for estimating the effect of a factor that accounts for the contribution of road character to a motor vehicle accident according to one embodiment. The road character factor may be applied to the tortfeasor and/or other party for any accident type. As shown in FIG. 29, the road character at decision point 2901 may be either level or some other character. If the road character is level, then step 2903 indicates that the factor may not be applicable. Other road characters may include, but are not limited to, a roadway that has a hill, a hillcrest, or a sag-bottom of a hill. If other road characters apply to the roadway, then step 2905 may indicate that the factor may be a talking point.

Figure 30:
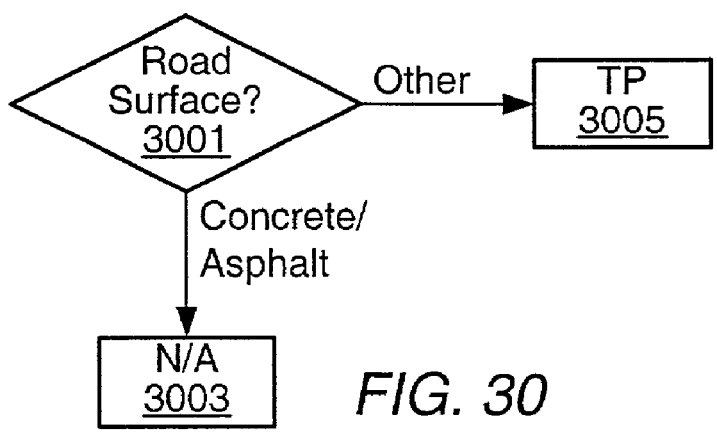
FIG. 30 are flowcharts for estimating the contribution of the road surface to liability in a motor vehicle accident according to one embodiment.

FIG. 30 is a flowchart for estimating the effect of a factor that accounts for the contribution of road surface to a motor vehicle accident according to one embodiment. The road surface factor may be applied to the tortfeasor and/or other party for any accident type. As shown in FIG. 30, the road surface at decision point 3001 may be either concrete/asphalt or some other surface. If the road surface is concrete/asphalt, then step 3003 may indicate that the factor may not applicable. Other road surfaces may include, but are not limited to brick, dirt, or gravel. If other surfaces apply to the roadway, then step 3005 indicates that the factor may be a talking point.

Figure 31A:
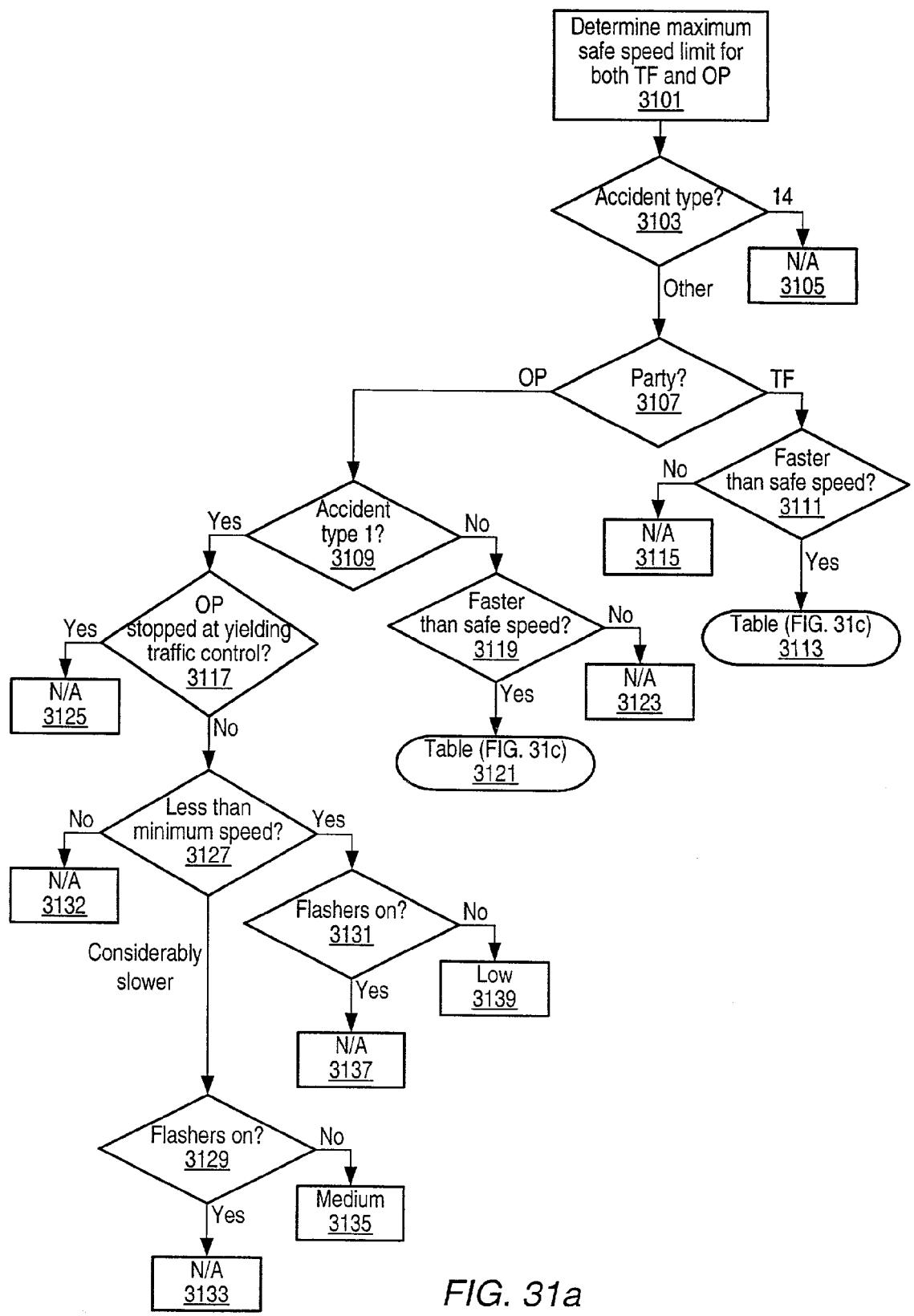
FIG. 31a is a flowchart for estimating the contribution of speed to liability in a motor vehicle accident according to a first embodiment.

FIGS. 31*a-b* may be used in combination with FIG. 31*c* for estimating the effect of a factor that accounts for the contribution of speed to a motor vehicle accident according to a first embodiment. In some embodiments, the speed factor may not apply to accident type 14. The speed factor may be applied to either or both parties depending on the circumstances of the accident.

In FIG. 31*a*, step 3101 in estimating the speed factor may be to determine the maximum safe speed. In some embodiments, step 3101 may be directed to determining the maximum legal speed. Determination of the maximum safe speed is illustrated by the flowcharts in FIG. 31*b*. As shown in FIG. 31*b*, the maximum safe speed may be determined by reducing the legal speed limit to account for adverse road conditions and/or weather conditions. If the road condition is dry and the weather clear, the maximum safe speed may be the legal speed limit. However, if the road condition is not dry and/or the weather is not clear, then the maximum safe speed may be less than the speed limit. Decision point 3141 in FIG. 31*b* may inquire as to the road condition at the accident scene. Steps 3143, 3145, 3147, 3149, and 3151 may provide the corrections when road conditions are dry (e.g., 0), wet (e.g., 0.1× legal speed limit), snow (e.g., 0.2×legal speed limit), muddy (e.g., 0.2×legal speed limit), and ice (e.g., 0.3×legal speed limit), respectively. Similarly, decision point 3153 in FIG. 31*b* may inquire as to the weather at the accident scene. Steps 3155, 3157, 3159, and 3161 may provide the corrections when the weather is clear (e.g., 0), smoke, etc. (e.g., 0.1×legal speed limit), snowing (e.g., 0.2×legal speed limit), and fog (e.g., 0.2×legal speed limit), respectively. For example, if the speed limit is 60 miles per hour, the road condition is wet, and the weather is snowing the safe speed may be: 60−(0.1×60)−(0.2×60)=60−6−12=42 miles per hour.

Step 3105 in FIG. 31*a* shows that if the answer to decision point 3103 is accident type 14, the factor may not be applicable. For any other accident type, decision point 3107 may ask which party is under consideration. If the party is the tortfeasor, then decision point 3111 may ask if the party was going faster than the maximum safe speed calculated in step 3101. If the answer is yes, then step 3113 may refer to the table in FIG. 31*c* to calculate the effect on the liability. If the party was not going faster than the maximum safe speed, then the factor may not be applicable, as shown in step 3115.

If the party being considered at decision point 3107 is the other party, then decision point 3109 may ask if the accident type is 1. If the accident type is not 1, then decision point 3119 may ask if the other party was going faster than the maximum safe speed calculated in step 3101. If the answer is yes, then step 3121 may refer to the table in FIG. 31*c* to calculate the effect on the liability. If the party was not going faster than the maximum safe speed, then step 3123 may indicate that the factor may not be applicable.

If the accident type is 1 at decision point 3109, decision point 3117 may ask if the other party was stopped at a yielding traffic control. If the answer is yes, then step 3125 indicates that the factor may not be applicable. If the answer is no, then decision point 3127 may ask if the other party was traveling at less than a minimum legal speed for the roadway. If not, then step 3132 indicates that the factor may not be applicable. If the party was traveling at less than the minimum legal speed, but not considerably slower, then decision point 3131 may ask if the vehicle's flashers were on. Step 3137 indicates that the factor may not be applicable if the vehicle's flashers were on. If the flashers were not on, step 3139 indicates that a "low" penalty value may be assessed against the other party. If the other party was traveling considerably slower than the minimum legal speed, then decision point 3129 may ask if the vehicle's flashers were on. Step 3133 indicates that the factor may not be applicable if the flashers were on. If the flashers were not on, step 3135 indicates that a "medium" penalty value may be assessed against the other party. In certain embodiments, other considerations may be used in determining the effect on liability of the other party traveling at less than the minimum legal speed. For example, in certain jurisdictions, various methods may be allowed to indicate a slow moving vehicle. For example, a sign or placard may be displayed on a vehicle or the vehicle may have a flashing yellow light. In such embodiments, the use of any approved method to provide warning to other traffic that the vehicle is moving slowly may result in the factor being not applicable.

FIG. 31*c* is a table illustrating the estimation of the effect of a factor that accounts for the contribution of speed to a motor vehicle accident according to the first embodiment. The first column of FIG. 31*c* may be related to the maximum safe speed calculated as shown in FIG. 31*b*. The second column of FIG. 31*c* may include an actual speed for the vehicle. The third column may include following distances subjectively estimated by an experienced claims adjuster for several ranges of the actual speed of a following vehicle. A following distance less than that specified for a given actual speed range may be considered close while a following distance greater than that specified may be considered far. The fourth and fifth columns may provide exemplary penalty values or ALVs to be assessed to a party under consideration.

For example, if the determined maximum safe speed is 50 miles per hour, a vehicle with an actual speed of 65 miles per hour following at a distance of 175 feet may have a penalty value assessed of 10% according to FIG. 3*c*. For the same maximum safe speed, a vehicle with an actual speed of 85 miles per hour may have an absolute liability value of 70% assessed.

Figure 32B:
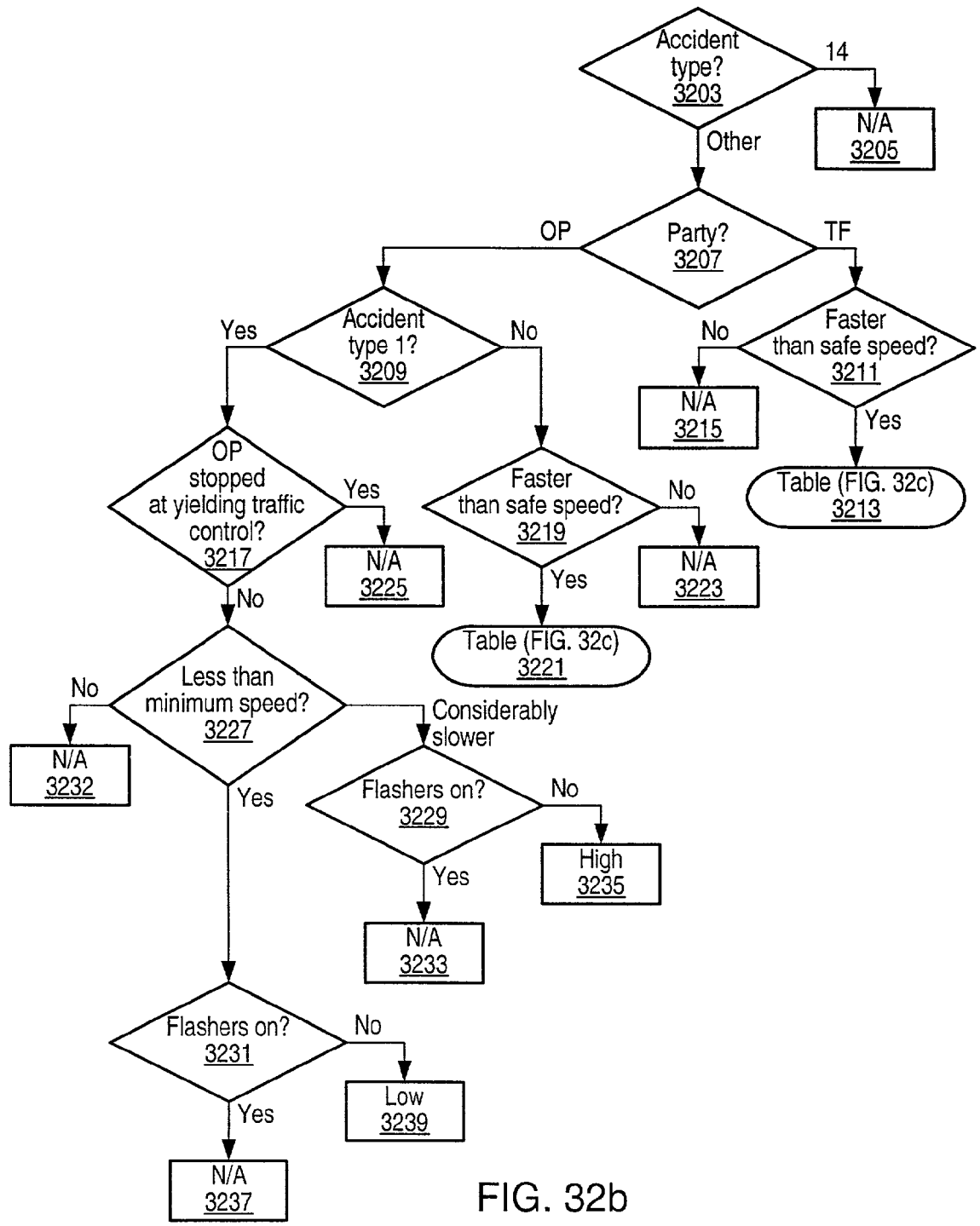
FIG. 32b is a flowchart for estimating the maximum safe speed for given road and weather conditions according to the second embodiment.

FIGS. 32*a-c* may be used for estimating the effect of a factor that accounts for the contribution of speed to a motor vehicle accident according to a second embodiment. In some embodiments, the speed factor may not apply to accident type 14, as shown in step 3205 of FIG. 32*b*.

Referring to FIG. 32*a*, a maximum safe speed may be estimated. The maximum safe speed may be estimated as a percentage of the maximum legal speed (i.e., speed limit) for the location. To estimate the percentage of the speed limit corresponding to the maximum safe speed, a road condition may be selected from the first column of the table. Each road condition may be associated with a percentage that may be used to estimate the maximum safe speed for the location. Thus, for example, a vehicle traveling on a dry road having a speed limit of 65 mph may be estimated as having a maximum safe speed of 65 mph. However, if the road is wet, the vehicle may be estimated to have a maximum safe speed of about 59 mph.

In some embodiments, after the safe speed from the table is determined an additional adjustment may be made to the estimate of the maximum safe speed based on the weather. For example, in some embodiments, if the weather is raining, sleeting or hailing the safe speed from the table in FIG. 32*a* may be reduced by 10%. If the weather is snowing, the safe speed determined from the table in FIG. 32*a* may be reduced by 20%. If the weather is foggy, smoky or smoggy the safe speed determined from the table in FIG. 32*a* may be reduced by 30%.

FIG. 32*b* depicts a flowchart for determining the effect of speed on liability in a vehicle accident. Step 3205 shows that if the answer to decision point 3203 is accident type 14, the factor may not be applicable. For any other accident type, decision point 3207 may ask which party is under consideration. If the party is the tortfeasor, then decision point 3211 may ask if the tortfeasor was going faster than the estimated maximum safe speed. If the answer is yes, then step 3213 may refer to the table in FIG. 32*c* to calculate the effect on the liability. If the tortfeasor was not going faster than the maximum safe speed, then the factor may not be applicable, as shown in step 3215.

If the party being considered at decision point 3207 is the other party, then decision point 3209 may ask if the accident type is 1. If the accident type is not 1, then decision point 3219 may ask if the other party was going faster than the estimated maximum safe speed. If the answer is yes, then step 3221 may refer to the table in FIG. 32*c* to calculate the effect on the liability. If the party was not going faster than the maximum safe speed, then step 3223 indicates that the factor may not be applicable.

However, if the accident type is 1 at decision point 3209, decision point 3217 may ask if the other party was stopped at a yielding traffic control. If the answer is yes, then step 3225 indicates that the factor may not be applicable. If the answer is no, then decision point 3227 may ask if the other party was traveling at less than a minimum legal speed for the roadway. In some embodiments, decision point 3227 may ask if the other party was traveling at less than a prevailing speed on the roadway. If the other party was not traveling at less than the minimum legal speed, then step 3232 indicates that the factor may not be applicable. If the other party was traveling at less than the minimum legal speed, but not considerably slower, then decision point 3231 may ask if the vehicle's flashers were on. Step 3237 indicates that the factor may not be applicable if the vehicle's flashers were on. If the flashers were not on, step 3239 indicates that a "low" penalty value may be assessed against the other party. If the other party was traveling considerably slower than the minimum legal speed, then decision point 3229 may ask if the vehicle's flashers were on. Step 3233 indicates that the factor may not be applicable if the vehicle's flashers were on. If the flashers were not on, step 3235 indicates that a "high" penalty value may be assessed against the other party. In certain embodiments, other considerations may be used in determining the effect on liability of the other party traveling at less than the minimum legal speed as discussed with reference to FIGS. 31*a* and 31*b*.

FIG. 32*c* may be used to estimate an effect on liability of the contribution of speed to a vehicle accident. The table of FIG. 32*c* may be used in the same manner described for FIG. 31*c* above.

Figure 33A:
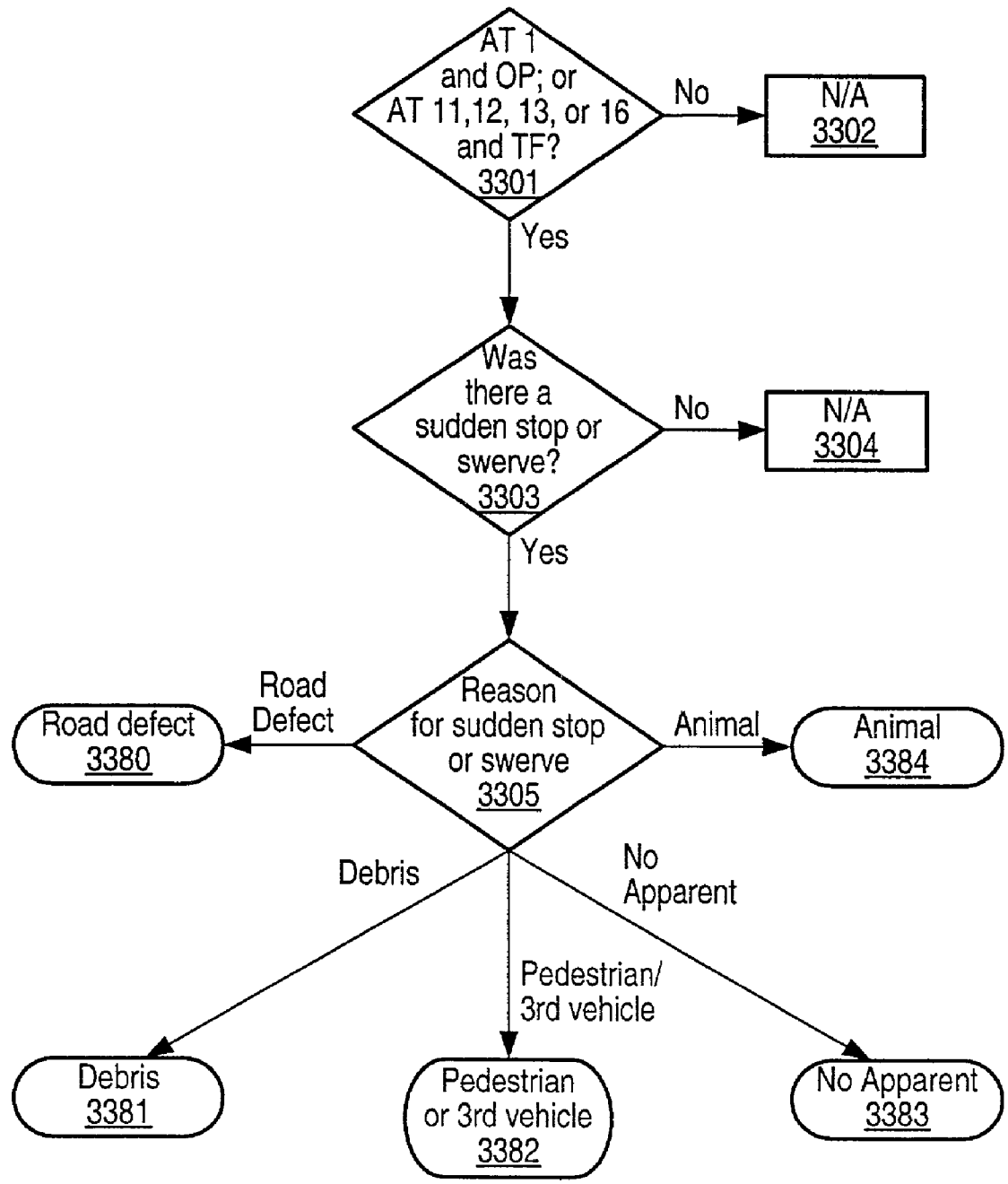
FIGS. 33a, 33b, 33c, 33d, 33e, and 33f are flowcharts for estimating the contribution of a sudden stop or swerving to liability in a motor vehicle accident according to one embodiment.

FIG. 33*a* is a flowchart for estimating the effect of a factor that accounts for the contribution of a sudden stop or swerve to a motor vehicle accident according to one embodiment. As used herein, the term "sudden stop or swerve" generally refers to a rapid deceleration or change of direction. A sudden stop or swerve may typically be taken to avoid another object such as, but not limited to, an animal, pedestrian, road defect, another vehicle or road debris. FIGS. 33*b*-*f* are flowcharts associated with FIG. 33*a* that estimate the effect on liability of a sudden stop or swerve. A sudden stop or swerve factor may be applied to the tortfeasor for accident types 11, 12, 13, and 16 or to the other party for accident type 1.

In FIG. 33*a*, decision point 3301 and step 3302 indicate that the factor may not be applicable to combinations other than to the tortfeasor for accident types 11, 12, 13, or 16 and to the other party for accident type 1. If the party and accident type under consideration are one of these combinations, then decision point 3303 asks whether there was a sudden stop or swerve in the accident. If there was not, then the factor may not be applicable, as shown by step 3304. If there was a sudden stop or swerve then the reason for the sudden stop or swerve may be solicited at decision point 3305. The reason may include a road defect, debris, a pedestrian, another vehicle, or an animal. In addition, FIG. 33*a* also considers the case of a sudden stop or swerve for no apparent reason.

Figure 33B:
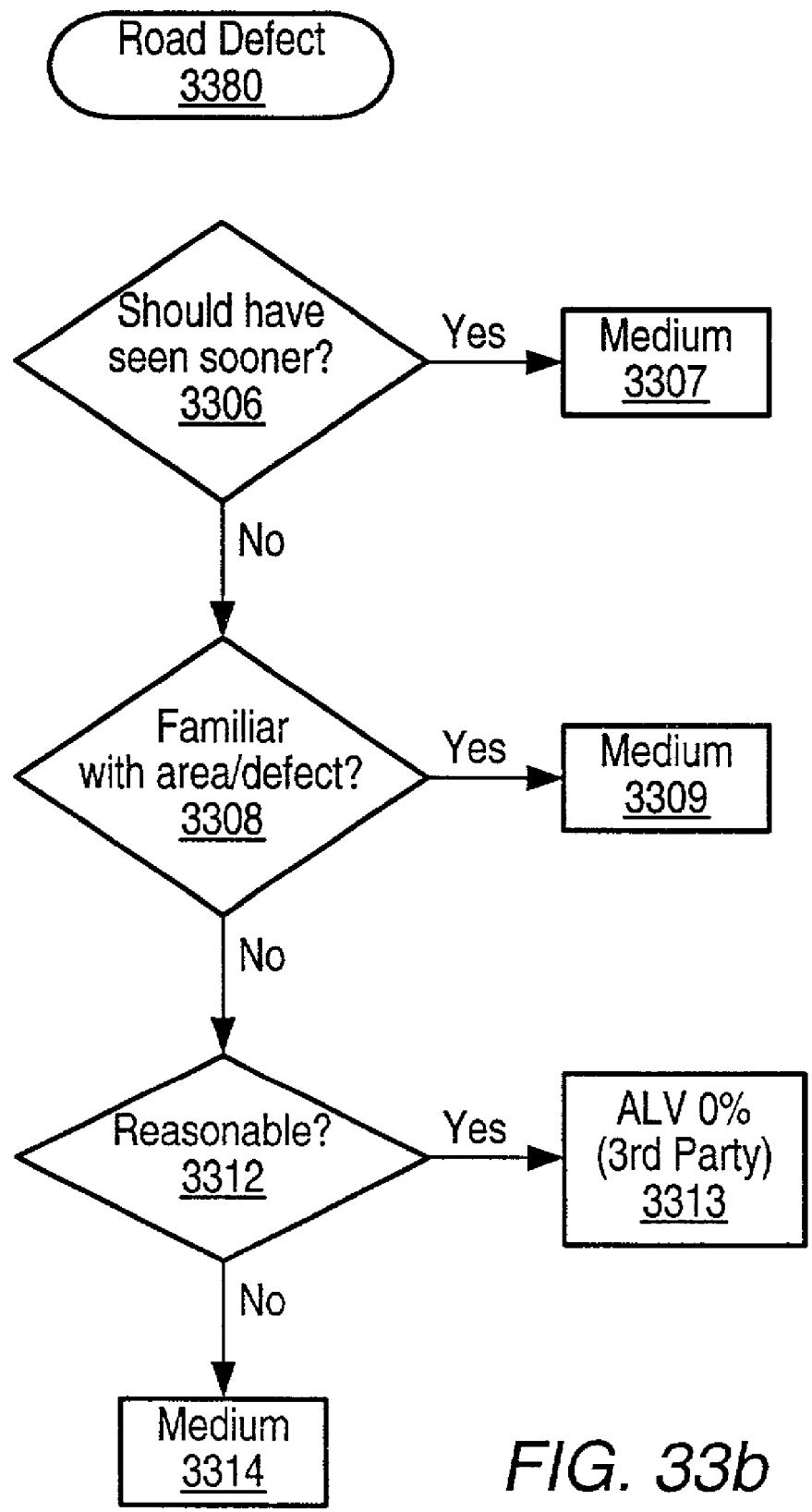

In FIG. 33*a*, if the reason is a road defect the flowchart may refer to a road defect flowchart 3380 as depicted in FIG. 33*b*. The first decision point 3306 in road defect flowchart 3380 may asks if the party should have seen the road defect sooner than the party did. If yes, then a "medium" penalty value may be assessed to the party under consideration as shown by decision point 3307. If the answer to decision point 3306 is no, then decision point 3308 may be reached where it is determined whether the party was familiar with the area of the accident and/or the defect. If the party was familiar with the area of the accident and/or the defect, then a "medium" penalty value may be assessed to the party, as shown by step 3309. If the party was not familiar with the area of the accident and/or the defect at decision point 3308, then decision point 3312 may ask if the sudden stop or swerve was reasonable. If the answer is yes, then an ALV of 0% liability may be assessed to the party at step 3313. In addition, it may be noted in an assessment report that a third party (e.g., a party responsible to maintain the road or a party that cased the defect) may have contributed to the accident, and may thus bear a portion of the liability. If at decision point 3312, it is determined that the action was not reasonable, then a "medium" penalty value may be assessed to the party at step 3314.

Figure 33C:
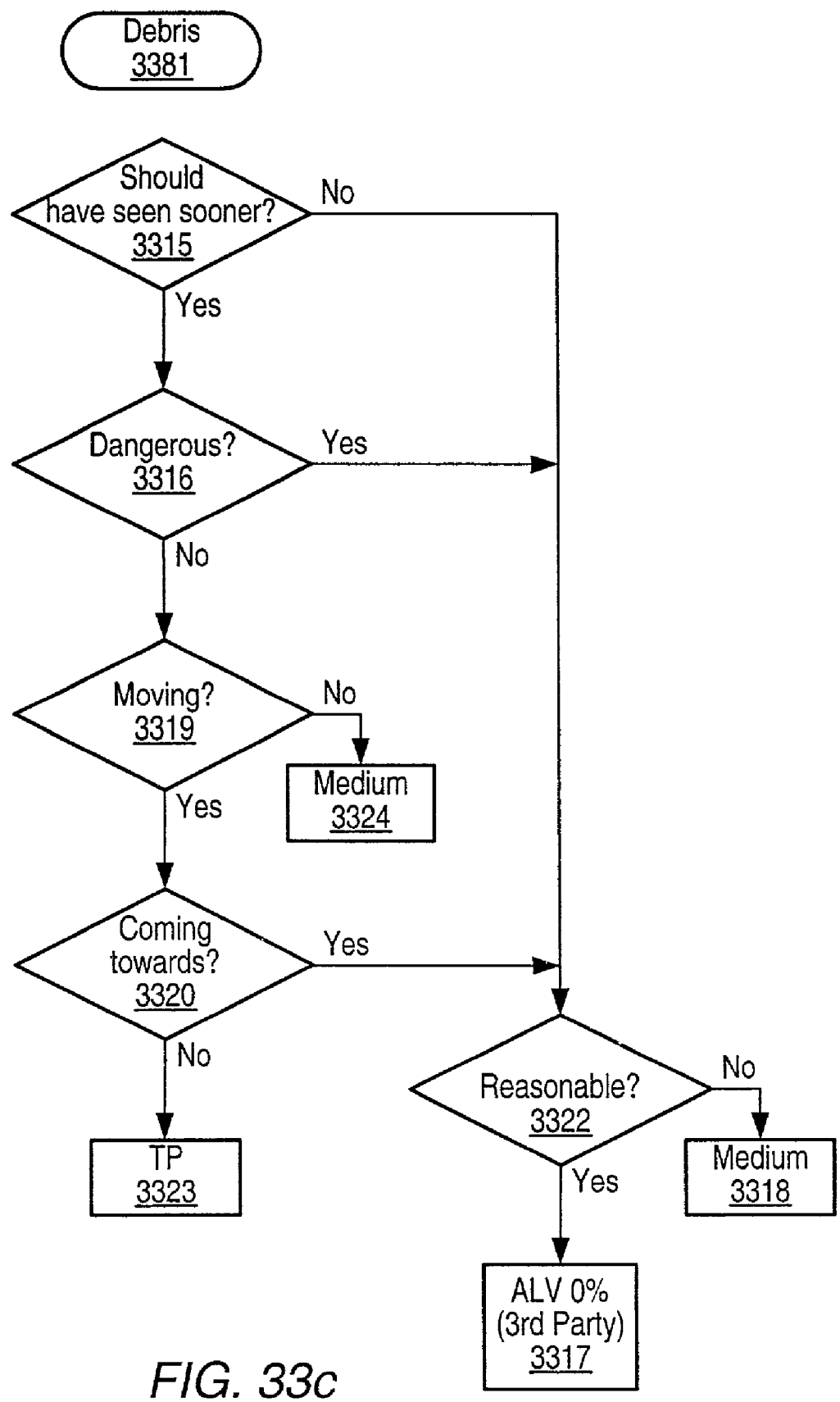

In FIG. 33*a*, if the reason for the sudden stop or swerve at decision point 3305 is debris, then the flowchart may refer to a debris flowchart 3381 as depicted in FIG. 33*c*. Decision point 3315 of debris flowchart 3381 may ask whether the party should have seen the debris sooner than the party did. If not, then decision point 3322 may be reached, which may ask if the sudden stop or swerve was reasonable. If the answer to decision point 3315 is yes, then decision point 3316 may determine whether the debris was dangerous. If the debris was dangerous, then decision point 3322 may ask if the sudden stop or swerve was reasonable. If the debris was not dangerous, then decision point 3319 may ask if the debris was moving. If the debris was not moving, then a "medium" penalty value may be assessed against the party. If the debris was moving, then decision point 3320 may inquire whether the debris was coming towards the party. If not, then a talking point may be reached in step 3323. If yes, then decision point 3322 may ask if the sudden stop or swerve was reasonable. At decision point 3322, if it is determined that the action was reasonable, then an ALV of 0% may be assessed against the party at step 3317. In addition, it may be noted in an assessment report that a third party (e.g., a party responsible for the debris) may have contributed to the accident, and may thus bear a portion of the liability. If at decision point 3322, it is determined that the action was not reasonable then a "medium" penalty value may be assessed to the party at step 3318.

Figure 33D:
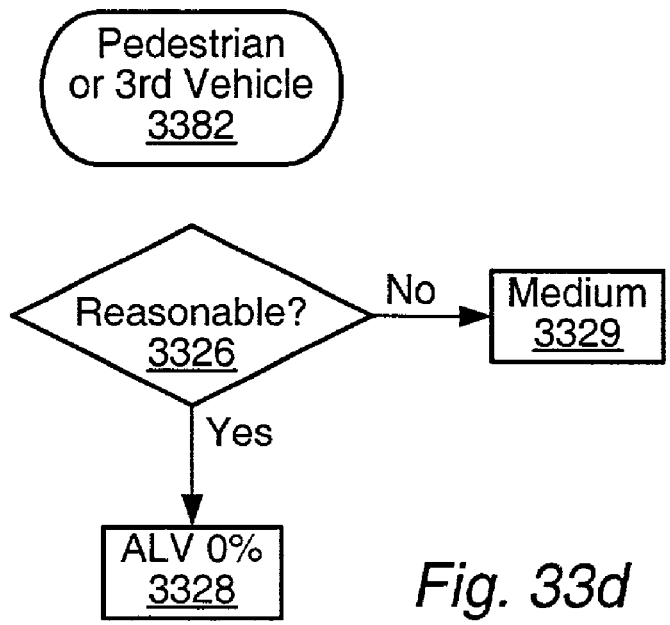

In FIG. 33*a*, if the reason for the sudden stop or swerve at decision point 3305 is a pedestrian or other vehicle, then the flowchart may refer to a pedestrian or 3rd vehicle flowchart 3382 as depicted in FIG. 33*d*. It may be determined at decision point 3326 whether the sudden stop and swerve was reasonable. If it was reasonable, then an ALV of 0% may be assessed to the party under consideration, as shown by step 3328. If the sudden stop and swerve at decision point 3326 is not reasonable, then a "medium" penalty value may be assessed to the party as shown by step 3329.

Figure 33E:
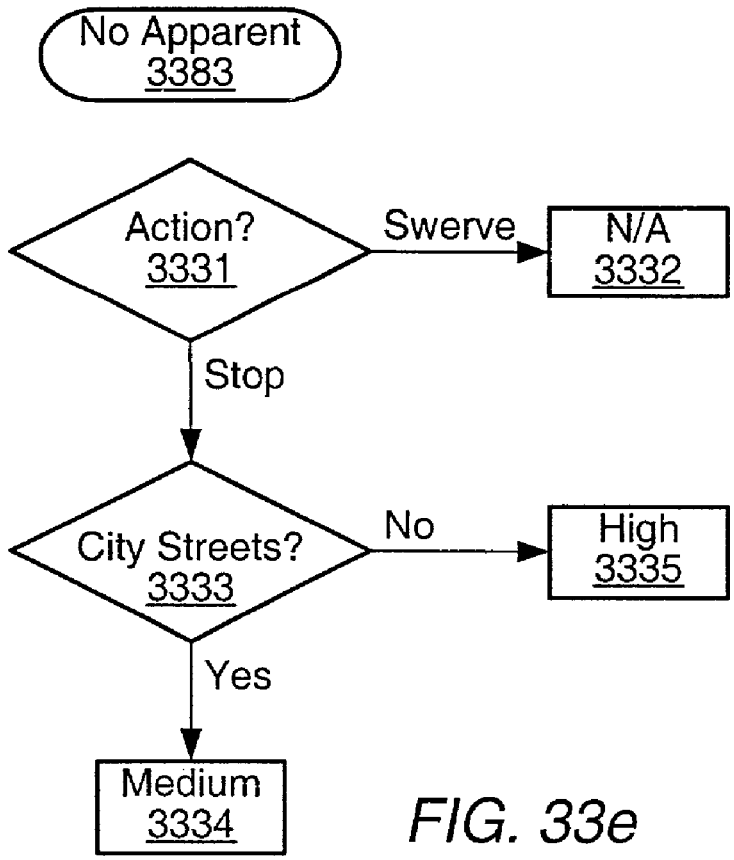

In FIG. 33*a*, if there is no apparent reason for the sudden stop or swerve at decision point 3305, then the flowchart may refer to a no apparent reason flowchart 3383 as depicted in FIG. 33*e*. If the action was a swerve, then the factor may not be applicable, as shown by step 3332. Alternately, in some embodiments, a "medium" penalty value may be assessed if the action was a swerve. If the action was a sudden stop, decision point 3333 may ask if the accident occurred on city streets. If yes, a "medium" penalty value may be assessed to the party as shown by step 3334. If not, a "high" penalty value may be assessed to the party as shown by step 3335.

Figure 33F:
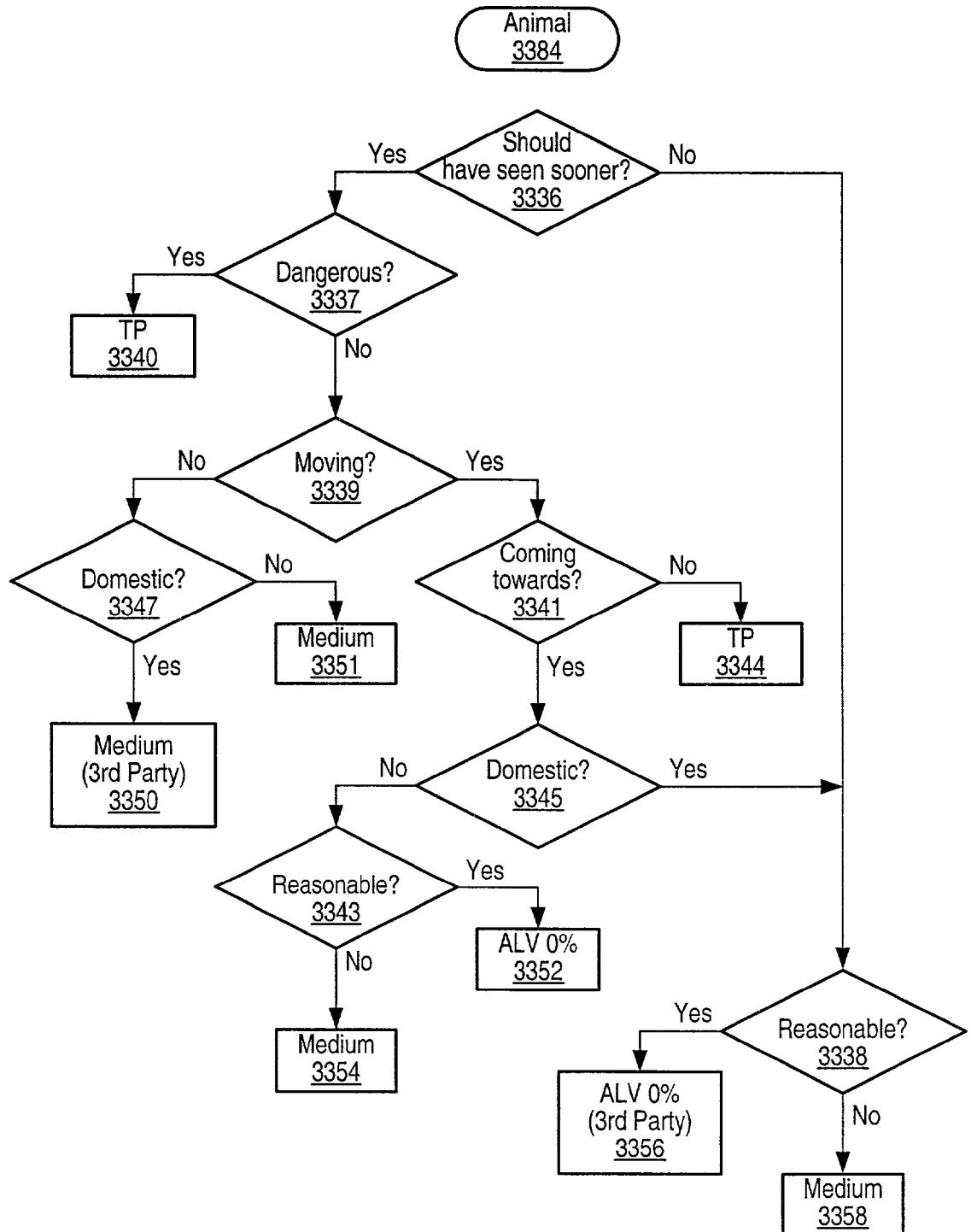

In FIG. 33*a*, if the reason for the sudden stop or swerve at decision point 3305 is an animal, then the flowchart may refer to an animal flowchart 3384 as depicted in FIG. 33*f*. It may be determined at decision point 3336 if the party should have seen the animal sooner. If not, then decision point 3338 may be reached which may ask if the sudden stop or swerve was reasonable. If the answer to decision point 3336 is yes, then decision point 3337 may ask if the situation was dangerous. If it is determined that the situation may have been dangerous, then a talking point may be reached at step 3340. If the situation was not dangerous, then decision point 3339 may ask if the animal was moving. If the animal was not moving, then decision point 3347 may ask if the animal was domestic as shown by decision point 3347. If the animal was domestic, then a "medium" penalty value may be assessed against the party. Additionally, it may be noted in an assessment report that a third party (e.g., the animal's owner) may bear a portion of the liability. If the animal was not domestic, then a "medium" penalty value may be assessed against the party.

If the animal was moving, in answer to decision point 3339, decision point 3341 may ask if the animal was coming towards the party. If the animal was not, then a talking point may be reached, as shown by step 3344. If the animal was coming towards the party, then decision point 3345 may determine if the animal was domestic. If the animal was not domestic, decision point 3343 may determine if the action was reasonable. If it is determined that the action was reasonable then an ALV of 0% may be assessed against the party at step 3352. If at decision point 3343, it is determined that the action was not reasonable then a "medium" penalty value may be assessed to the party at step 3354. If at decision point 3345 it is determined that the animal was domestic, decision point 3338 may determine if the sudden stop or swerve was reasonable. If it is determined that the action was reasonable, an ALV of 0% may be assessed against the party at step 3356. In addition, it may be noted in an assessment report that a third party (e.g., the animal's owner) may have contributed to the accident, and may thus bear a portion of the liability. If at decision point 3338, it is determined that the action was not reasonable then a "medium" penalty value may be assessed to the party at step 3358.

Figure 34:
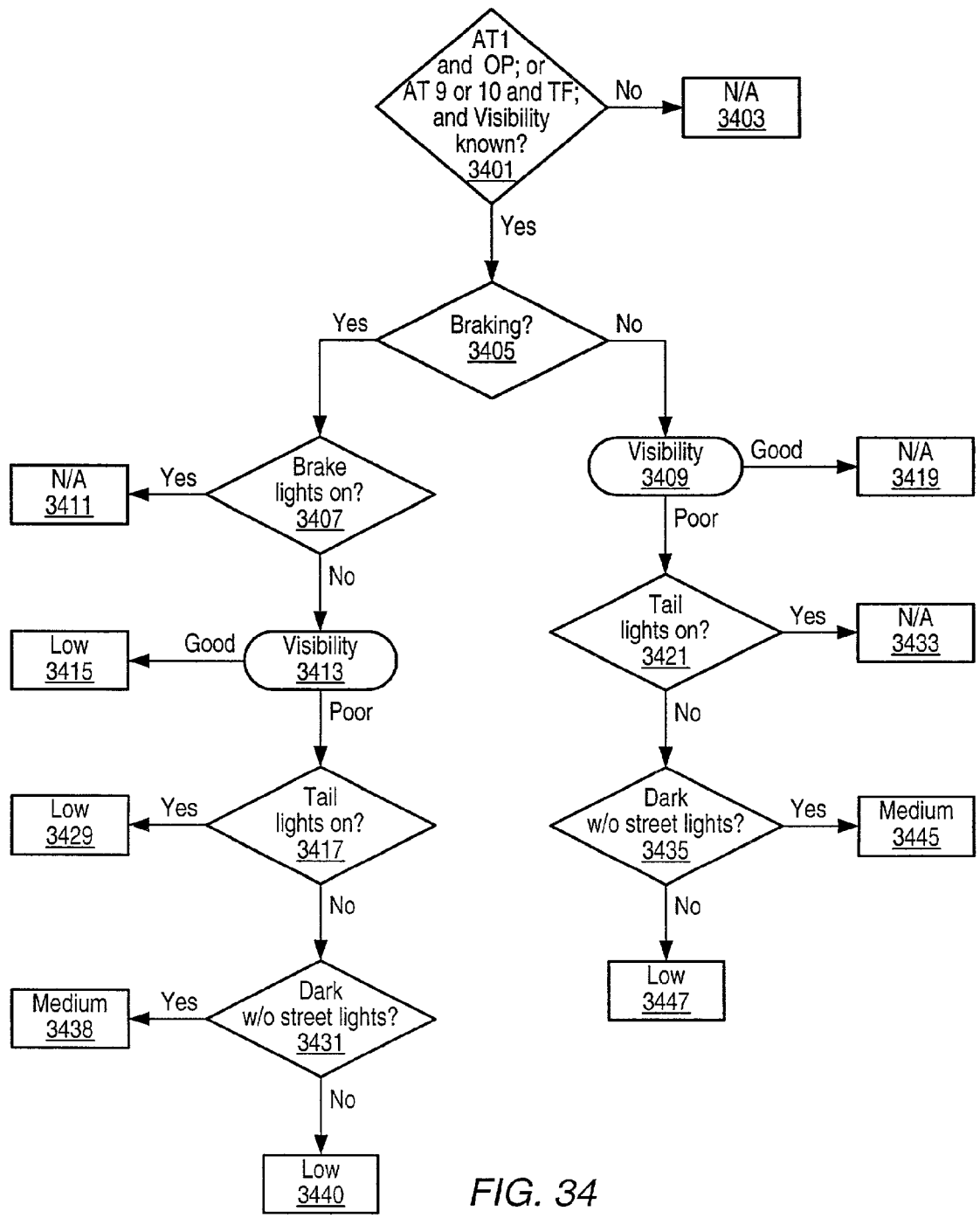
FIG. 34 is a flowchart for estimating the contribution of taillights or brake lights being off when they should have been on to liability in a motor vehicle accident according to one embodiment.

FIG. 34 is a flowchart for estimating the effect of a factor that accounts for the contribution of all taillights or brake lights being off when they should have been on to a motor vehicle accident according to one embodiment. The factor may apply to accidents where all taillights or brake lights on a vehicle were off when they should have been on and contributed to the accident.

In FIG. 34, decision point 3401 and step 3403 indicate that the factor may not be applicable for combinations other than to the tortfeasor for accident types 9 or 10 and to the other party for accident type 1. In each case, the visibility should be known. The next step for one of those combinations is decision point 3405, which may ask if the party was braking when the accident occurred. If the party was not braking, then decision point 3409 may ask the visibility at the accident scene. Determination of the visibility is discussed with regard to FIG. 35. Step 3419 indicates that the factor may not be applicable if the visibility is good. If the visibility is poor, then decision point 3421 may ask if the tail lights were on. In an embodiment, tail lights may be considered to be on if at least one tail light is on. Step 3433 indicates that the factor may not be applicable if the tail lights were on.

However, if tail lights were not on, decision point 3435 may ask whether it was dark without street lights. If the answer is yes to decision point 3435, a "medium" penalty value may be assessed against the party with the tail lights off at step 3445. Step 3447 indicates that if the answer to decision point 3435 is no, then a "low" penalty value may be assessed against the party with the tail lights off.

If the answer to decision point 3405 is yes, then decision point 3407 may ask whether brake lights were on. In an embodiment, brake lights may be considered on if at least one brake light was on. In other embodiments, brake lights may be considered to be on if two or more brake lights were on. Step 3411 indicates that the factor may not be applicable if brake lights were on. If brake lights were not on, decision point 3413 inquires into the visibility at the accident scene. If visibility was good, then a "low" penalty value may be assessed to the party with brake lights off, as shown by step 3415. If the visibility was poor, then decision point 3417 may ask if the tail lights were on. If the tail lights were on, then, according to step 3429, a "low" penalty value may be assessed to the party with the brake lights off. However, if the tail lights were not on then decision point 3431 may be reached. The steps 3438 and 3440 are identical to steps 3445 and 3447 previously described.

FIG. 35 is a flowchart for estimating the effect of a factor that accounts for the contribution of visibility to a motor vehicle accident according to one embodiment. The visibility factor may be applied to the tortfeasor and/or other party for any accident type. As used herein, the term "visibility" is generally defined as a combination of the weather and the lighting that adversely affects ability to see other vehicles, traffic controls, etc. In some embodiments, visibility may not be an adjusting or talking point factor in and of itself. It may be mentioned as a comment to the accident. Visibility may be an input to other factors. In some embodiments, weather may be a separate flowchart that may be used as an input to other factors. Lighting may include, but is not limited to, day, dawn, dusk, night with street lights, and night without lights. Weather may include, but is not limited to, clear, cloudy, raining, sleet/hail/freezing rain, snow, fog/smoke/smog/dust, and fog with rain.

FIG. 35 is a flowchart that estimates the effect of visibility on the liability. The first step in FIG. 35 is decision point 3501 that may ask the lighting conditions at the accident scene. If the lighting was daytime, then decision point 3503 may determine the weather conditions. If the weather is clear/cloudy as shown by step 3517, then the factor may not be applicable. Alternatively, if the weather is "all others" (i.e., other than clear or cloudy) as shown by step 3519, the visibility may be a talking point. As input into another flowchart, steps 3519 and 3513 may be considered poor visibility and steps 3517 and 3511 may be considered good visibility.

Similarly, the adverse weather may be determined at decision point 3505 if the answer to decision point 3501 is "other." If the answer to decision point 3505 is "clear/cloudy," then visibility may be a talking point in reference to lighting as shown by step 3511. If the answer to decision point 3505 is "all other," then visibility may be a talking point in reference to weather and lighting as shown by step 3513.

Figure 36:
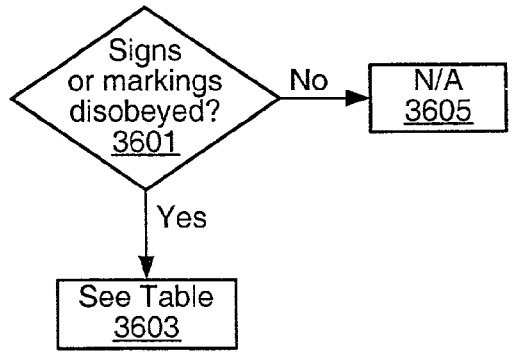
FIG. 36 is a flowchart and table for estimating the contribution of disobeyed signs or markings to liability in a motor vehicle accident according to one embodiment.

FIG. 36 depicts an embodiment of a flowchart and table for noting in an assessment report the effect of disobeyed signs or markings. In FIG. 36, decision point 3601 may determine if one or more signs or markings were disobeyed. If at decision point 3601, it is determined that no signs or markings were disobeyed, the factor may not be applicable as shown at step 3605. If signs or markings were disobeyed, the method may refer to table 3607 at step 3603.

Table 3607 may provide a list of potential signs and markings that may have been disobeyed in column 3609. If a sign or marking was disobeyed, a note may be added to an assessment report indicating the sign or marking disobeyed and whether a citation resulted. If no citation was issued, then a note from violation column 3613 corresponding to the sign or marking disobeyed may be added to the assessment report. If a citation was issued then a note from citation column 3615 corresponding to the sign or marking disobeyed may be added to the assessment report as discussed with reference to FIG. 55.

Figure 37:
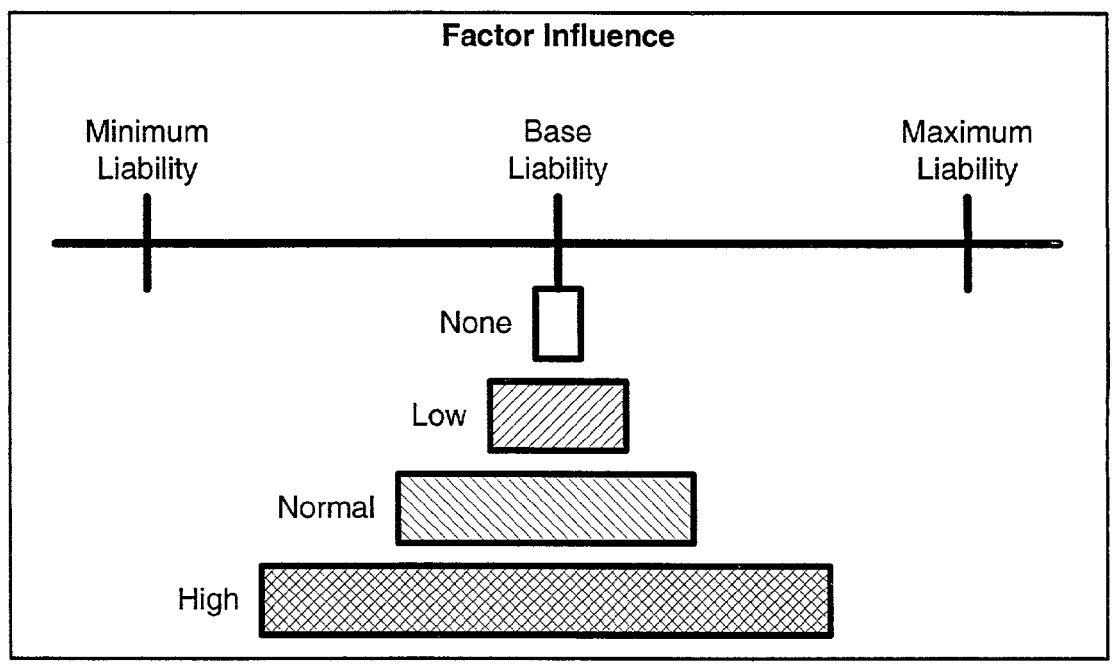
FIG. 37 illustrates the adjustment of a liability estimate by the factor influence according to one embodiment.

FIG. 37 is an illustration of how a factor influence may be used to adjust the effect of factors on the liability according to one embodiment. The factor influence may determine the effect the sum of the effects on liability resulting from factors may have on the base liability. As shown in FIG. 37, the factor influence may have four levels: none (no adjustment), normal, low, and high. A "high" factor influence may allow factors to modify the liability significantly. A "low" factor influence may reduce the influence of the factors below that determined by the "normal" factor influence. Each factor influence level may have a percentage value associated with it, for example, normal=100%, low=50%, and high=150%. Therefore, a "low" factor influence may cut in half the summation of all factor adjustments. In some embodiments, regardless of the factor influence setting, the lower and upper bounds of the liability may still constrain the final liability range.

Once a method is used to estimate the effect of the factors on the base liability, liability values ($L_A$ and $L_B$) for each vehicle may be calculated by combining the contribution for each vehicle with its corresponding base liability. Since the sum of the calculated liabilities may be greater than 100%, it may be necessary to calculate normalized liabilities from adjusted liabilities: $L_{AN}=L_A/(L_{AN}+L_A)$ and $L_{BN}=100\%-L_{AN}$. If $L_{AN}$ is greater than the upper bound, the final liability may be set equal to the upper bound. If $L_{AN}$ is less than the lower bound of the liability, the final liability may be set equal to the lower bound.

Alternatively, the effect of the factors on liability may be combined with the base liability according to a debit-credit method. A portion of the effect to liability of one vehicle may be added to that party's liability and the remainder may be subtracted from the other party's liability. For example, one half may be added to one party's liability and one half subtracted from the other party's liability.

In an embodiment, the liability may be expressed as a range rather than a single value. The range may be generated by a range radius. As used herein, the term "range radius" generally refers to a percentage value that may be added and subtracted from the final liability to create the range: $L_{AN}\pm$range radius. The range radius may be adjustable by the user and may be applied to all claims.

In one embodiment, a user may specify a range snap-to value. As used herein, the term "range snap-to" value generally refers to a multiple to round up or down to for the range. For example, the calculated liability may be 82±5%. If the range snap-to value is 5 percent, the liability may be adjusted to 80±5%.

The liability range may be adjusted if any part of it falls outside of the upper and lower bounds of liability. In one embodiment, the liability range may be shifted. If the maximum of the liability range is greater than the upper bound of liability, the maximum of the liability range may be shifted to the upper bound of liability. The minimum of the range may be shifted to the lower bound of liability if the liability range is larger than the upper bound to lower bound range. If the liability range is less than the upper bound to lower bound range, the minimum of the liability range may be shifted to the upper bound minus twice the range radius.

Similarly, if the minimum of the liability range is less than the lower bound of liability, the minimum of the liability range may be shifted to the lower bound of liability. The maximum of the range may be shifted to the upper bound of liability if the liability range is larger than the upper bound to lower bound range. If the liability range is less than the upper bound to lower bound range, the maximum of the liability range may be shifted to the lower bound plus the twice the range radius.

Alternatively, rather than shifting, the liability range may be truncated to keep as much of the original liability range as possible. If the maximum of the liability range is greater than the upper bound, the maximum of the range may be the upper bound of liability. If the minimum of the range is less than the upper bound, the minimum of the range may be the lower bound of liability.

In one embodiment, a knowledge acquisition utility may be provided to a user to allow the user to configure information associated with impact groups for roadway configuration/accident type combinations. For example, sets of impact groups associated with each roadway configuration and accident type may be configured. Further, each impact group may have one or more estimates of base liability associated with it. For example, each impact group in a roadway configuration and accident type combination may have a base liability, an upper range of liability, and a lower range of liability for each party associated with it. FIG. 38 is a screen shot of a window that may be used for selecting a roadway configuration/accident type combination according to one embodiment. As shown and discussed in reference to FIG. 8b, a given roadway configuration/accident combination may be associated with a plurality of impact groups where an impact group may be a collection of pairs of impact points. Impact points may be defined by the impact point diagram in FIG. 8a. Each of the pairs of impact points in the impact group may have the same base liability and lower and upper bounds of liability. A claims organization may designate a user such as an experienced claims adjusters to use the knowledge acquisition utility to determine the number of impact groups for each roadway configuration/accident type combination and the impact point pairs in each impact group.

A claims organization may further employ a user (e.g., an experienced claims adjusters) to assign base liabilities and lower and upper bounds of liability to each of the impact groups derived with the aid of the knowledge acquisition utility. As used herein, the term "knowledge acquisition utility" generally refers to an application that allows a claims organization to configure a system for estimating liability in an accident to meet the claims organizations needs. For example, the knowledge acquisition utility may allow the claims organization to set base liability, lower bound of liability and upper bound of liability for each impact group. The knowledge acquisition utility may also allow the claims organization to configure a numerical value associated with penalty factors. For example, a claims organization may use the knowledge acquisition utility to set a "low" penalty value equal to a 10% adjustment in liability. Likewise, a "medium" penalty value may be set at 20% and a "high" penalty value set at 30%. In various embodiments, other determinants of liability may also be configurable by the claims organization using the knowledge acquisition utility, including, but not limited to, situational weights associated with various factors, range radii, range snap-tos, etc.

In an embodiment, a knowledge acquisition utility may be used in conjunction with a tuning utility. A tuning utility may include a knowledge acquisition utility. In an embodiment of a tuning utility, the user may select a roadway configuration and accident type combination to edit from a window as described with reference FIGS. 38 and 39. The user may input base liabilities, lower, and upper bounds of liability for each of the impact groups corresponding to the roadway configuration/accident type combination. After the base liabilities are input, the user may run one or more pre-configured test scenarios built into the tuning utility. The user may then analyze the results and refine the base liabilities. The procedure may be repeated until the user is satisfied with the results produced by the liability estimation system. This process of entering estimates of liability or effect on liability, then testing those estimates by use or one or more pre-configured test scenarios is referred to herein as "tuning." The user may enter base liability information for all other roadway configuration and accident type combinations, run test scenarios, analyze output, refine tuning parameters, and repeat until satisfied. Likewise, the user may enter factor tuning information, as described with reference to FIG. 40, test each factor individually until satisfied, test combinations of factors, and adjust tuning parameters as necessary.

The window depicted in FIG. 38 contains a matrix 3800 of roadway configurations, R, and accident types, A. Diagrams representing roadway configurations are illustrated in FIG. 5. Diagrams representing accident types are illustrated in FIG. 4.

The elements of the matrix labeled with a "--" are combinations which may not be considered because the particular roadway configuration and accident type combination may be considered implausible. In the embodiment depicted, the implausible combinations are a subset of the combinations labeled with an "N" in FIG. 6. In some embodiments, all roadway configuration and accident type combinations may be available to the claims organization. In such embodiments, the claims organization may utilize the knowledge acquisition utility to designate one or more combinations implausible.

Figure 39:
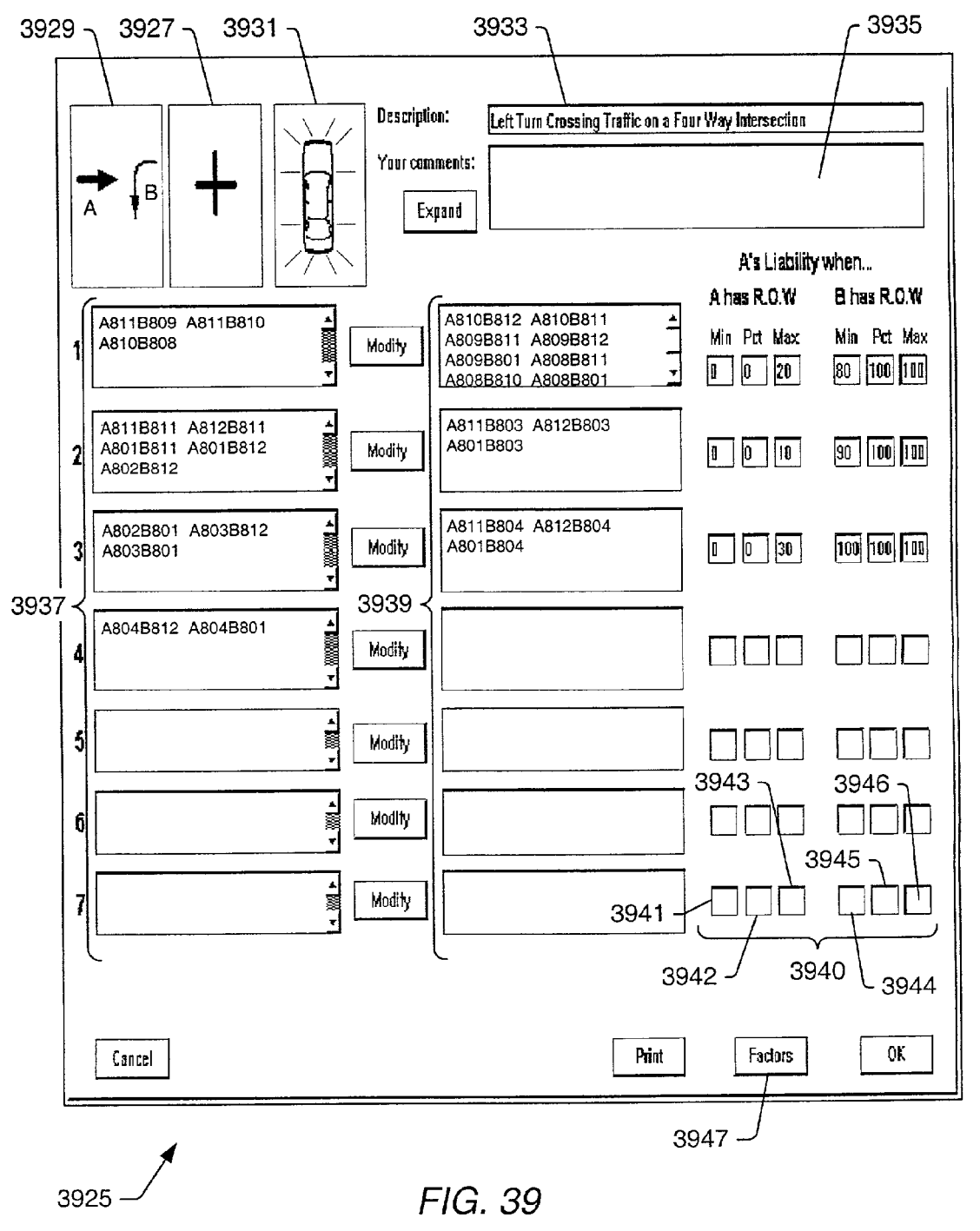

To configure a particular roadway configuration and accident type combination, a user may select the desired values of A and R from menus 3801 and 3803, respectively. Selecting Edit push-button 3805 may open an edit combination window (as depicted in FIG. 39), which may allow the user to edit impact groups for a given roadway configuration and accident type combination. Once a combination has been selected and configured, an indicator adjacent to combination 3807 may indicate that the combination has been configured. For example, a checkbox may be associated with each combination. In such embodiment, an "X" may appear in the check box to designate that a combination has been configured.

FIG. 39 is a screen shot of edit combination window 3925 from a knowledge acquisition utility according to one embodiment. The window may display a graphic representation of selected roadway configuration 3927 and accident type 3929. For example, in FIG. 39 the accident type shown is type 2, as shown in FIG. 4, and the roadway configuration is B, as shown in FIG. 5. A graphic representation of impact point diagram 3931 (as shown in FIG. 8a) may also be displayed. The window may display a text description of the accident type and roadway configuration combination 3933. For example, as depicted in FIG. 39, the text description may be, "Left Turn Crossing Traffic on a Four Way Intersection."

The user may also be provided with free-form text entry area 3935 to provide comments directed to the combination. For example, a claims organization may desire a particular comment to be displayed to a user entering claims information containing the combination.

Edit combination window 3925 may also include a plurality of impact group text areas 3937 configured to display impact groups and associated impact pairs. Associated with each impact group text area may be impact group edit area 3939. Impact group edit area 3939 may allow the user to enter one or more impact pairs to be associated with the impact group.

Also associated with each impact group text area 3937 may be liability input text area 3940. Liability input text area 3940 may include base liability field 3942, minimum liability field 3941, and maximum liability field 3943 associated with an accident where vehicle A has the right of way and base liability field 3945, minimum liability field 3944, and maximum liability field 3946 associated with an accident where vehicle B has the right of way. In an embodiment, liability input text area 3940 may allow the user to input estimates of liability for only one vehicle in the accident. For example, the liability input text area may be related to the liability of vehicle A only. In alternate embodiments, liability input text area 3940 may allow the user to input liability estimates for each vehicle. In either embodiment, liability input text area 3940 may display an estimate associated with a second vehicle. The liability estimate for the second vehicle may be determined from the liability estimates provided for the first vehicle on the assumption that liability must total to 100% between the two vehicles.

In an embodiment, the user may edit factors associated with the roadway configuration and accident type combination by selecting Factor button 3947 in editing combination window 3925. Selecting Factor button 3947 may bring up situational weight configuration window 3950, as depicted in FIG. 40.

FIG. 40 is a screen shot of situational weight configuration window 4001 according to one embodiment. Situational weight configuration window 4001 may be used to configure situational weights associated with one or more factors for a given roadway configuration and accident type combination. The situational weights may be used to adjust the magnitude of the effect of the factors on liability, as described with reference to FIG. 9a.

Situational weight configuration window 4001 may include a number of columns. First vehicle column 4003 (e.g., column "A") may include rows of data associated with a first vehicle (e.g., vehicle "A"). Second vehicle column 4007 (e.g., column "B") may include rows of data associated with a second vehicle (e.g., vehicle "B"). Factors column 4005 may include rows containing text descriptions of various factors. A user may select a situational weighting associated with each vehicle for each factor listed in factors column 4005. For example, in row 4009, the user has selected a "low" situational weight for vehicle A and a "high" situational weight for vehicle B for the speed factor.

In some embodiments, characteristics other than base liabilities, and factors may be adjusted by a knowledge acquisition utility. These characteristics include, but are not limited to, factor rankings, penalty values, range radii, range snap-tos, and absolute liability values. Alternatively, penalty values may not be tunable since they may be estimated by a method as illustrated in the flowcharts in FIGS. 10a to 36.

Figure 41:
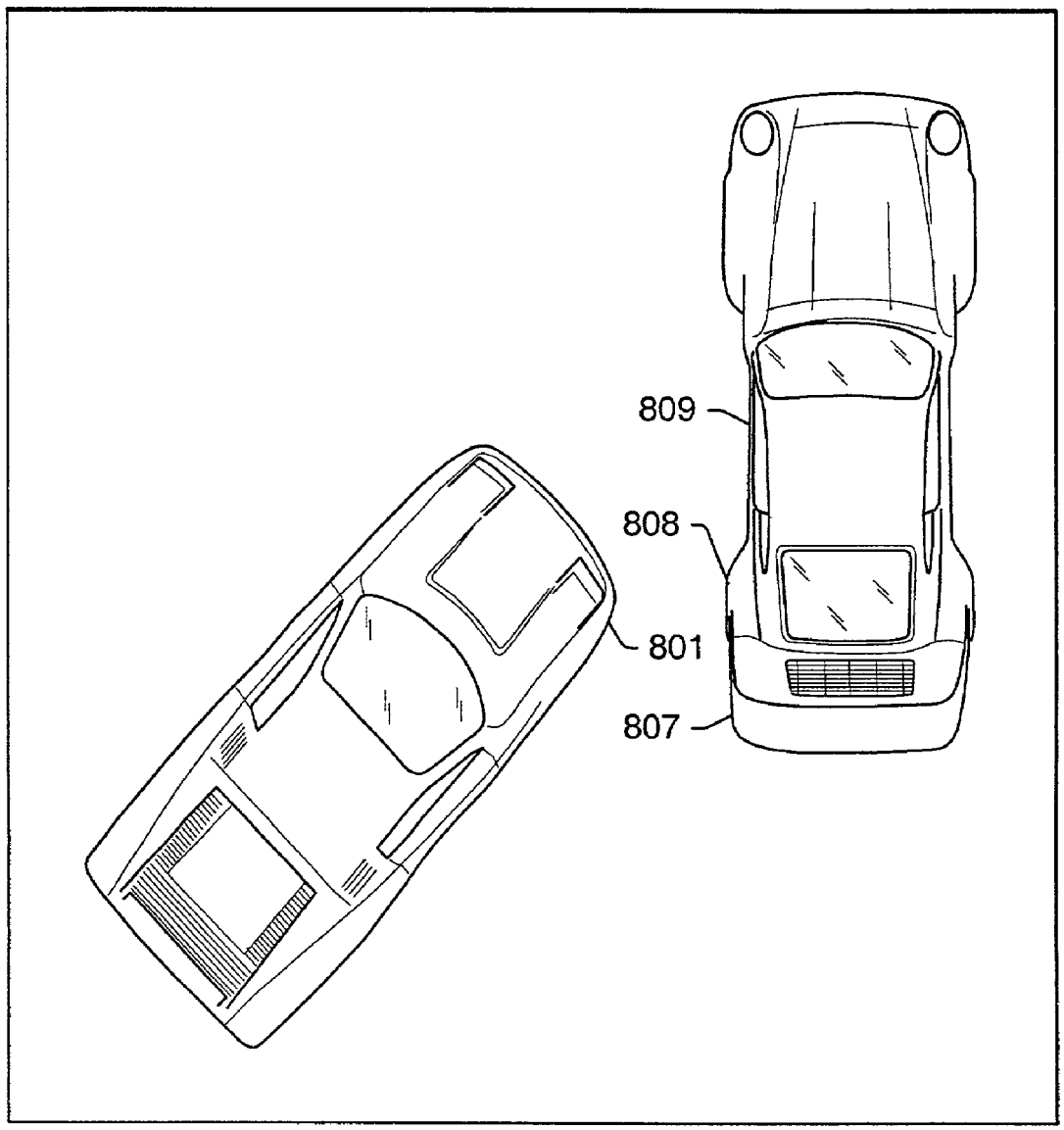
FIG. 41 is a screen shot of a Knowledge Acquisition utility or tuning utility for displaying pairs of impact points according to one embodiment.

FIG. 41 is a screen shot of impact point display window 4100 of a knowledge acquisition utility for displaying impact point pairs for a roadway configuration and accident type combination according to one embodiment. Impact point display window 4100 may provide a mechanism for displaying to the user of a knowledge acquisition utility what impact point combinations make up the impact group that is being considered by the user. Impact point display window 4100 along with the roadway configuration and accident type combination may provide a context within which to make decisions about base liability.

Impact point display window 4100 displays two vehicles with labeled impact points that belong to a given impact group. When the user selects an impact point on a first vehicle, the selected impact point and corresponding impact points on a second vehicle may be highlighted. The selected impact point on the first vehicle and the highlighted impact points on the second vehicle are pairs of impact points in the impact group. For example, in impact point display window 4100, impact point (801) on the vehicle on the left is selected resulting in impact points (807), (808), and (809) being highlighted on the vehicle on the right. Therefore, (801, 807), (801, 808), and (801, 809) are pairs of impact points.

FIG. 42 illustrates a screen shot of Claim Data window 4200. Claim data window 4200 may be divided into a number of frames. Control frame 4201 may provide access to basic controls for the application. For example standard pull down menus may provide access to file, edit, tool and help menus as are commonly used. Additionally, controls frame 4201 may include a number of frame selection buttons (e.g., buttons 4203, 4205, 4207, 4209, 4211, and 4213). Each frame selection button may cause a data display frame 4250 to display different data. For example, selecting "ROW" frame selection button 4205 may cause data regarding right of way in a vehicle accident to be displayed. Claim data window 4200 may also include claim data frame 4225. Claim data frame 4225 may include basic claim data associated. In some embodiments, claim data frame 4225 may continuously display the basic claim data while data display frame 4250 allows other data related to the accident to be entered. Accessories frame 4275 may allow the user to select a number of tools that may be useful to the user as claim data is being entered. Legal reference button 4277 may allow the user to access information related to the laws of a jurisdiction in which the accident took place. Calculator button 4279 may allow the user to access a calculator feature. Comments button 4281 may allow the user to access a free-form text entry area in which comments may be entered. Show details button 4283 may allow the user to access a summary report screen that displays details related to the accident.

Claim data frame 4225 may contain data entry fields including, but not limited to, a claim number, a policy number, an accident location, who reported the accident, whether police where called, what branch of the police was called, whether there were any injuries, whether there were fatalities, what state the accident took place, the date of the accident, what time the accident took place, a policy start date, a policy end date, who the accident was reported to, and a description of the loss due to the accident. In an embodiment, a system may access a claims organization's database to retrieve information related to a policy or an insured party based on a policy number. For example, the policy start and end dates may be automatically entered by the system based on information in the claims organization's database.

Figure 43:
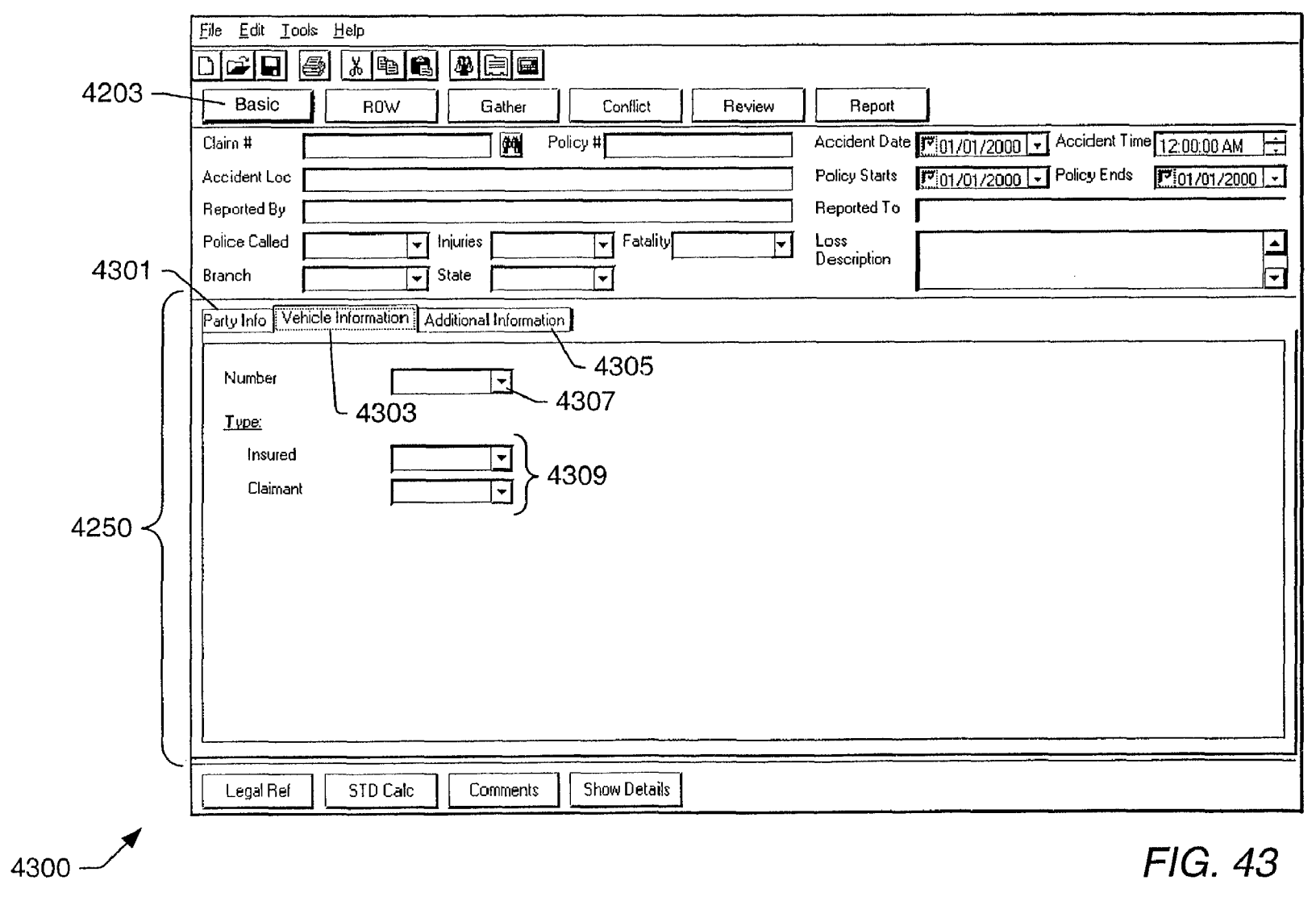

Vehicles frame 4300, as depicted in FIG. 43, depicts a frame for entering data related to the vehicles involved in the accident according to one embodiment. Vehicles frame 4300 may appear in data display frame 4250 if the user selects "Basic" frame selection button 4203 and vehicle information frame tab 4303. Other options available to the user when "Basic" frame selection button 4203 is selected may include party information frame tab 4301 and additional information frame tab 4305. The user may enter the number of vehicles involved in the accident in number field 4307. The user may enter the types of each vehicle in type fields 4309. In an embodiment, the number of type fields provided may correspond to the number of vehicles entered into vehicles field 4307. In some embodiments, two type fields 4309 may be provided by default. In such embodiments, a first type field may correspond to the insured party's vehicle type, and a second type field may correspond to the claimant party's vehicle type. In such embodiments, additional type fields may be provided if more than two vehicles were involved in the accident. Vehicle types may include, but are not limited to, an automobile, a light truck, and another type.

Figure 44:
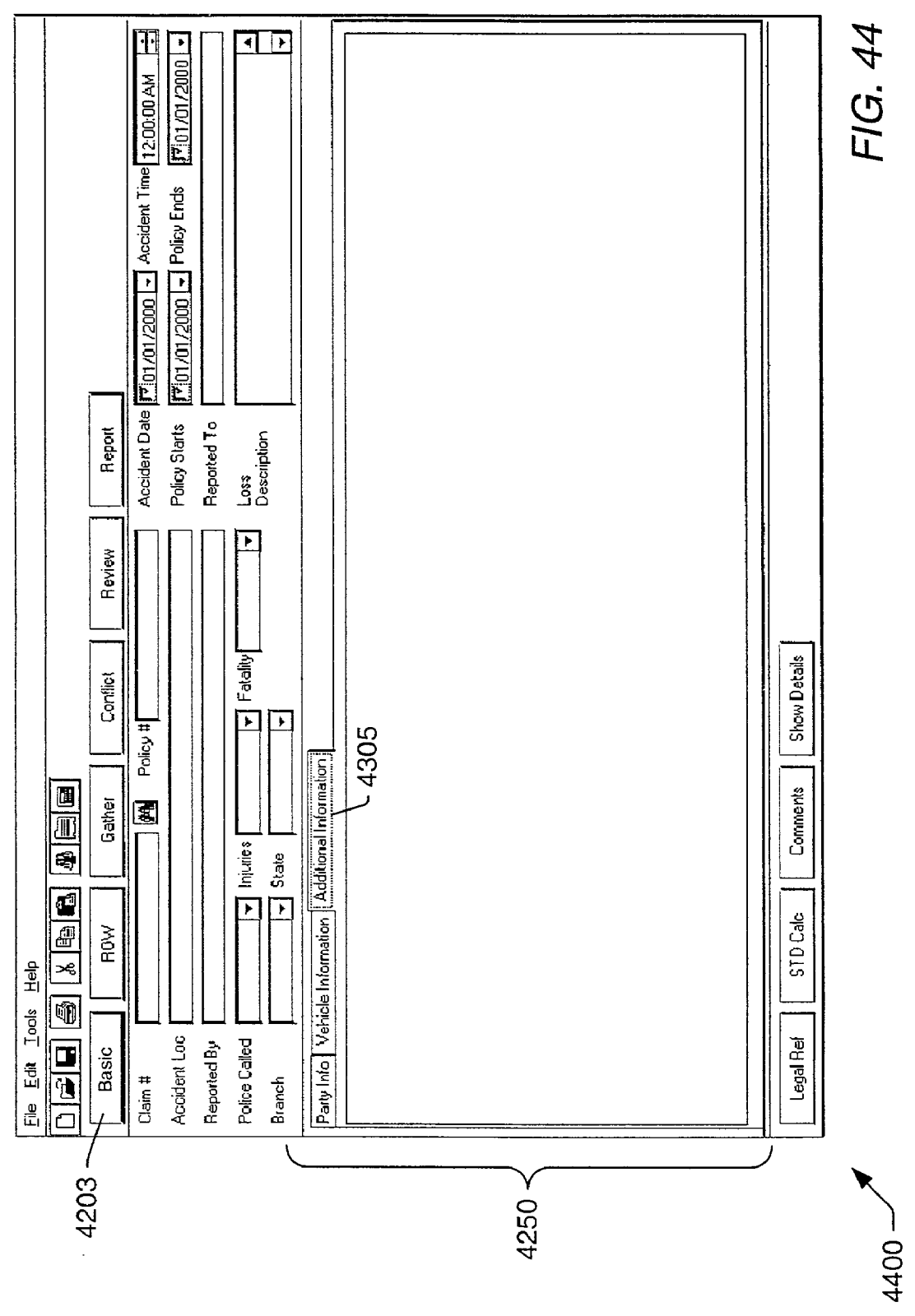

FIG. 44 is a screen shot of additional information screen 4400. Additional information screen 4400 may be displayed when Additional Information tab 4305 is selected. Additional information screen 4400 may allow the user to enter a description of the accident in a free-form text entry box.

Figure 45:
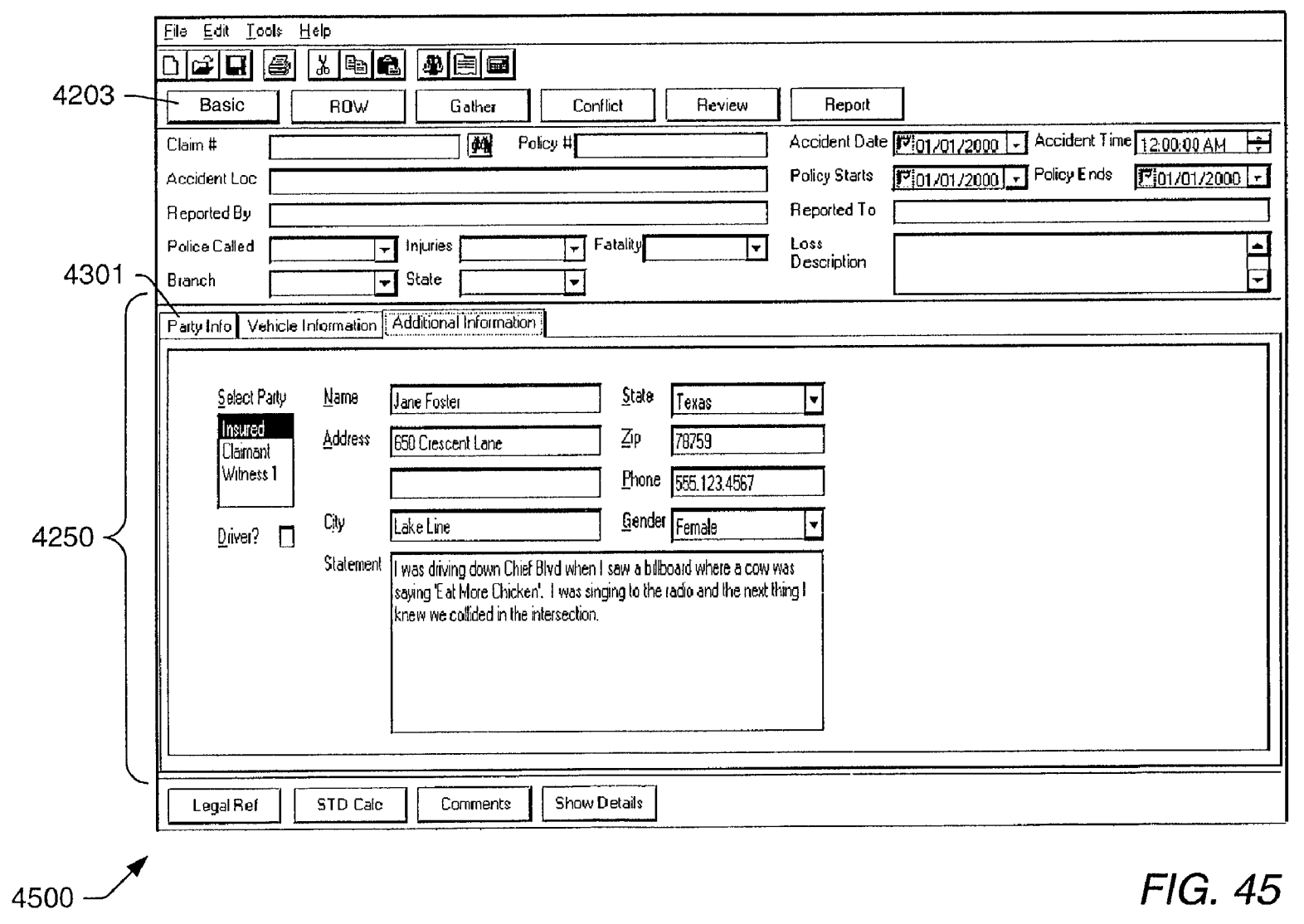

FIG. 45 illustrates a screen shot of party information frame 4500. Party information frame 4500 may be displayed in data display frame 4250 when Party Information tab 4301 is selected. The user may be prompted to select a party involved in the accident from the menu that may include: Insured, Claimant, or Witness. The user may be presented with input fields related to identifying information specific to the party selected. For example, the user may enter the selected party's name, address, city, zip code, phone number, gender, and state into entry fields. The user may enter a description of the accident made by the party into a free-form text entry box.

Figure 46:
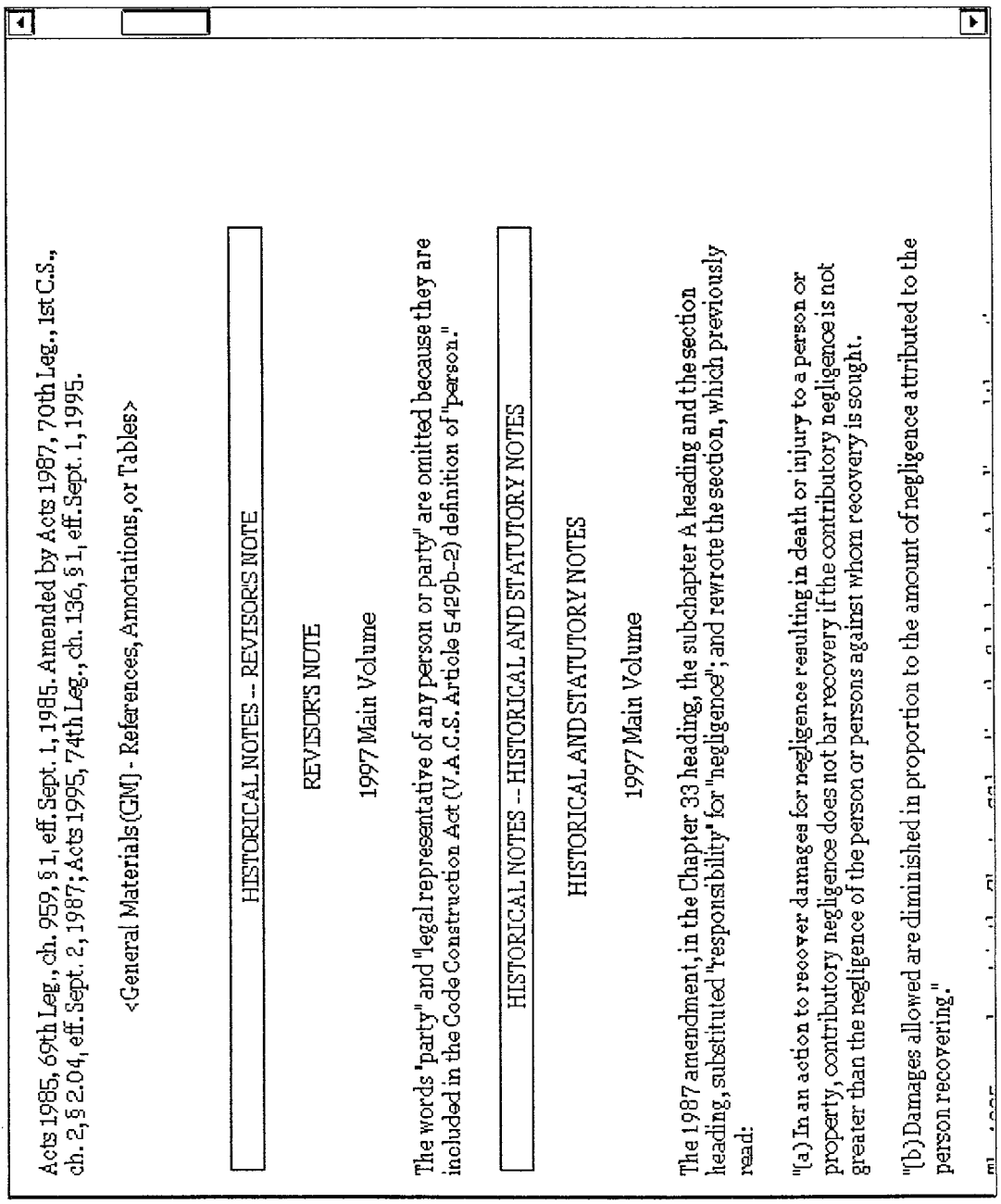
FIG. 46 is a screen shot of a Legal Reference window according to one embodiment.

FIG. 46 depicts an embodiment of a legal reference screen. The legal reference screen may be accessed by selection of legal reference button 4277 in accessories frame 4275. The legal reference screen may provide the user with legal information for a jurisdiction in which the accident occurred. The legal information may be pertinent to determining liability in the accident. In an embodiment, the legal reference information may be accessed from a subscription legal reference service, such as the Westlaw legal information service, available from West Group of St. Paul, Minn. For example, laws pertaining to proportionate responsibility for the jurisdiction may be displayed. The jurisdiction may be determined by the state selected in claim data frame 4225.

Figure 47:
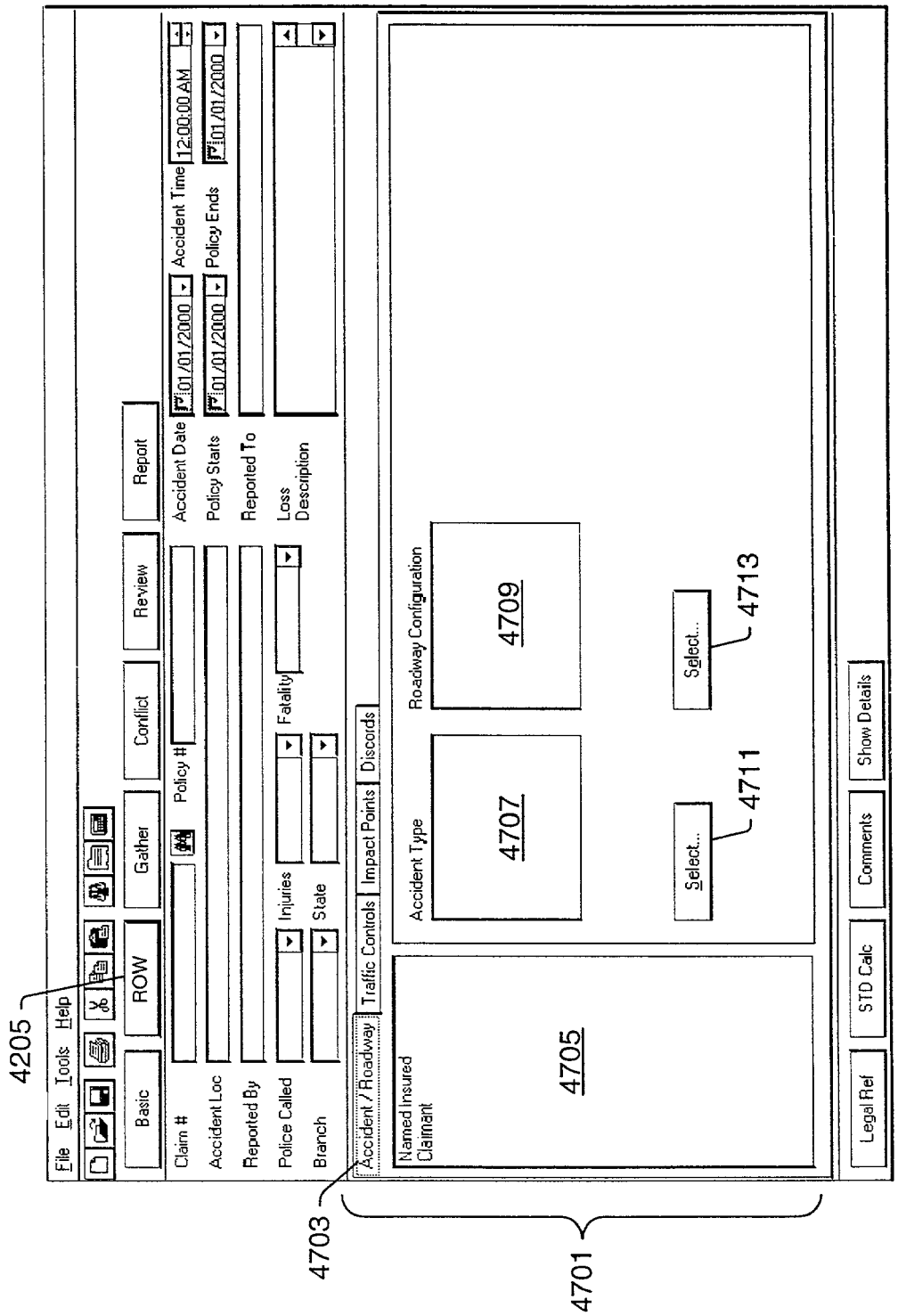
FIG. 47 is a screen shot of a Right of Way data frame according to one embodiment.

FIG. 47 illustrates an embodiment of right of way data frame 4701 that may be displayed if a user selects right of way button 4205 in controls frame 4201 and "Accident/Roadway" tab 4703. Based on data provided in right of way frame 4701, the system may determine a right of way in an accident by a method described with reference to FIGS. 7a and 7b. In some embodiments, a right of way data frame may allow a user to make a manual determination of right of way. Accident/Roadway tab 4703 may present a user with a list of vehicles involved in accident 4705 and selection frames for accident type 4707 and roadway configuration 4709. Accident type frame 4707 may display a graphical representation of a currently selected accident type. Roadway configuration frame 4709 may display a graphical representation of a currently selected roadway configuration. A user may select a different accident type or roadway configuration by using selection buttons 4711 and 4713, respectively.

FIG. 48 illustrates an embodiment of traffic controls data frame 4801 that may be displayed if a user selects right of way button 4205 in controls frame 4201 and "Traffic Controls" tab 4803. Using traffic controls data frame 4801, the user may enter information regarding one or more traffic controls that may have been present at the scene of an accident. The user may indicate a primary and a secondary traffic control in "primary traffic control" field 4805 and "secondary traffic control" field 4807, respectively. The user may also indicate if a traffic control was disobeyed in field 4809. The user may also indicate if a traffic control was partially obscured in field 4811. The user may indicate if a traffic control was completely obstructed or missing in field 4813. The user may indicate if an intersection appeared uncontrolled at the time of the accident in field 4815. Information provided in fields 4809, 4811, 4813, and 4815 may be used to determine the effect of a missing or defective traffic control on liability on the accident.

Figure 49:
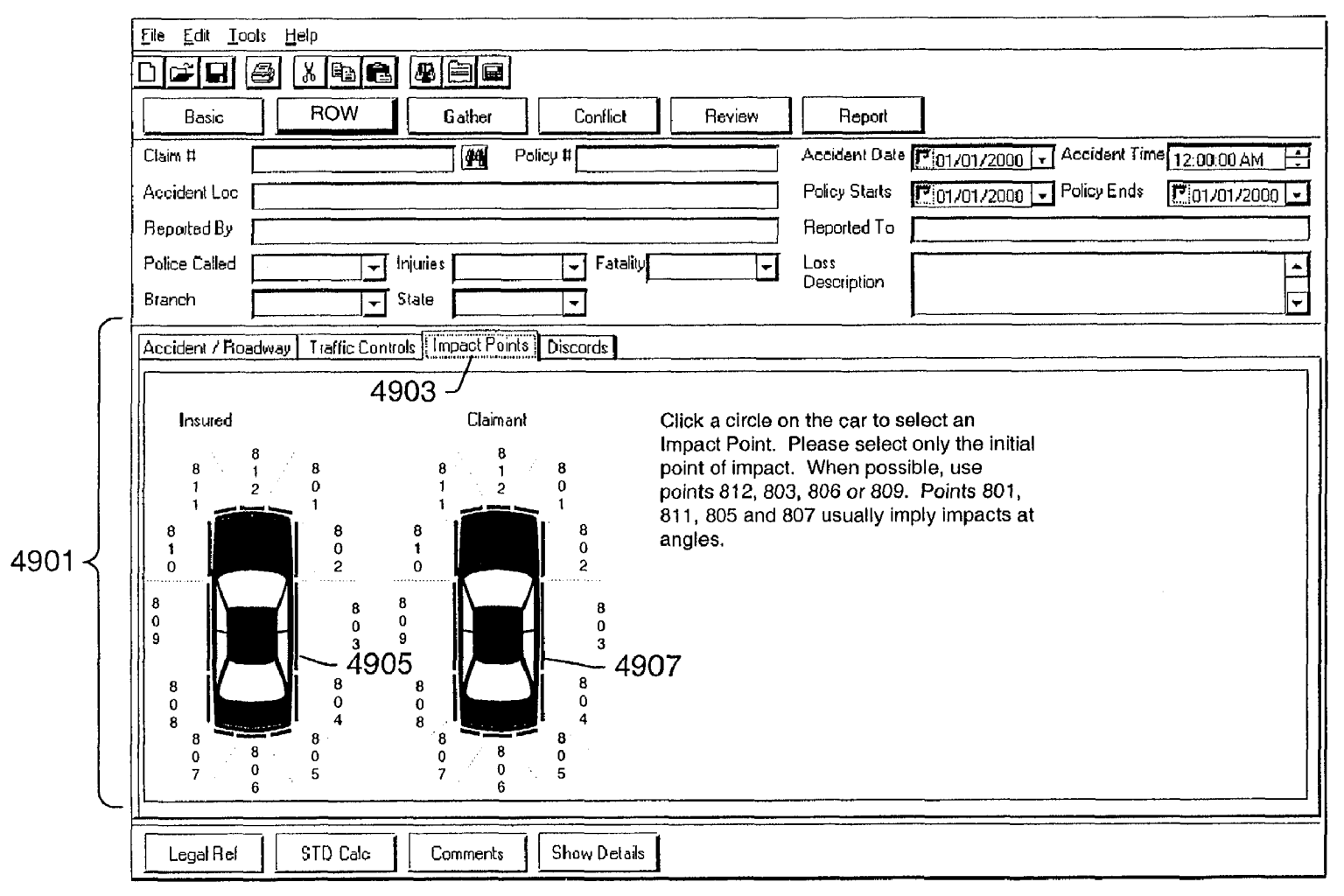

FIG. 49 illustrates an embodiment of impact points data frame 4901 that may be displayed if a user selects right of way button 4205 in controls frame 4201 and "Impact Points" tab 4903. Using impact points frame 4901, the user may enter information regarding impact points for each vehicle in the accident. In an embodiment, impact points data frame 4901 may present the user with graphical representations of the vehicles involved, referenced by numerals 4905 and 4907. In such embodiments, the user may be able to select the impact points on the graphical representation.

Figure 50:
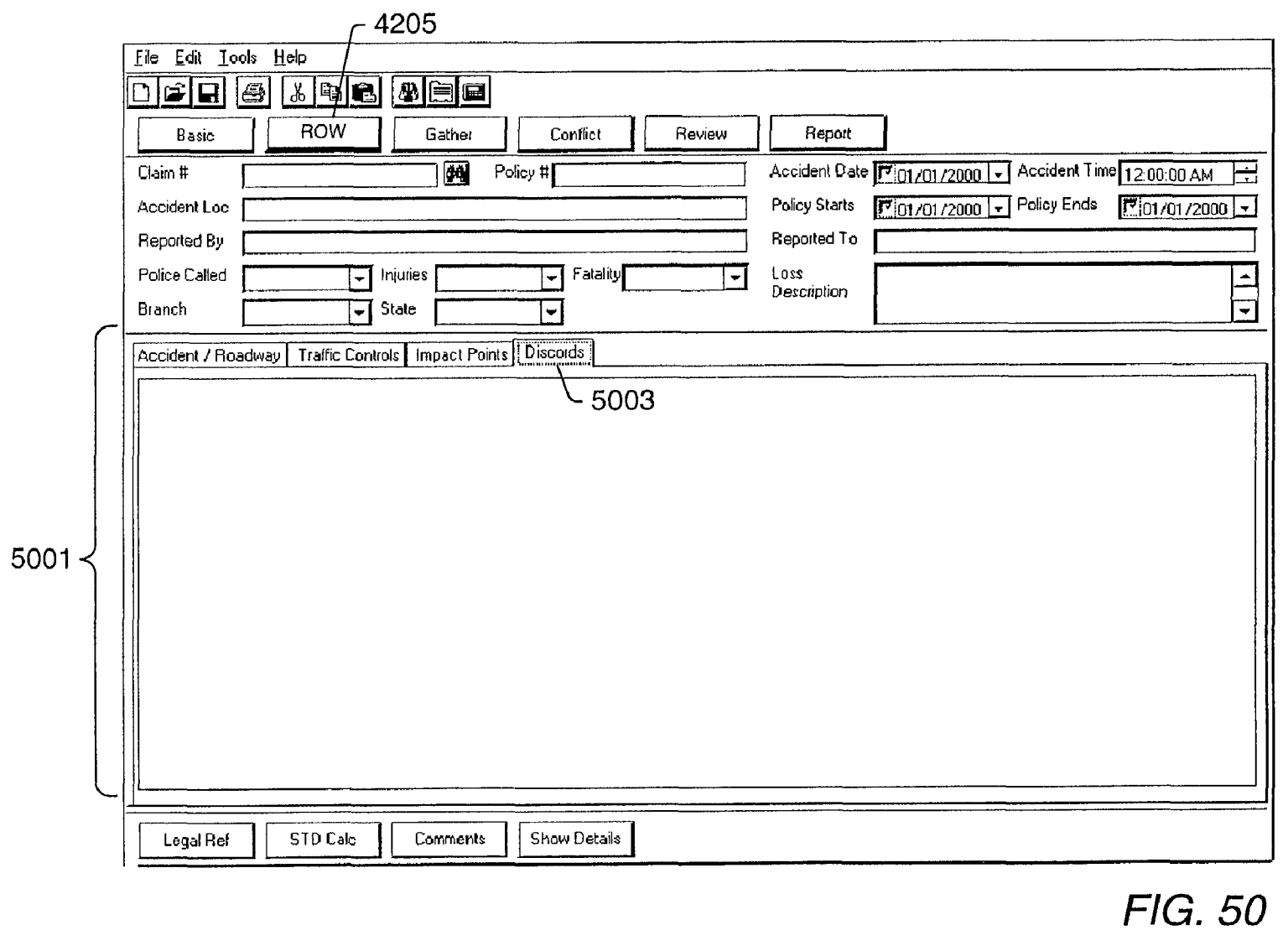

FIG. 50 illustrates an embodiment of discords report frame 5001 that may be displayed if a user selects right of way button 4205 in controls frame 4201 and "Discords" tab 5003. As a user selects information describing an accident, two or more pieces of information may describe an implausible circumstance. For example, an accident type of head on may be selected with a roadway configuration of merging from the left. This accident type and roadway configuration may be unlikely to occur. Discord report frame 5001 may display a report indicating to the user that an unlikely combination has been selected. This may allow the user to change one or more selections, or to proceed to a manual assessment of the accident using the existing selections.

FIG. 51 illustrates an embodiment of factors input frame 5101 that may be displayed if a user selects gather 4207 in controls frame 4201. Factors input frame 5101 may provide input area 5105 for each vehicle involved in the accident. For example, as depicted in FIG. 51, factors input frame 5101 has an input area for a claimant and an insured. The claimant input area may be accessed by selecting claimant tab 5103. Each input area 5105 may include questions column 5107, which may list questions to be asked during an accident investigation. Alternately, in some embodiments, questions column 5107 may provide a column of input fields in which an adjuster may enter questions that were asked during the accident investigation. Some embodiments may include both an area to input adjuster originated question and a list of system prompted questions.

Questions asked may pertain to individual factors or groups of factors. Factors category selection area 5104 may allow the user to select an individual factor or a category of factors for which information may be input. For example, by selecting a visibility factor category from factor category selection area 5104, the user may be provided a list of questions related to the visibility factor as described with regard to FIG. 35.

Factors input area 5101 may also include one or more versions columns for entering responses to questions provided by various parties. For example, insured version column 5109 and claimant version column 5111 are depicted in FIG. 51. If other parties provide answers to one or more questions, additional version columns may be generated by selecting add version button 5113. Alternately, a version column may be deleted by use of delete version button 5115. Version columns may be used to enter responses provided by a party regarding the questions in questions column 5107.

Figure 52:
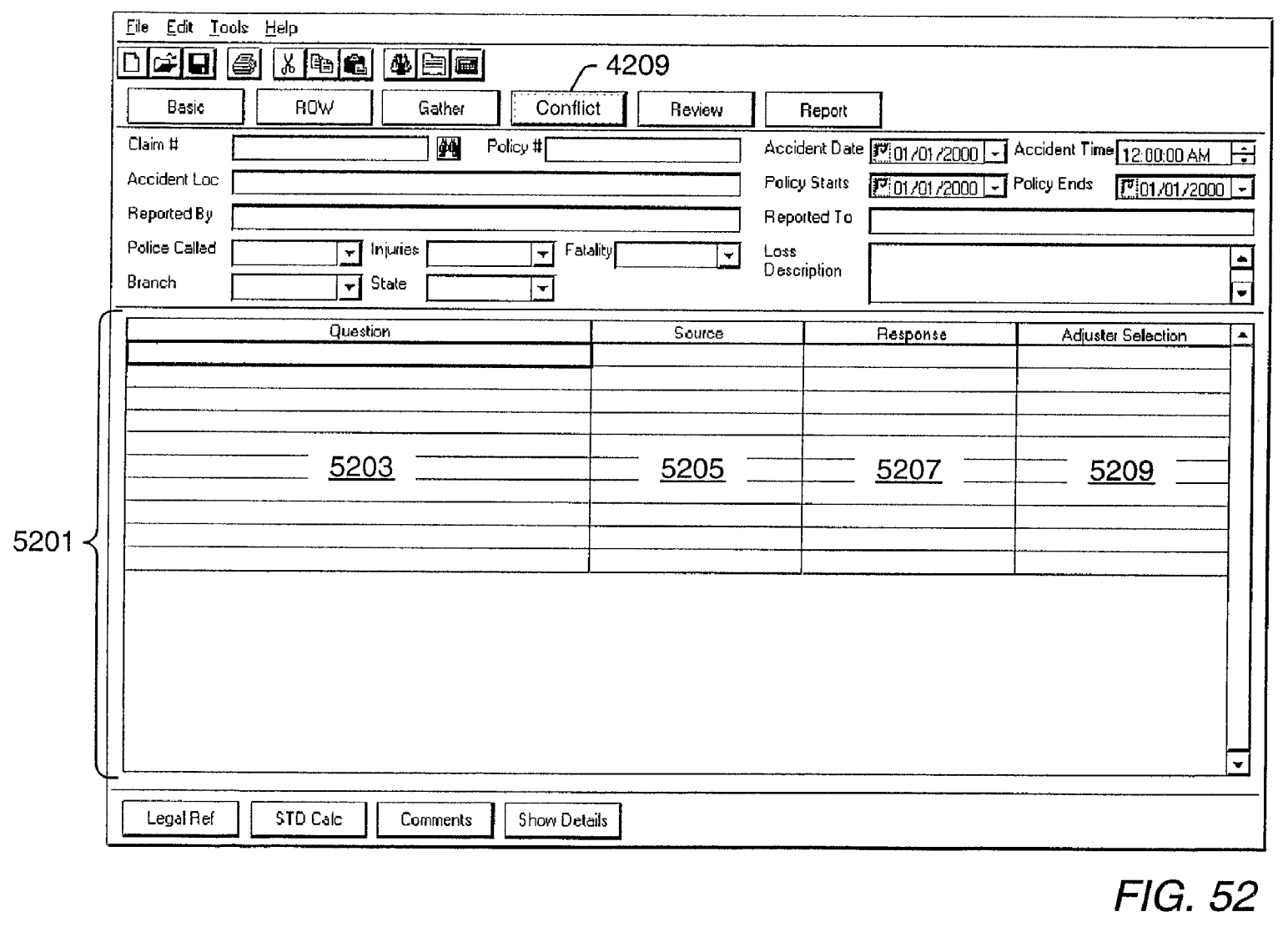

FIG. 52 depicts an embodiment of conflict identification frame 5201 according to one embodiment. Conflict identification frame 5201 may assist an adjuster in identifying two or more answers from witnesses that appear to be in conflict with one another. The assessment of liability in a motor vehicle accident may involve analysis of multiple statements of the description of an accident. In one embodiment, the consistency between different witness statements may be assessed. The statements may be from the drivers or passengers of vehicles involved, bystanders and/or other drivers not involved in the accident. In some instances, statements provided by these various witnesses may not agree on all of the details of the accident. For example, details that may be important in assessing liability may include, but are not limited to, speed of the vehicles, whether brakes were applied, whether signaling was improper or nonexistent, whether a vehicle yielded, the road condition, the road character, road defects, whether a traffic control was defective, visibility, whether a driver was wearing required corrective lenses, distance between the vehicle before the accident, whether headlights were off, the presence of an animal/pedestrian/other vehicle, whether a vehicle made a sudden stop or swerve, whether taillight or brake lights were off, whether a vehicle undertook unsafe backing, whether there was failure to take evasive action, whether a vehicle had high beams on, and whether a lane change was improper.

The system may compare answers given by each witness to various questions to determine if inconsistencies exist. In an embodiment, inconsistencies may be identified even if witnesses were not asked the same questions. For example, the system may flag an inconsistency if a driver answers no when asked, "Did you consume any alcohol prior to the accident?" but a witness answers yes when asked, "Did the drive of the vehicle seem to be impaired?" Claims adjusters may use details that are described inconsistently for informational purposes. The system may list inconsistencies identified in tabular form in conflict identification frame 5201. Details with inconsistent versions may be noted in the tabulation of results. For example, question column 5203 may list a general question having inconsistent responses. Continuing the previous example regarding alcohol, question column 5203 may contain the question, "Did the alcohol contribute to the accident?" Regarding the general question in column 5203, source column 5205 may list each source that provided an answer regarding the question. Response column 5207 may list responses associated with each source. Conflict identification frame 5201 may further provide the user with adjuster selection field 5209. Adjuster selection field 5209 may allow the user to select a response that the adjuster desires to designate as accurate. In other embodiments, the system may identify a most likely version of the accident. The most likely version may correspond to the version with the most responses that are consistent across all of the witnesses. For example, if 5 witnesses were asked about a particular detail and three provided consistent answers, the system may flag these answers as the most likely version of the accident.

Figure 53:
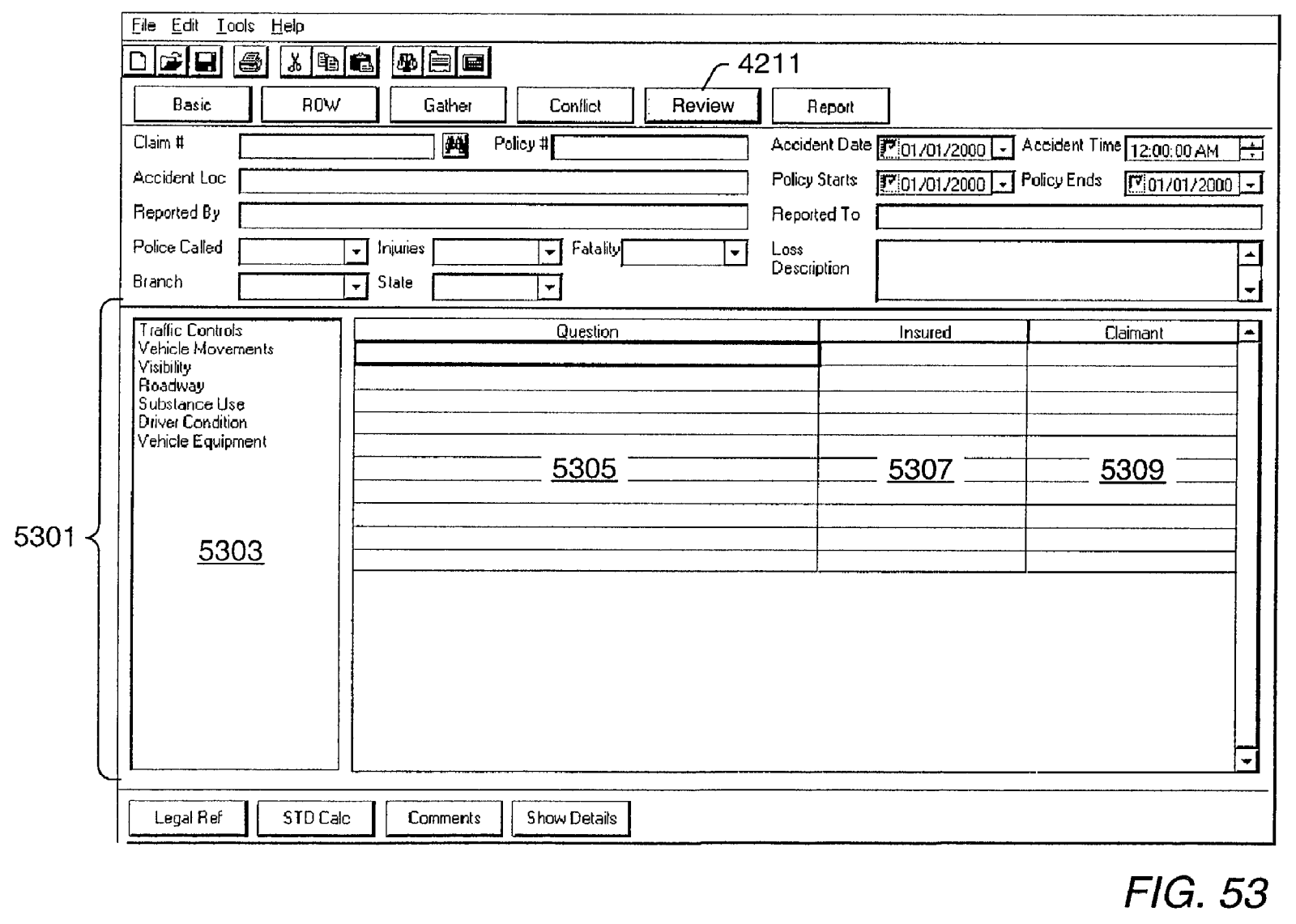

FIG. 53 depicts an embodiment of review frame 5301. After a determination of a most likely version of the accident has been made, the user may be provided with review frame 5301 to review the responses retained as the most likely version of the accident. The user may select a category of factors to review from a list of categories of factors 5303. Questions applicable to the selected category of factors may be displayed in questions column 5305. Answers from the determined most likely version of the accident may be displayed in answers columns 5307 and 5309.

In certain circumstances, the system may not be able to determine an accurate estimate of liability. For example, highly unusual circumstances of the accident may inhibit accurate assessment by the system. In such cases, manual assessment input screen 5401 may be provided, as depicted in FIG. 54. Manual assessment input screen 5401 may include insured liability field 5403 and claimant liability field 5405. Additionally, manual assessment input screen 5401 may include comments field 5407, where the user may provide comments regarding the need for the manual assessment and/or circumstances related to the accident.

Figure 55:
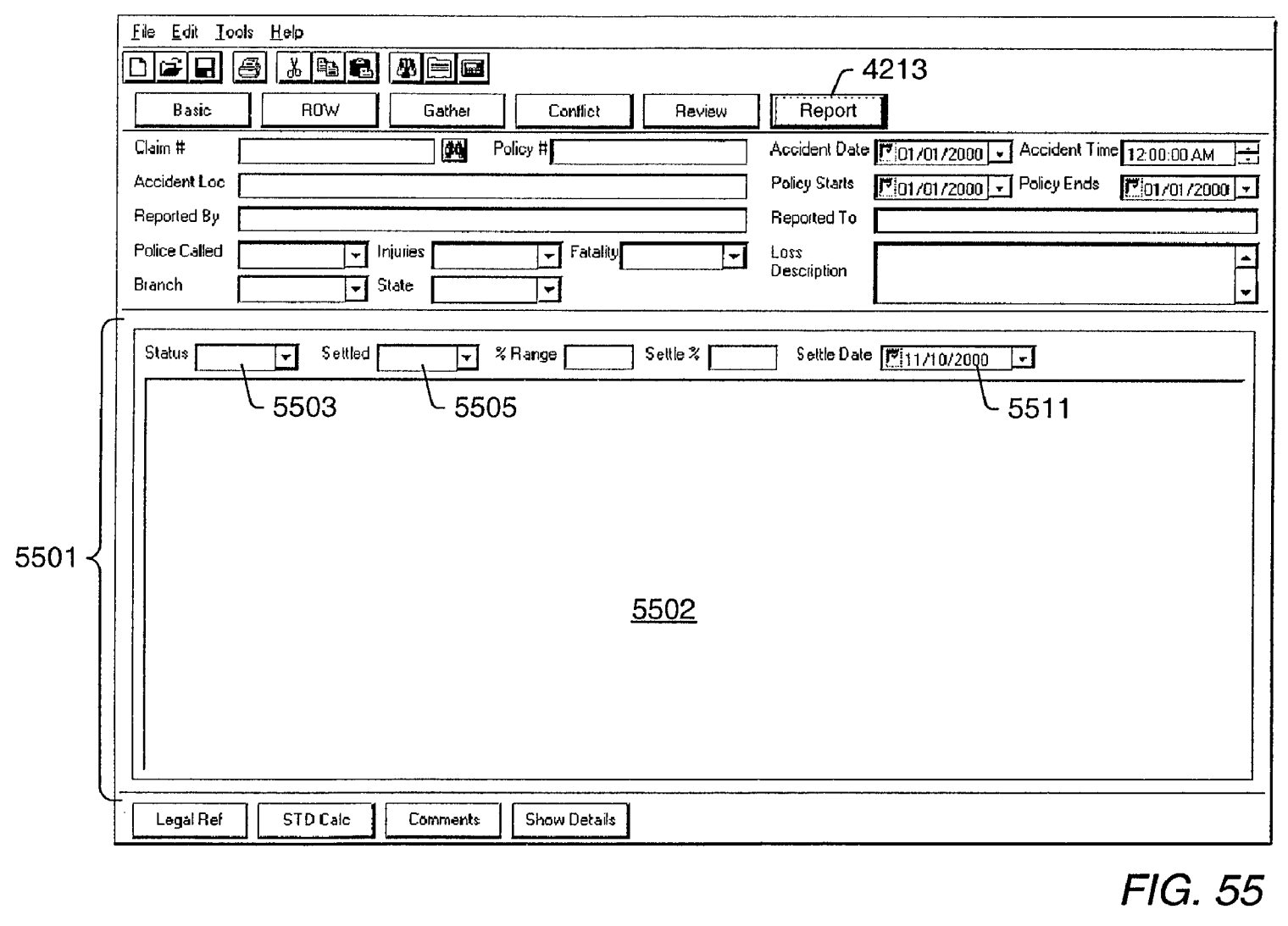

FIG. 55 depicts Consultation Report frame 5501 according to one embodiment. Consultation Report frame 5501 may include text box 5502 for displaying an Assessment Summary report. The Assessment Summary report may include a summary of data gathered and an assessment of liability. For example, the Assessment summary report may include, but is not limited to, the Claim Number, the minimum and maximum percentage of liability, the accident type, the roadway configuration, comments regarding one or more factors, proximate cause, accident date, whether the accident involved injuries, whether the police were called, the accident location, accident description, who the accident was reported by and reported to, jurisdiction, relevant traffic laws of the jurisdiction, identity of the claims adjuster that addressed the claim, and vehicle information for each vehicle. Vehicle information may include the Vehicle Identification Number ("VIN"), make, model, year, impact point, vehicle type, right of way, speed, factors that apply to the vehicle, and party who was driving the vehicle.

The user may indicate whether the assessment is complete or incomplete by using Assessment Status field 5503. The user may indicate whether the claim has settled using Settled field 5505. A settlement date may be entered in Settlement Date field 5511.

In an embodiment, notes may be added to an Assessment Summary report depending on the determination reached for each factor. With reference to FIGS. 10a to 36, each terminus of each factor may have a report message code associated with it. Report message codes listed in an assessment report may aid the adjuster in explaining the assessment and/or in negotiating a settlement. It may be especially helpful to the adjuster to have talking points reached in the assessment listed in the assessment report.

In an embodiment, other reports may be available to a user as well. For example, a user may be able to configure ad hoc reports related to historical accidents. The system may also provide one or more pre-configured reports. For example, a number of administrative or business reports may be available. Such reports may include, but are not limited to, reports pertaining to previous settlements reached, accidents claimed in a particular region or under a particular policy, and accidents associated with various categories of drivers or vehicles.

In another embodiment, a graphical user interface similar to that illustrated in FIGS. 42 to 54 may be combined with accident reconstruction methodology to assess the credibility of details in witness accident descriptions. Accident reconstruction software may be applied to determine details relating to speed, time, and distance of the vehicles involved in the accident. Such details may be inferred by accident reconstruction software from physical measurements. For example, the impact speed may be inferred from physical damage to vehicles. The results of the accident reconstruction software may then be compared to the description of the corresponding detail in the witness statements. The credibility of a witness statement may then be evaluated according to its consistency with the results of the accident reconstruction software.

Accident reconstruction software may employ accident reconstruction methods that may be dependent on a number of variables. Variables may be related to the preservation of the accident evidence, limitations in available specifications, and choice of accident reconstruction techniques. Accident reconstruction techniques may include damage-based and trajectory analysis techniques.

Variables related to accident evidence include the facts of the particular case, which may be unique for the case. Generally, access to some facts may not be under the direct control of an accident reconstructionist, however, the reconstructionist may request documentation and/or memorialization of these facts. The facts of a case may form the basis for the reconstruction. Facts may be preserved or memorialized in photos or measurements by police or other investigators at the time of the accident.

Accident evidence may include positions of rest of vehicles in the accident (e.g., where they stop), tire marks, roadway markings, damage to vehicles, and damage to property. The memorialization of these items may vary widely between cases. First, accident investigators (e.g., police on the scene of the accident) may identify the important aspects of the accident required to permit a detailed reconstruction. The determination of the requirements of a reconstruction may be incidental to other activities, for example, life-saving or the restoration of a safe environment to the accident site. An investigator may try to preserve as much of the evidence as possible. In this initial phase of memorialization, photography, paint markings of vehicles' positions of rest, impact marking, and debris may be used to preserve evidence. It may be advantageous to photograph items of evidence before putting paint marks on. Techniques for measuring various items at the scene may include sight estimates, pacing, tape measurements, and surveying type equipment. The variation in the accuracy of these techniques may detract from the ultimate accuracy of the speed estimates.

The vehicle damage data may not necessarily be preserved at the scene. Typically, vehicle damage may remain unchanged for weeks and/or years at a separate location while either waiting for repair or disposal.

Measurement of the extent of vehicle damage may be subject to some variation. However, typically, the variation of results of a damage-data based reconstruction may mainly be due to differences in the reconstruction and interpretation techniques rather than to the measurement devices used.

Measurements and vehicle specifications may be used as inputs to the equation that permit application of various physical laws to the accident reconstruction. Specifications may include the mass of the vehicles. Measurements may include the geometry of the collision. Determining the geometry of the collision may require the dimensions of the vehicles as inputs.

Additional specifications that may be used in a reconstruction may include roadway friction coefficients, wheel drag, and wheel steer, which may be used primarily for trajectory-based analysis. The friction coefficient, drag, and steer on the vehicle as it travels from impact to rest may be used to approximate the kinetic energy dissipated in a trajectory-based analysis.

The two general techniques for accident reconstruction include damage-based and trajectory-based methods. Damage-based methods typically reconstruct accidents based on damage to vehicles without applying accident scene data. Damage-based only reconstruction techniques generally assume a virtual linear relationship between the impact speed changes versus residual or static crush. The relationship is virtual since it involves equating the crush energy dissipated during the dynamic crushing of the vehicles to the residual or static crush. Damage-based reconstruction techniques may use a single full-scale crash test data point for a given vehicle combined with an assumption regarding a "no-damage" intercept to calculate custom-fitted coefficients for use in individual case reconstructions. Such an assumption may generally be recognized as a crude first-approximation procedure. Alternatively, some damage-based techniques may use multiple crash tests on an individual vehicle to create multiple data points for a given vehicle.

A trajectory-based analysis may directly provide estimates of the impact speed changes in the form of the differences between impact and separation velocities for each vehicle. The general concept or principle of a trajectory-based reconstruction may be the conservation of momentum. The conservation of momentum, which is based on Newton's second and third laws, is that the total momentum of an isolated system of masses remains constant. The conservation of momentum principle may serve as the theoretical basis for reconstruction of impact speeds in vehicle-to-vehicle collisions. The principal stipulates that the system momentum preceding a collision and the system momentum after a collision, for example at separation, are conserved in the absence of external forces. Therefore, if the individual speeds and directions of motion for each of the two vehicles in a collision to travel from separation to rest can be determined, then the direction and magnitude of this system momentum may be used to determine the magnitudes and directions of the velocities that may have existed prior to the collision, which are the impact velocities. Generally, the magnitude of external forces produced by the tires and other possible sources such as gouging and scraping of vehicle components on the ground during the collision may be considered small when compared to the magnitude of the forces of the collision. However, it may be necessary to consider such external forces for a comprehensive accident reconstruction.

Analyzing the total energy dissipated as the vehicles travel from separation to their positions of rest may be important for preparing a comprehensive trajectory-based reconstruction of a collision. When vehicles separate after a collision, they may move to rest positions against resistance forces produced primarily by tire-to-ground friction. Secondary contacts, which may occur with roadside obstacles and/or terrain features, may play significant roles in the dissipation of kinetic energy and may also produce redirection of the spinout trajectories.

In another embodiment, a graphical user interface like that illustrated in FIGS. 42 to 54 may be combined with a credibility assessment method to create a reliable accident description. The details relevant to the accident such as those described herein may be tested by a credibility assessment method such as the accident reconstruction software as described herein. The most credible version of the details may then be combined into a single, reliable version of an accident description.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of estimating liability for a vehicle accident, comprising:
   providing to a computer system a real set of characteristics of a real vehicle accident involving two or more vehicles, wherein the real set of characteristics of the real vehicle accident comprises:
      an accident type for the real vehicle accident, wherein the accident type for the real vehicle accident specifies a relationship between two or more vehicles' paths on a roadway at the time of the real vehicle accident; and
      a roadway configuration for the real vehicle accident,
   wherein the computer system is configured to access a memory, and wherein the memory comprises sets of characteristics for past or theoretical vehicle accidents, wherein the past vehicle accidents are accidents that actually occurred in the past, wherein the theoretical vehicle accidents are accidents that might occur, wherein the set of characteristics for at least one of the past or theoretical vehicle accidents comprises:
      an accident type for the past or theoretical vehicle accident, wherein the accident type for the past or theoretical vehicle accident specifies a relationship between two or more vehicles' paths on a roadway at the time of the past or theoretical vehicle accident; and
      a roadway configuration for the past or theoretical vehicle accident;
   wherein each of at least two of the sets of characteristics for the past or theoretical vehicle accidents is associated with at least one base liability;
   the computer system automatically determining a right of way in the real vehicle accident from at least one of:
      the accident type for the real vehicle accident; or
      the roadway configuration for the real vehicle accident,
      and from at least one other characteristic of the real set of characteristics for the real vehicle accident;
   the computer system correlating the determined right of way for the real vehicle accident and the real set of characteristics for the real vehicle accident to a right of way for the past or theoretical vehicle accidents and to the sets of characteristics for the past or theoretical vehicle accidents to determine a set of characteristics from the past or theoretical vehicle accidents that most nearly matches the real set of characteristics for the real vehicle accident; and
   the computer system estimating a base liability of an insured party associated with at least one of the vehicles in the real vehicle accident based on the correlation by the computer system of the determined right of way for the real vehicle accident and the real set of characteristics for the real vehicle accident to a right of way for the past or theoretical vehicle accidents and the sets of characteristics for the theoretical vehicle accidents, wherein the computer system estimating a base liability comprises the computer system extracting, from a database table, at least one base liability associated with the nearest matching set of characteristics from among the sets of characteristics for the past or theoretical vehicle accidents.

2. The method of claim 1, wherein the roadway configuration is selected from the group consisting of a two or more lane road, a divided road with a median that can be crossed, a four-way intersection, a T-angle intersection, a merging of one roadway into another, a curve, a parking lot with two-way traffic, a parking lot with one way traffic, a center turn lane, and a two or more lane road divided by a physical barrier.

3. The method of claim 1, wherein the predetermined set of accident types includes at least two of: a rear ender, a left turn crossing traffic, a left turn across traffic, a left turn entering traffic, a right turn entering traffic, dual turns to same lane, concurrent left turns, a U-turn, a parked vehicle merging into traffic from right, a parked vehicle merging into traffic from left, a merge from left, a merge from right, concurrent merges to a single lane, a collision with a parked vehicle, a collision while backing, a head on, and a straight cross traffic collision.

4. The method of claim 1, wherein the real set of characteristics comprises an impact point for a vehicle in the real vehicle accident.

5. The method of claim 4, wherein the impact point is selected from the group consisting of right front corner, right front fender, right middle, right rear quarter-panel, right rear corner, rear middle, left rear corner, left rear quarter-panel, left middle, left front fender, left front corner, and front middle.

6. The method of claim 1, wherein the real set of characteristics comprises a traffic control.

7. The method of claim 1, wherein the real set of characteristics comprises a traffic control, and wherein the traffic control is selected from the group consisting of a red light, a yellow light, a green light, a left turn arrow, a right turn arrow, a stop sign, a yield sign, a flashing red light, a flashing yellow light, a police officer signaling stop, a police officer signaling proceed, a crossing guard signaling proceed, a crossing guard signaling stop, a flagger signaling proceed, a flagger signaling stop, another person signaling proceed, another person signaling stop, an emergency vehicle, and a school bus.

8. The method of claim 1, wherein the at least one other characteristic comprises a traffic control.

9. The method of claim 1, wherein the at least one other characteristic comprises a jurisdiction.

10. The method of claim 1, wherein the at least one other characteristic comprises a jurisdiction, and wherein the jurisdiction comprises a state or a territory of the United States.

11. The method of claim 1, wherein the at least one other characteristic comprises a traffic control.

12. The method of claim 1, wherein the at least one other characteristic comprises a traffic control, and wherein the traffic control is selected from the group consisting of a red light, a yellow light, a green light, a left turn arrow, a right turn arrow, a stop sign, a yield sign, a flashing red light, a flashing yellow light, a police officer signaling stop, a police officer signaling proceed, a crossing guard signaling proceed, a crossing guard signaling stop, a flagger signaling proceed, a flagger signaling stop, another person signaling proceed, another person signaling stop, an emergency vehicle, and a school bus.

13. The method of claim 1, wherein the at least one other characteristic comprises at least a traffic control and a jurisdiction.

14. The method of claim 1, wherein the at least one other characteristic comprises at least a traffic control and a jurisdiction, and wherein the jurisdiction comprises a state or a territory of the United States.

15. The method of claim 1, wherein the at least one other characteristic comprises at least a traffic control and a jurisdiction, and wherein the traffic control is selected from the group consisting of a red light, a yellow light, a green light, a left turn arrow, a right turn arrow, a stop sign, a yield sign, a flashing red light, a flashing yellow light, a police officer signaling stop, a police officer signaling proceed, a crossing guard signaling proceed, a crossing guard signaling stop, a flagger signaling proceed, a flagger signaling stop, another person signaling proceed, another person signaling stop, an emergency vehicle, and a school bus.

16. The method of claim 1, wherein at least one other characteristic comprises at least one impact points of each vehicle involved in the real vehicle accident.

17. The method of claim 1, wherein at least one other characteristic comprises at least one impact points of each vehicle involved in the real vehicle accident, and wherein each of the impact points comprises one of the following: right front corner, right front fender, right middle, right rear quarter-panel, right rear corner, rear middle, left rear corner, left rear quarter-panel, left middle, left front fender, left front corner, and front middle.

18. The method of claim 1, wherein the base liability is a proportion of the liability of the insured party, wherein the base liability is independent of the actions of the drivers, the conditions of the drivers, the conditions of the vehicles in the accident, and the environmental conditions common to the accident, the method further comprising:
  estimating an effect on liability of the insured party of at least one of:
    the actions of the drivers,
    the conditions of the drivers,
    the conditions of the vehicles in the accident, and
    the environmental conditions common to the accident;
      wherein the effect on the liability of the insured party is a numerical value that increases or decreases in the liability of the insured party relative to the base liability;
  and
  determining an estimate of liability of the party by mathematically combining the estimate of the base liability with the estimated effect.

19. The method of claim 18, wherein estimating the effect comprises estimating an effect of the actions of the drivers in the accident on the liability of the insured party.

20. The method of claim 18, wherein estimating the effect comprises estimating an effect of the conditions of the drivers in the accident on the liability of the insured party.

21. The method of claim 18, wherein estimating the effect comprises estimating an effect of the condition of vehicles in the accident on the liability of the insured party.

22. The method of claim 18, wherein estimating the effect comprises estimating an effect of the environmental conditions common to vehicles in the accident on the liability of the insured party.

23. The method of claim 18, wherein the estimated effect of one or more factors comprises a proportion of liability for each of one or more actions of the drivers, one or more conditions of the drivers, one or more conditions of the vehicles in the accident, and one or more environmental conditions common to the vehicles in the accident, wherein determining the estimate of liability comprises adding or subtracting to the base liability the proportion of liability associated with one or more actions of the drivers, one or more conditions of the drivers, one or more conditions of the vehicles in the accident, or one or more environmental conditions common to the vehicles in the accident.

24. The method of claim 18, wherein determining the estimate of liability of the party comprises multiplying the base liability by the sum of the estimated effects of one or more actions of the drivers, one or more conditions of the drivers, one or more conditions of the vehicles in the accident, and one or more environmental conditions common to the vehicles in the accident.

25. The method of claim 18, wherein combining the estimated base liability with the estimated effect on the liability of the party comprises shifting a portion of the liability for the vehicle accident from the party to another party or shifting a portion of the liability for the vehicle accident to the party from another party.

26. The method of claim 1, wherein the accident type for the real vehicle accident is one accident type selected from a set of two or more predetermined accident types, wherein the right of way in the real vehicle accident is determined based on which accident type is selected from the set of predetermined accident types.

27. The method of claim 1, wherein the accident type for the real vehicle accident is one accident type selected from a set of two or more predetermined accident types, wherein determining the right of way in the real vehicle accident comprises determining whether an intersection is present or not present for the real vehicle accident based on which accident type is selected from the set of predetermined accident types.

28. The method of claim 1, wherein the roadway configuration for the real vehicle accident is one roadway configuration selected from a set of two or more predetermined roadway configurations, wherein the right of way in the real vehicle accident is determined based on which roadway configuration is selected from the set of predetermined roadway configurations.

29. The method of claim 1, wherein the roadway configuration for the real vehicle accident is one roadway configuration selected from a set of two or more predetermined roadway configurations, wherein determining the right of way in the real vehicle accident comprises determining whether an intersection is present or not present for the real vehicle accident based on which roadway configuration is selected from the set of predetermined roadway configurations.

30. The method of claim 1,
wherein each of at least two sets of characteristics for the past or theoretical accidents is associated with a first base liability corresponding to a first vehicle in a past or theoretical accident having the right of way in the past or theoretical accident and a second base liability corresponding to a second vehicle having the right of way in the past or theoretical accident;
wherein the computer system estimating the base liability comprises the computer system extracting, from a database table, at least one of the first base liability or the second base liability associated with the nearest matching set of characteristics for the past or theoretical accidents, wherein the estimated liability for the vehicle in the real vehicle accident is based on the first base liability if the insured party had the right of way, wherein the estimated liability for the vehicle in the real vehicle accident is based on the estimate of the second base liability if the insured party did not have the right of way.

31. The method of claim 1,
wherein the real set of characteristics for the real vehicle accident further comprises:
a pair of impact points for the real vehicle accident, wherein one of the impact points of the pair is an impact point for a first vehicle in the real vehicle accident and the other impact point of the pair is an impact point for a second vehicle in the real vehicle accident,
the method further comprising the computer system searching, from within a database table having pairs of impact points for the past or theoretical accidents, for a pair of impact points associated with the roadway configuration for the real vehicle accident and the accident type for the real vehicle accident that is the nearest match to the pair of impact points for the real vehicle accident,
wherein the estimate of the base liability for the real vehicle accident is based at least in part on a base liability associated with the nearest matching pair of impact points.

32. A system for estimating liability for a vehicle accident, comprising:
a CPU;
a data memory coupled to the CPU; and
a system memory coupled to the CPU, wherein the system memory is configured to store one or more computer programs executable by the CPU, and wherein the computer programs are executable to implement a method for estimating liability, the method comprising:
providing to the computer system a real set of characteristics of a real vehicle accident involving two or more vehicles, wherein the real set of characteristics of the real vehicle accident comprises:
an accident type for the real vehicle accident, wherein the accident type for the real vehicle accident specifies a relationship between two or more vehicles' paths on a roadway at the time of the real vehicle accident; and
a roadway configuration for the real vehicle accident;
wherein the data memory comprises sets of characteristics for past or theoretical vehicle accidents, wherein the past vehicle accidents are accidents that actually occurred in the past, wherein the theoretical vehicle accidents are accidents that might occur, wherein the set of characteristics for at least one of the past or theoretical vehicle accidents comprises:
an accident type for the past or theoretical vehicle accident, wherein the accident type for the past or theoretical vehicle accident specifies a relationship between two or more vehicles' paths on a roadway at the time of the past or theoretical vehicle accident; and
a roadway configuration for the past or theoretical vehicle accident;
wherein each of at least two of the sets of characteristics for the past or theoretical vehicle accidents is associated with at least one base liability;
automatically determining a right of way in the real vehicle accident from at least one of:
the accident type for the real vehicle accident; or
the roadway configuration for the real vehicle accident, and from at least one other characteristic of the real set of characteristics for the real vehicle accident;
correlating the determined right of way for the real vehicle accident and the real set of characteristics for the real vehicle accident to a right of way for the past or theoretical vehicle accidents and the sets of characteristics for the past or theoretical vehicle accidents to determine a set of characteristics from the past or theoretical vehicle accidents that most nearly matches the real set of characteristics for the real vehicle accident; and
estimating a base liability of an insured party associated with at least one of the vehicles in the real vehicle accident based on the correlation by the computer system of the determined right of way for the real vehicle accident and the real set of characteristics for the real vehicle accident to a right of way for the past or theoretical vehicle accidents and the sets of characteristics for the past or theoretical vehicle accidents, wherein estimating the base liability comprises the computer system extracting, from a database table, at least one base liability associated with the nearest matching set of characteristics from among the sets of characteristics for the past or theoretical vehicle accidents.

33. A computer-readable storage medium comprising program instructions stored thereon, wherein the program instructions are computer-executable to implement a method for estimating liability for a vehicle accident, the method comprising:
providing to a computer system a real set of characteristics of a real vehicle accident involving two or more vehicles, wherein the real set of characteristics of the real vehicle accident comprises:
an accident type for the real vehicle accident, wherein the accident type for the real vehicle accident specifies a relationship between two or more vehicles' paths on a roadway at the time of the real vehicle accident; and
a roadway configuration for the real vehicle accident;
wherein the computer system is configured to access a memory, and wherein the memory comprises sets of characteristics for past or theoretical vehicle accidents, wherein the past vehicle accidents are accidents that actually occurred in the past, wherein the theoretical vehicle accidents are accidents that might occur, wherein the set of characteristics for at least one of the past or theoretical vehicle accidents comprises:
  an accident type for the past or theoretical vehicle accident, wherein the accident type for the past or theoretical vehicle accident specifies a relationship between two or more vehicles' paths on a roadway at the time of the past or theoretical vehicle accident; and
  a roadway configuration for the past or theoretical vehicle accident;
wherein each of at least two of the sets of characteristics for the past or theoretical vehicle accidents is associated with at least one base liability;
automatically determining a right of way in the real vehicle accident from at least one of:
  the accident type for the real vehicle accident; or
  the roadway configuration for the real vehicle accident,
  and from at least one other characteristic of the real set of characteristics for the real vehicle accident; and
correlating the determined right of way for the real vehicle accident and the real set of characteristics for the real vehicle accident to a right of way for the past or theoretical vehicle accidents and the sets of characteristics for the past or theoretical vehicle accidents to determine a set of characteristics from the past or theoretical vehicle accidents that most nearly matches the real set of characteristics for the real vehicle accident; and
estimating a base liability of an insured party associated with at least one of the vehicles in the real vehicle accident based on the correlation by the computer system of the determined right of way for the real vehicle accident and the real set of characteristics for the real vehicle accident to a right of way for the past or theoretical vehicle accidents and the sets of characteristics for the past or theoretical vehicle accidents, wherein estimating a base liability comprises the computer system extracting, from a database table, at least one base liability associated with the nearest matching set of characteristics from among the sets of characteristics for the past or theoretical vehicle accidents.

* * * * *

UNITED STATES PATENT AND TRADEMARK OFFICE
CERTIFICATE OF CORRECTION

| | |
|---|---|
| PATENT NO. | : 7,904,318 B2 |
| APPLICATION NO. | : 09/969017 |
| DATED | : March 8, 2011 |
| INVENTOR(S) | : Wahlbin et al. |

It is certified that error appears in the above-identified patent and that said Letters Patent is hereby corrected as shown below:

In the Inventors:

Please delete "Stephan Wahlbin" and substitute therefor -- Stefan Wahlbin --.

Signed and Sealed this
Twenty-first Day of June, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,904,318 B2 | Page 1 of 1 |
| APPLICATION NO. | : 09/969017 | |
| DATED | : March 8, 2011 | |
| INVENTOR(S) | : Wahlbin et al. | |

It is certified that error appears in the above-identified patent and that said Letters Patent is hereby corrected as shown below:

Title Page, Item (75) Inventors,

Please delete "Stephan Wahlbin" and substitute therefor -- Stefan Wahlbin --.

This certificate supersedes the Certificate of Correction issued June 21, 2011.

Signed and Sealed this
Twenty-sixth Day of July, 2011

David J. Kappos
*Director of the United States Patent and Trademark Office*